(12) United States Patent
Mehta et al.

(10) Patent No.: US 6,956,040 B2
(45) Date of Patent: Oct. 18, 2005

(54) OXAZOLIDINONE PIPERAZINYL DERIVATIVES AS POTENTIAL ANTIMICROBIALS

(75) Inventors: Anita Mehta, Haryana (IN); Sudershan K. Arora, Maharashtra (IN); Biswajit Das, Haryana (IN); Abhijit Ray, Edison, NJ (US); Sonali Rudra, Delhi (IN); Ashok Rattan, Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 63 days.

(21) Appl. No.: 10/051,784

(22) Filed: Jan. 17, 2002

(65) Prior Publication Data

US 2003/0119817 A1 Jun. 26, 2003

Related U.S. Application Data

(63) Continuation-in-part of application No. 09/906,215, filed on Jul. 16, 2001, now Pat. No. 6,734,307.

(51) Int. Cl.$^7$ .................. C07D 413/14; A61K 31/496; A61P 31/04

(52) U.S. Cl. ................. 514/254.02; 544/369

(58) Field of Search .................... 514/236.5, 253.1, 514/254.02; 544/121, 364, 369

(56) References Cited

U.S. PATENT DOCUMENTS

| | | | |
|---|---|---|---|
| 4,801,600 A | 1/1989 | Wang et al. | 514/376 |
| 4,921,869 A | 5/1990 | Wang et al. | 514/376 |
| 5,254,577 A | 10/1993 | Carlson et al. | 514/376 |
| 5,547,950 A | 8/1996 | Hutchinson et al. | 514/252 |
| 5,700,799 A | 12/1997 | Hutchinson et al. | 514/235 |
| 5,981,528 A | 11/1999 | Gravestock | 514/252 |
| 6,277,985 B1 * | 8/2001 | Gadwood et al. | 544/60 |

FOREIGN PATENT DOCUMENTS

| | | |
|---|---|---|
| EP | 0 352 781 | 7/1989 |
| EP | 0 312 000 | 3/1992 |
| WO | WO 90/02744 | 3/1990 |
| WO | WO 93/09103 | 5/1993 |
| WO | WO 93/23384 | 11/1993 |
| WO | WO 95/14684 | 6/1995 |
| WO | WO 95/25106 | 9/1995 |
| WO | WO 97/14690 | 4/1997 |
| WO | WO 98/01446 | 1/1998 |
| WO | WO 00/32599 | 6/2000 |
| WO | WO 02/06278 | 1/2002 |

OTHER PUBLICATIONS

Foye, William O. et al, "Principles of Medicianl Chemistry, 4ed", Williams & Wilkins, 1995, Baltimore, 83, 89 and 111–113.*

Testa, B.,. "Burger's Medicinal Chemistry, 5ed, Part I, Wolff, Manfred Ed.", John Wiley & Sons, 1995, pp. 129, 130, and 143–146.*

Gregory W.A., et al., "Antibacterials. Synthesis and Structure—Activity Studies of 3–Aryl–2–oxooxazolidines. 1. The "B" Group," J.Med.Chem., 32, 1673–81 (1989).

Gregory W.A., et al., "Antibacterials. Synthesis and Structure—Activity Studies of 3–Aryl–2–oxooxazolidines. 2. The "A" Group," J.Med.Chem., 33, 2569–78 (1990).

Wang C., et al., "Chiral Synthesis of Dup 721, A New Antibacterial Agent", Tetrahedron, 45, 1323–26 (1989).

Brittelli, et al., "Antibacterials. Synthesis and Structure—Activity Studies of 3–Aryl–2–oxooxazolidines. 4. Multiply–Substituted Aryl Derivatives," J.Med. Chem., 35, 1156 (1992).

Pae, et al., "Synthesis and in Vitro Activity of New Oxazolidinone Antibacterial Agents Having Substituted Isoxazoles," Bio–organic and Medicinal Chemistry Letters, 9, pp. 2679–2684, 1999.

Pae, et al., "3D QSAR Studies on New Oxazolidinone Antibacterial Agents by Comparitave Molecular Field Analysis," Bioorganic & Medicinal Chemistry Letters 9, pp. 2685–2690, 1999.

Antibacterial & Antifungal Drug Discovery & Development Summit, Strategic Research Institute, Jun. 28–29, 2001, Amsterdam, The Netherlands; Poster Nos. 1822–1834.

40$^{th}$ Interscience Conference on Antimicrobial Agents and Chemotherapy, Sep. 17–20, 2000, Toronto, Canada.

(Continued)

Primary Examiner—Thomas C. McKenzie
(74) Attorney, Agent, or Firm—Jay R. Deshmukh, Esq.; George F. Heibel, Esq.

(57) ABSTRACT

The present invention relates to certain substituted phenyl piperazinyl oxazolidinones, for example, to those having the structure of Formula I

FORMULA I with the variables as defined within, and to processes for the synthesis of the same. This invention also relates to pharmaceutical compositions containing the compounds of the present invention as antimicrobials. The compounds are useful antimicrobial agents, effective against a number of human and veterinary pathogens, including gram-positive aerobic bacteria such as multiply-resistant staphylococci, streptococci and enterococci as well as anaerobic organisms such as *Bacterioides* spp. and *Clostridia* spp. species, and acid fast organisms such as *Mycobacterium tuberculosis*, *Mycobacterium avium* and *Mycobacterium* spp.

4 Claims, No Drawings

OTHER PUBLICATIONS

Blake and Metcalfe, "A Shared Noncapsular Antigen Is Responsible for False–Positive Reactions by *Staphylococcus epidermis* in Commercial Agglutination Tests for *Staphylococcus aureus*", *Journal of Clinical Microbiology*, 39(2):544–550 (2001).

Borch et al., "Synthesis and Evaluation of Nitroheterocyclic Phosphoramidates as Hypoxia–Selective Alkalyting Agents," *Journal of Medicinal Chemistry*, 43: 2258–2265 (2000).

Fournari and Tirouflet, *Bull. Soc. Chim. France*, p 484–487 (1963).

*Chemical Abstracts*, 71:332, abst. 101697d (1969).

Mermel et al., "Guidelines for the Management of Intravascular Catheter–Related Infections", *Clinical Infectious Diseases*, 32:1249–1272 (2001).

Divald, et al, "Chemistry of 2–(Chloromethyl)furans. Reaction of 2–(Chloromethyl)futans with Aqueous Potassium Cyanide and Other Nucleophiles", *Journal of Organic Chemistry*, 41:2835–2845 (1976).

Gilman et al, "Orientation in the Furan Nucleau:, VI. β–Substituted Furans", *Journal of the American Chem. Society*, 55:2903–2909 (1933).

Hulbert, et al, "Structure and Antischistosomal Activity in the Nitrofuran Series. Requirement for a 5–Nitro–2–furyl Vinyl Moiety Based on Comparison of 3–5–Nitro–2–furyl–Substituted Propionic, Acrylic, and Propiolic Acid Derivatives.", *Journal of Medicinal Chemistry*, 16:72–78 (1973).

Zimmerli, "Experimental models in the investigation of device–related infections", *Journal of Antimicrobial Chemotherapy* 31(Suppl. D):97–102 (1993).

Khim. *Geterosikl. Soedin.*, 6:747–50 (1982).

Makosza, et al, "Dihalomethylation of Nitroarenes via Vicarious Nucleophilic Substitution of Hydrogen with Trihalomethyl Carbanions.", *Journal of Organic Chemistry*, 54:5094–5100 (1989).

Park et al, "Antibacterials. Synthesis and Structure–Activity Studies of 3–Aryl–2–oxooxazoidines. 4. Multiply–Substituted Aryl Derivatives", *Journal of Medicinal Chemistry*, 35:1156–1165 (1992).

Polonio et al., "Eradication of Biofilm–Forming *Staphylococcus epidermis* (RP62A) by a Combination of Sodium Salicylate and Vancomycin", *Antimicrobial Agents and Chemotherapy*, 45(11):3262–3266 (2001).

Tanaka, et al, "Studies on Furan Derivatives. IX.[1)] Nucleophilic Substitution of 5–Nitro–2–furancarbaldehyde: Preparation of 5–Phenoxy–2–furancarbaldehydes.", *Chemical & Pharmaceutical Bulletin*, 28(9):2846–2849 (1980).

"Catheter–Related Bloodstream Infections—Developing Antimicrobial Drugs for Treatment", *FDA Guidance for Industry* (Oct. 1999).

* cited by examiner

OXAZOLIDINONE PIPERAZINYL DERIVATIVES AS POTENTIAL ANTIMICROBIALS

CROSS-REFERENCE TO RELATED APPLICATION

This application is a continuation in part of, and claims priority under 35 U.S.C. §120 of, U.S. patent application Ser. No. 09/906,215, filed Jul. 16, 2001 now U.S. Pat. No. 6,734,307.

FIELD OF THE INVENTION

The present invention relates to certain substituted phenyl oxazolidinones and to processes for the synthesis of the same. This invention also relates to pharmaceutical compositions containing the compounds of the present invention as antimicrobials. The compounds are useful antimicrobial agents, effective against a number of human and veterinary pathogens, including gram-positive aerobic bacteria such as multiply-resistant staphylococci, streptococci and enterococci as well as anaerobic organisms such as *Bacterioides* spp. and *Clostridia* spp. species, and acid fast organisms such as *Mycobacterium tuberculosis*, *Mycobacterium avium* and *Mycobacterium* spp.

BACKGROUND OF THE INVENTION

Increasing antibacterial resistance in Gram positive bacteria has presented a formidable treatment problem. The enterococci, although traditionally non virulent pathogens, have been shown, when associated with Vancomycin resistance, to have an attributable mortality of approximately 40%. *Staphylococcus aureus*, the traditional pathogen of post operative wounds, has been resistant to Penicillin due to production of penicillinases. This resistance was overcome by the development of various penicillinase stable β lactams. But the pathogen responded by synthesizing a modified target penicillin binding protein-2' leading to less affinity for β lactam antibiotics and a phenotype known as Methicillin Resistant *S. aureus* (MRSA). These strains, till recently were susceptible to Vancomycin, which inspite of its various drawbacks, has become the drug of choice for MRSA infections. *Streptococcus pneumoniae* is a major pathogen causing pneumonia, sinusitis and meningitis. Until very recently it was highly susceptible to penicillin. Recently though, different PBP 2' strains with different susceptibility to penicillin have been reported from across the globe.

Oxazolidinones are a new class of synthetic antimicrobial agents which kill gram positive pathogens by inhibiting a very early stage of protein synthesis. Oxazolidinones inhibit the formation of ribosomal initiation complex involving 30S and 50S ribosomes leading to prevention of initiation complex formation. Due to their novel mechanism of action, these compounds are active against pathogens resistant to other clinically useful antibiotics.

WO93/23384 application discloses phenyloxazolidinones containing a substituted diazine moiety and their uses as antimicrobials.

WO93/09103 application discloses substituted aryl and heteroaryl-phenyloxazolidinones useful as antibacterial agents WO90/02744 application discloses 5-indolinyl-5β-amidomethyloxazolidinones, 3-(fused ring substituted) phenyl-5β-amidomethyloxazolidinones which are useful as antibacterial agents.

European Patent Publication 352,781 discloses phenyl and pyridyl substituted phenyl oxazolidinones.

European Patent Application 312,000 discloses phenylmethyl and pyridinylmethyl substituted phenyl oxazolidinones.

U.S. Pat. No. 5,254,577 discloses nitrogen heteroaromatic rings attached to phenyloxazolidinone.

U.S. Pat Nos. 5,547,950 and 5,700,799 also disclose the phenyl piperazinyl oxazolidinones.

Other references disclosing various phenyloxazolidinones include U.S. Pat Nos. 4,801,600 and 4,921,869; Gregory W. A., et al., *J. Med. Chem.*, 32, 1673–81 (1989); Gregory W. A., et al., *J. Med. Chem.*, 33, 2569–78 (1990); Wang C., et al., *Tetrahedron*, 45, 1323–26 (1989); Brittelli, et al., *J. Med. Chem.*, 35, 1156 (1992); and *Bio-organic and Medicinal Chemistry Letters*, 9, pp. 2679–2684, 1999.

SUMMARY OF THE INVENTION

The objective of this invention is to synthesize, identify and profile oxazolidinone molecules which have good activity against multiply resistant gram positive pathogens like MRSA, VRE and PRSP. Some of these molecules have activity against MDR-TB and MAI strains, while others have significant activity against important anaerobic bacteria.

The compounds of the present invention are related by their substituted phenyloxazolidinone ring structure in the compounds disclosed to the publications described above except that the subject compounds have a diazine moiety attached to the phenyloxazolidinone which is further substituted by heterocyclic, aryl, substituted aryl, heteroaroamatic ring therefore the compounds are unique and have superior antibacterial activity.

Another object of the present invention is to provide processes for the novel phenyloxazolidinones derivatives that exhibit significantly greater antibacterial activity, than available with the present compounds against multiply resistant gram positive pathogens like MRSA, VRE and PRSP against MDR-TB and MAI strains, in order to provide safe and effective treatment of bacterial infections.

In order to achieve the above-mentioned objectives and in accordance with the purpose of the invention as embodied and broadly described herein, there is provided a process for the synthesis of novel phenyloxazolidinone derivatives represented by Formula I

FORMULA I

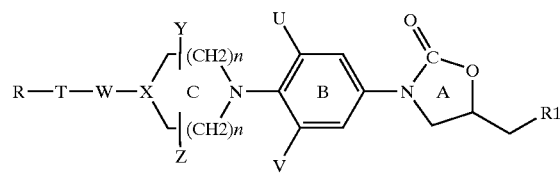

wherein

T is five to seven membered heterocyclic ring, aryl, substituted aryl, bound to the ring C with a linker W. Preferred forms of T are selected from aryl and five membered heteroaryl which are further substituted by a group represented by R, wherein R is selected from the group consisting of alkyl ($C_{1-6}$), halogen, —CN, $COR_5$, $COOR_5$, $N(R_6,R_7)$, $CON(R_6, R_7)$, $CH_2NO_2$, $NO_2$, $CH_2R_8$, $CHR_9$, —CH=N—$OR_{10}$, —C=CH—$R_5$, wherein $R_5$ is selected from H, optionally substituted $C_1$–$C_{12}$ alkyl, $C_{3-12}$ cycloalkyl, aryl, heteroaryl, $R_6$ and $R_7$, are independently selected from H, optionally substituted $C_{1-12}$ alkyl, $C_{3-12}$ cycloalkyl, $C_{1-6}$ alkoxy; $R_8$ and $R_9$ are independently selected from H, $C_{5-6}$ alkyl, F, Cl, Br, $C_{1-12}$ alkyl substituted with one or more of F, Cl, Br, I, $OR_5$, $SR_4$, $N(R_6,R_7)$ wherein $R_5$ is selected from H, $C_{1-12}$ alkyl, $C_{3-12}$ cycloalkyl, $C_{1-6}$ alkoxy, $C_{1-6}$ alkyl substituted with one or more F, Cl, Br, I or OH and $R_6$ and $R_7$ are the same as defined earlier, $R_4$ is selected from H, optionally substituted $C_{5-12}$ alkyl, $C_{1-12}$ alkyl, $C_{3-12}$ cycloalkyl, $C_{1-6}$ alkoxy, $C_{1-6}$ alkyl, aryl, heteroaryl, n is an integer in the range from 0 to 3;

X is CH, CH—S, CH—O and N;

Y and Z are independently selected from hydrogen, $C_{1-6}$ alkyl $C_{3-12}$ and cycloalkyl $C_{0-3}$ bridging groups;

U and V are independently selected from optionally substituted $C_{1-6}$ alkyl, F, Cl, Br, $C_{1-12}$ alkyl substituted with one or more of F, Cl, Br, I, preferably U and V are hydrogen or fluoro;

W is selected from the group $CH_2$, CO, $CH_2NH$, —$NHCH_2$, —$CH_2NHCH_2$, —$CH_2$—$N(R_{11})CH_2$—, —CO—CO—, $CH_2(R_{11})N$—, $CH(R_{11})$, S, $CH_2(CO)$, $N(R_{11})$ wherein $R_{11}$ is hydrogen, optionally substituted $C_{1-12}$ alkyl, $C_{3-12}$ cycloalkyl, $C_{1-6}$ alkoxy, $C_{1-6}$ alkyl, aryl or heteroaryl;

$R_1$ is selected from the group consisting of —NHC(=O)$R_2$ wherein $R_2$ is hydrogen, $C_{1-12}$ alkyl, $C_{3-12}$ cycloalkyl, $C_{1-6}$ alkoxy, $C_{1-6}$ alkyl substituted with one or more of F, Cl, Br, I or OH; $N(R_3, R_4)$; —$NR_2C(=S)R_3$; $NR_2C(=S)SR_3$ wherein $R_2$ is the same as defined above, $R_3, R_4$ are independently selected from hydrogen, $C_{1-12}$ alkyl, $C_{3-12}$ cycloalkyl, $C_{1-6}$ alkoxy, $C_{1-6}$ alkyl substituted with one or more of F, Cl, Br, I or OH.

Preferred compounds of Formula I have $R_1$ as acetamide and the most preferred compounds in this series would be prepared as the optically pure enantiomers having the (S)-configuration according to the Cahn-Ingold-Prelog notation at $C_5$ of the oxazolidinone ring. The (S)-enantiomer of this series of compounds is preferred since it has two times more antibacterial activity than the corresponding racemic compound. The scope of the individual isomers and mixture of enantiomers of the structural Formula I are also covered in this invention.

Still more preferred compounds of the Formula I containing D ring as furanyl, thienyl and pyrrolyl ring systems (M=O, S, NH, N—CH3) and further substituted by substitutions Q and P is represented by Formula II

FORMULA II

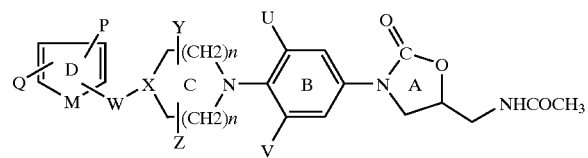

wherein
U and V are independently selected from optionally substituted $C_{1-6}$ alkyl, F, Cl, Br, $C_{1-12}$ alkyl substituted with one or more of F, Cl, Br, I, preferably U and V are hydrogen or fluoro;

X is CH, CH—S, CH—O and N;

Y and Z are independently selected from hydrogen, $C_{1-6}$ alkyl, $C_{3-12}$ and cycloalkyl $C_{0-3}$ bridging groups; and, W is selected from the group $CH_2$, CO, $CH_2NH$, —$NHCH_2$, —$CH_2NHCH_2$, —$CH_2$—$N(R_{11})CH_2$—, —CO—CO—, $CH_2(R_{11})N$—, $CH(R_{11})$, S, $CH_2(CO)$, $N(R_{11})$ wherein $R_{11}$ is hydrogen, optionally substituted $C_{1-12}$ alkyl, $C_{3-12}$ cycloalkyl, $C_{1-6}$ alkoxy, $C_{1-6}$ alkyl, aryl or heteroaryl.

Preferred compounds of Formula II of this invention are those when Q and P are independently selected from the group consisting of —CN, $COR_5$, $COOR_5$, $N(R_6, R_7)$, $CON(R_6,R_7)$, $CH_2NO_2$, $NO_2$, $CH_2R_8$, $CHR_9$, —CH=N—$OR_{10}$, C=CH—$R_5$, wherein $R_5$ is selected from the group consisting of H, optionally substituted $C_{1-12}$ alkyl, $C_{3-12}$ cycloalkyl, aryl, or heteroaryl; $R_6$, $R_7$ are independently selected from H, optionally substituted $C_{1-12}$ alkyl, $C_{3-12}$ cycloalkyl, $C_{1-6}$ alkoxy, $R_8$, $R_9$ and are independently selected from the group consisting of H, $C_{1-6}$ alkyl, F, Cl, Br, $C_{1-12}$ alkyl substituted with one or more of F, Cl, Br, I, $OR_4$, $SR_4$, wherein $R_4$ is the same as defined earlier, $N(R_6, R_7)$, $R_{10}$=H, optionally substituted $C_{1-12}$ alkyl, $C_{3-12}$ cycloalkyl, $C_{1-6}$ alkoxy, $C_{1-6}$ alkyl, aryl, heteroaryl except W=(CO), Q and P=H and M=S.

In the more preferred compounds represented by Formula II ring C may be 6–8 membered in size and the larger rings may have either two or three carbons between each nitrogen atom, for example:

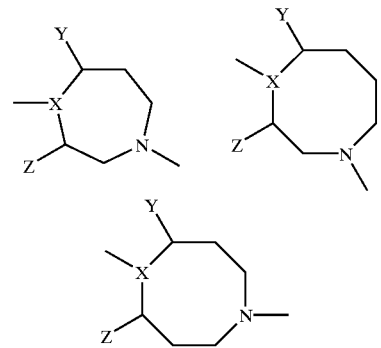

The ring C may be bridged to form a bicyclic system as shown below:

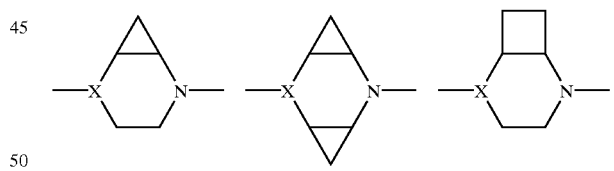

When ring C is optionally substituted at positions Y and Z with alkyl groups, cycloalkyl groups, fluoro group, carboxylic and corresponding esters, amides, substituted alkyls or bridging alkyl groups are as shown below:

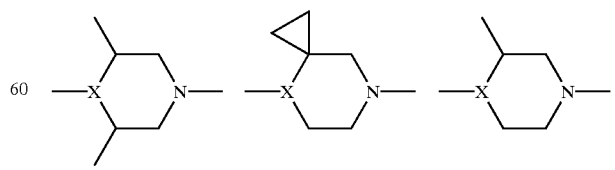

When ring C is 6 membered in size and X is —CH—($NR_{11}$), the following rings are preferred ones wherein $R_{11}$ is the same as defined earlier.

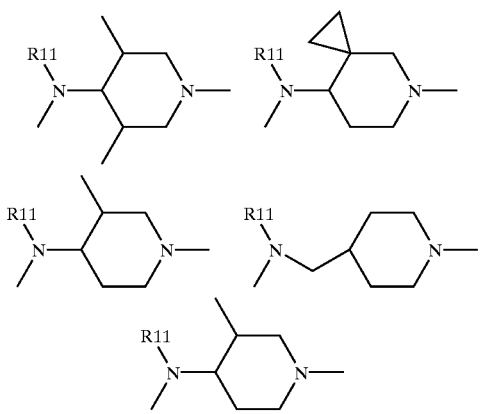

In addition to the above, ring C also includes the following structures:

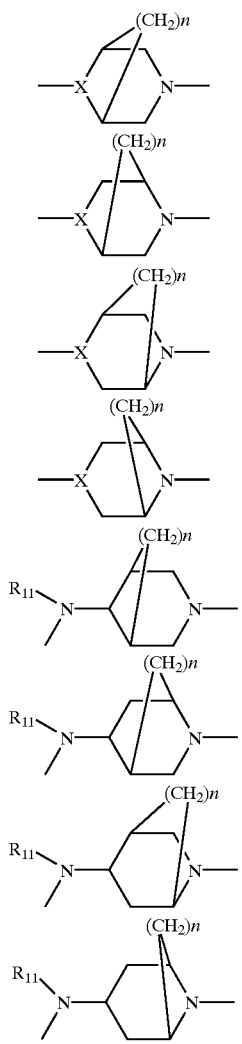

Still more preferred compounds of Formula II when M=Sulphur is represented by Formula III

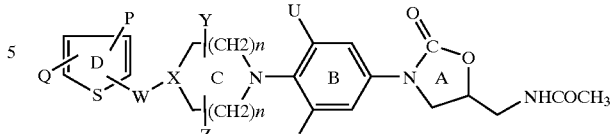

FORMULA III wherein

U and V are independently selected from optionally substituted $C_{1-6}$ alkyl, F, Cl, Br, $C_{1-12}$ alkyl substituted with one or more of F, Cl, Br, I, preferably U and V are hydrogen or fluoro;

X is CH, CH—S, CH—O and N;

Y and Z are independently selected from hydrogen, $C_{1-6}$ alkyl, $C_{3-12}$ and cycloalkyl $C_{0-3}$ bridging groups;

W is selected from the group $CH_2$, CO, $CH_2NH$, —$NHCH_2$, —$CH_2NHCH_2$, —$CH_2$—$N(R_{11})CH_2$—, —CO—CO—, $CH_2(R_{11})N$—, $CH(R_{11})$, S, $CH_2(CO)$, $N(R_{11})$ wherein $R_{11}$ is hydrogen, optionally substituted $C_{1-12}$ alkyl, $C_{3-12}$ cycloalkyl, $C_{1-6}$ alkoxy, $C_{1-6}$ alkyl, aryl or heteroaryl;

Q and P are independently selected from the group consisting of —CN, $COR_5$, $COOR_5$, $N(R_6, R_7)$, CON $(R_6,R_7)$, $CH_2NO_2$, $NO_2$, $CH_2R_8$, $CH_2R_9$, —CH=N— $OR_{10}$, C=CH—$R_5$, wherein $R_5$ is selected from the group consisting of H, optionally substituted $C_{1-12}$ alkyl, $C_{3-12}$ cycloalkyl, aryl, or heteroaryl; $R_6$, $R_7$ are independently selected from H, optionally substituted $C_{1-12}$ alkyl, $C_{3-12}$ cycloalkyl, $C_{1-6}$ alkoxy, $R_8$, $R_9$ and are independently selected from the group consisting of H, $C_{1-6}$ alkyl, F, Cl, Br, $C_{1-12}$ alkyl substituted with one or more of F, Cl, Br, I, $OR_4$, $SR_4$, wherein R4 is the same as defined earlier $N(R_6, R_7)$, $R_{10}$=H, optionally substituted $C_{1-12}$ alkyl, $C_{3-12}$ cycloalkyl, $C_{1-6}$ alkoxy, $C_{1-6}$ alkyl, aryl, heteroaryl except W=(CO), Q and P=H.

More preferred Q, P substitutions are nitro, aldehydes and halides.

Preferably W is selected from the groups consisting of $CH_2$, C(=O), C(=O)—C(=O), $CH_2NH$, —$NHCH_2$, —$CH_2NHCH_2$, —$CH_2$—$N(CH3)CH_2$—, $CH_2(CH_3)N$—, $CH(CH_3)$, S and $CH_2(C=O)$, —NH. The most preferred compounds of Formula III are as follows:

- (S)-N-[[3-[4-[4-(N-methyl-N-2-thienyl(5-nitro)methyl) aminopiperidine-1-yl]-3-fluorophenyl]-2-oxo-oxazolidin-5-yl]methyl]acetamide
- (S)-N[[3-[3-Fluoro-4-[N-1[4-{2-(2-thienyl)dicarbonyl}] piperazinyl]phenyl]2-oxo-5-oxazolidinyl]methyl] acetamide
- (S)-N[[3-[3-Fluoro-4-[N-1[4-(5-nitro-2-thienoyl)] piperazinyl]phenyl]2-oxo-5-oxazolidinyl]methyl] acetamide hydrochloride Still more preferred compounds of Formula II is represented by Formula IV

FORMULA IV

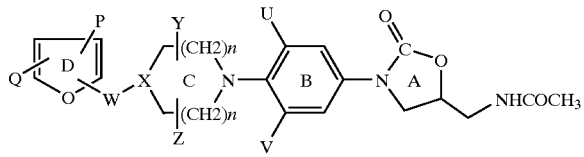

containing oxygen atom in ring D of Formula II, wherein

U and V are independently selected from optionally substituted $C_{1-6}$ alkyl, F, Cl, Br, $C_{1-12}$ alkyl substituted with one or more of F, Cl, Br, I, preferably U and V are hydrogen or fluoro;

X is CH, CH—S, CH—O and N;

Y and Z are independently selected from hydrogen, $C_{1-6}$ alkyl, $C_{3-12}$ and cycloalkyl $C_{0-3}$ bridging groups;

W is selected from the group $CH_2$, CO, $CH_2NH$, —$NHCH_2$, —$CH_2NHCH_2$, —$CH_2$—$N(R_{11})CH_2$—, —CO—CO—, $CH_2(R_{11})N$—, $CH(R_{11})$, S, $CH_2(CO)$, $N(R_{11})$ wherein $R_{11}$ is hydrogen, optionally substituted $C_{1-12}$ alkyl, $C_{3-12}$ cycloalkyl, $C_{1-6}$ alkoxy, $C_{1-6}$ alkyl, aryl or heteroaryl;

Q and P are independently selected from the group consisting of —CN, $COR_5$, $COOR_5$, $N(R_6, R_7)$, CON $(R_6,R_7)$, $CH_2NO_2$, $NO_2$, $CH_2R_8$, $CHR_9$, —CH=N—$OR_{10}$, $C=CH-R_5$, wherein $R_5$ is selected from the group consisting of H, optionally substituted $C_{1-12}$alkyl, $C_{3-12}$ cycloalkyl, aryl, or heteroaryl; $R_6$, $R_7$ are independently selected from H, optionally substituted $C_{1-12}$ alkyl, $C_{3-12}$ cycloalkyl, $C_{1-6}$ alkoxy, $R_8$, $R_9$ and are independently selected from the group consisting of H, $C_{1-6}$ alkyl, F, Cl, Br, $C_{1-12}$ alkyl substituted with one or more of F, Cl, Br, I, $OR_4$, $SR_4$,$N(R_6, R_7)$, $R_{10}$=H, optionally substituted $C_{1-12}$ alkyl, $C_{3-12}$ cycloalkyl, $C_{1-6}$ alkoxy, $C_{1-6}$ alkyl, aryl or heteroaryl.

More preferred Q and P substitutions are nitro, aldehydes and halides.

Preferably W is selected from the groups consisting of $CH_2$, C(=O), C(=O)—C(=O), $CH_2NH$, —$NHCH_2$, —$CH_2NHCH_2$, —$CH_2$—$N(CH_3)CH_2$—, $CH_2(CH_3)N$—, $CH(CH_3)$, S, $CH_2(C=O)$, and —NH.

The most preferred compounds of Formula IV are as follows:

-(S)-N-[[3-Fluoro-4-[N-1[4-(5-nitro-2-furoyl) piperazinyl]phenyl]-2-oxo-5-oxazolidinyl]methyl] acetamide.

-(S)-N-[[3-[3-fluoro-4-[N-1-[4-{2-furyl-(5-nitro) methyl}]piperazinyl]phenyl]-2-oxo-5-oxazolidinyl] methyl]acetamide.

-(S)-N-[[3-[4-[4-(N-methyl-N-(5-nitro-2-furoyl) aminopiperidine-1-yl]-3-fluorophenyl]-2-oxo-oxazolidin-5-yl]methyl]acetamide.

-(S)-N-[[3-[4-[4-(N-methyl-N-2-furyl(5-nitro)methyl) aminopiperidine-1-yl]-3-fluorophenyl]-2-oxo-oxazolidin-5-yl]methyl]acetamide.

The compounds of the present invention are useful as antimicrobial agents, effective against a number of human and veterinary pathogens, particularly aerobic Gram-positive bacteria, including multiply-antibiotic resistant staphylococci and streptococci, as well as anaerobic organisms such as *Mycobacterium tuberculosis* and other *mycobacterium* species.

For preparing pharmaceutical compositions from the compounds described by this invention, inert, pharmaceutically acceptable carriers can be either solid or liquid. Solid form preparations include powders, tablets, dispersible granules, capsules, cachets, suppositories, and ointments. A solid carrier can be one or more substances which may also act as diluents, flavouring agents, solubilizers, lubricants, suspending agents, binders, or tablets disintegrating agents; it can also be as finely divided solid which is in admixture with the finely divided active compound. For the preparation of tablets, the active compound is mixed with carrier having the necessary binding properties in suitable proportions and compacted in the shape and size desired. The powders and tablets preferably contain from about 5 to about 70 percent of the active ingredient. Suitable solid carriers are lactose, pectin, dextrin, starch, gelatin, tragacanth, low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, capsules can be used as solid dosage forms suitable for oral administration.

Liquid form preparations include solutions, suspensions, and emulsions. As an example may be mentioned water or water-propylene glycol solutions for parenteral injection. Such solutions are prepared so as to be acceptable to biological systems (isotonicity, pH, etc.). Liquid preparations can also be formulated in solution in aqueous polyethylene glycol solution. Aqueous solutions suitable for oral use can be prepared by dissolving the active component in water and adding suitable colorants, flavours, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Ointment preparations contain heavy metal salts of a compound of Formula I with a physiologically acceptable carrier. The carrier is desirably a conventional water-dispersible hydrophilic or oil-in-water carrier, particularly a conventional semi-soft or cream-like water-dispersible or water soluble, oil-in-water emulsion infected surface with a minimum of discomfort. Suitable compositions may be prepared by merely incorporating or homogeneously admixing finely divided compounds with the hydrophilic carrier or base or ointment.

Preferably, the pharmaceutical preparation is in unit dosage form. In such form, the preparation is subdivided into unit doses containing appropriate quantities of the active component. The unit dosage form can be a packaged preparation, the package containing discrete capsules, powders in vials or ampoules, and ointments capsule, cachet, tablet, gel, or cream itself or it can be the appropriate number of any of these packaged forms.

The quantity of active compound in a unit dose of preparation may be varied or adjusted from less than 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. The dosages, however, may be varied depending upon the requirements of the patient and the compound being employed. Determination of the proper dosage for a particular situation is within the smaller dosages which are less than the optimum dose. Small increments until the optimum effect under the daily dosage may be divided and administered in portions during the day if desired.

In order to achieve the above mentioned objects in accordance with the purpose of the invention as embodied and broadly described herein, there are provided process for the synthesis of compounds of Formulae I, II, III and IV. Pharmaceutically acceptable non-toxic acid addition salts of the compounds of the present invention of Formulae I, II, III and IV may be formed with inorganic or organic acids, by methods well known in the art.

The present invention also includes within its scope prodrugs of the compounds of Formulae I, II, III and IV. In general, such prodrugs will be functional derivatives of these compounds which readily get converted in vivo into defined compounds. Conventional procedures for the selection and preparation of suitable prodrugs are known.

The invention also includes pharmaceutically acceptable salts, the enantiomers, diastereomers, N-oxides, prodrugs, metabolites in combination with pharmaceutically acceptable carrier and optionally included excipient.

Other objects and advantages of the invention will be set forth in the description which follows, and in part will be apparent from the description, or may be learned by the practice of the invention. The objects and the advantages of the invention may be released and obtained by means of the mechanism and combination pointed out in the appended claims.

DETAILED DESCRIPTION OF THE INVENTION

The compounds of the present invention may be prepared by following the reaction sequences as depicted in the schemes defined below.

Mainly five different amines of Formula V

FORMULA V

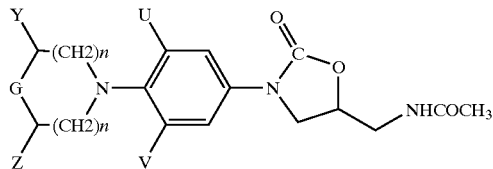

identified as five different cores, namely

-(S)-N-[[3-[3-Fluoro-4-(N-piperazinyl)phenyl]-2-oxo-5-oxazolidinyl]methyl]acetamide (core I);

-(S)-N-[[3-[3-Fluoro[4-[3-(1α,5α,6α)-6-[N-methyl] amino]-3-azabicyclo-[3.1.0]hexane]phenyl]-2-oxo-5-oxazolidinyl]methyl]acetamide (core II);

-(S)-N-[[3-[3-Fluoro[4-[3-(1α,5α,6α)-6-[N-methyl] amino methyl]-3-azabicyclo-[3.1.0]hexane]phenyl]-2-oxo-5-oxazolidinyl]methyl]acetamide (core III);

-(S)-N-[[3-[4-[4-N-methylaminopiperidin-1-yl]-3-fluorophenyl}-2-oxo-oxazolidin-5-yl]methyl acetamide (core IV); and, -(S)-N-[[3-[3[Fluoro-4-(N-1-homopiperazinyl)phenyl]-2-oxo-5-oxazolidinyl]-methyl]acetamide (core V), were used for analoguing purposes.

Key intermediate amines of Formula V for the analogue preparation were prepared from commercially available reagents wherein G in amines of Formula V is defined as NH, CH(NHR), —CH—CH$_2$NHR wherein R is H, ethyl, methyl, isopropyl, acetyl, cyclopropyl, alkoxy, or acetyl and U, V, Y and Z are as defined for Formula II. Some amines of Formula V are already known in the literature and are given by reference and if they have been made for the first time or by a different procedures or variation of known procedure they are described in detail in the experimental section.

Optically pure amines of Formula V could be obtained either by one of a number of asymmetric syntheses or alternatively by resolution from a racemic mixture by selective crystallization of a salt prepared, with an appropriate optically active acid such as dibenzoyl tartrate or 10-camphorsulfonic acid, followed by treatment with base to afford the optically pure amine.

The compounds of the present invention represented by general Formula I may be prepared by the method of reaction in Scheme I:

SCHEME-I

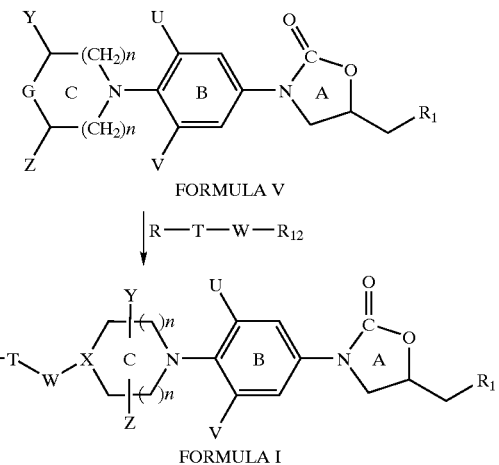

In Scheme I, the heteroaromatic group with the corresponding appendage can be introduced on the nitrogen atom of ring C of compounds of Formula V by one of the methods described below to given Formula I, wherein R$_{12}$ is a suitable leaving group well known to one of ordinary skill in the art such as fluoro, chloro, bromo, SCH$_3$, —SO$_2$CH$_3$, —SO$_2$CF$_3$ or OC$_6$H$_5$ etc. and G in amines of Formula V is defined as NH, CH(NHR$_{13}$), —CH—CH$_2$NHR$_{13}$ wherein R$_{13}$ is H, ethyl, methyl, isopropyl,acetyl, cyclopropyl, alkoxy or acetyl U, V, Y and Z are as defined for Formula I earlier.

Amine of structure of Formula V is reacted with a heteroaromatic compound of Formula R-T-W—R$_{12}$ wherein R, T, W are the same as defined for Formula I earlier. For the preparation of compounds of Formula I when W is equal to CH$_2$ corresponding aldehyde can be used through a process of reductive amination and is attached to amine of Formula V.

Similarly, for the preparation of compound of Formula I wherein W is equal to C=O corresponding acid can be used and the amino of Formula V can be acylated through activated esters in the presence of condensing agents such as 1,3-dicyclohexylcarbodiimide (DCC) and 1-(3-dimethylaminopropyl)-3-ethylcarbodiimide (EDC). Other methods of acylation can also be employed.

Alternatively, the compounds having carbonyl link can also be made by reacting heteroaromatic compound of the Formula VI

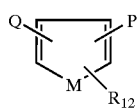

FORMULA VI such as N-methyl pyrrole with the intermediate amine of Formula V in the presence of triphosgene or phosgene. Carbonyl linkers may also be introduced between heteroaromatic compound such as 3-bromothiophene and amine of Formula V with carbon monoxide and the catalyst such as Pd $(PPh_3)_2Cl_2$. Extended chain pyrroles having dicarbonyl linkers can also be obtained from treatment with oxalyl chloride and amine of the Formula V.

The reduction of the carbonyl linkers using the standard reducing agents results in the formation of methylene linkers.

Preparation of the compound of Formula I as represented by Formula II (where heterocycle is 5 membered ring) is accomplished as exemplified below by three methods A, B and C as shown in Scheme II:

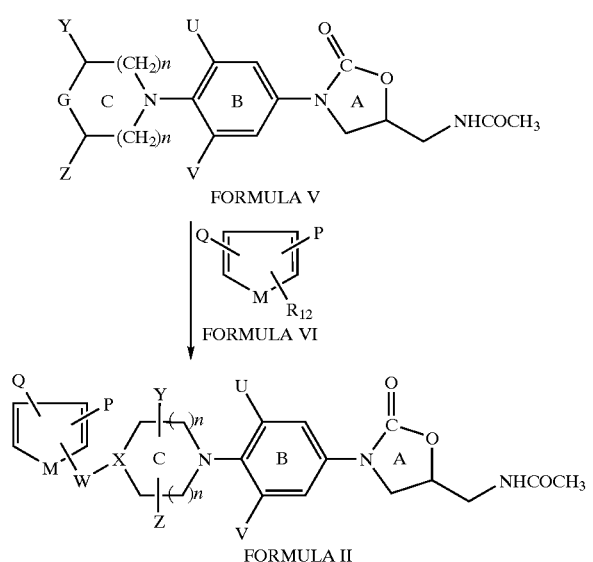

SCHEME-II

FORMULA V

FORMULA VI

FORMULA II

Method A:
Amine of structure V is reacted with a heteroaromatic compound of Formula VI having $R_{12}$ as a suitable leaving group defined earlier for Scheme I. Q, P and M are as defined for Formula II.

The reaction is done in a suitable solvent such as dimethylformamide, dimethylacetamide, ethanol or ethylene glycol at a suitable temperature in the range of $-70°$ C. to $180°$ C. to afford compounds of Formula I. The presence of a suitable base such as triethylamine, diisopropyl amine, potassium carbonate, sodium bicarbonate is useful in some cases to improve the yield of the reaction.

Method B:
Reductive alkylation of the amine intermediate of Formula V, with the corresponding heterocyclic aldehydes of the Formula VI, such as furaldehyde (Q, P=H, M=O; $R_{12}$ is CHO) using known reducing agents well known to one of ordinary skill in the art such as sodium triacetoxyborohydride or sodium cyanoborohydride gave the products of Formula II wherein W=$CH_2$ as shown in the Scheme II.

Method C:
Acylation of intermediate amines of Formula V with heterocyclic acid of Formula VI, such as 2-furoic acid (Q,P=H; M=O, $R_{12}$=COOH) gave products of Formula II, wherein W=CO, as shown in the Scheme II wherein U, V, Y, Z, X, W, M, P, Q and $R_{12}$ are the same.
-(S)-N[[3-[3-Fluoro-4-[N-1[4-(5-nitro-2-thienoyl)] piperazinyl]phenyl]2-oxo-5-oxazolidinyl]methyl] acetamide hydrochloride was prepared using this method.

The reduction of the carbonyl linkers using the standard reducing agents results in the formation of methylene linkers.

SCHEME-III

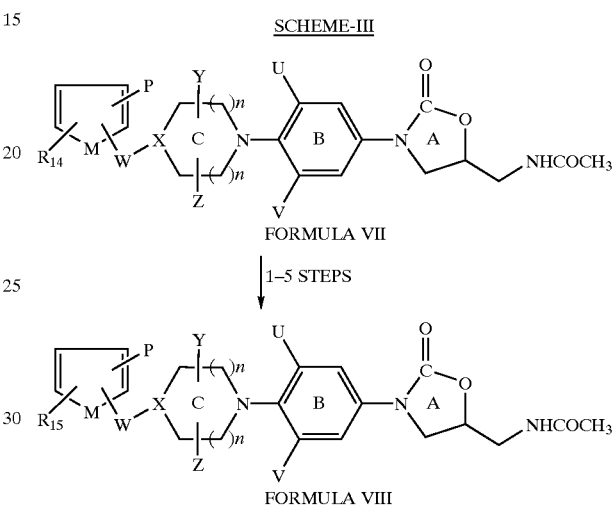

FORMULA VII

1–5 STEPS

FORMULA VIII

The compounds prepared by Scheme I represented by Formula VII

FORMULA VII

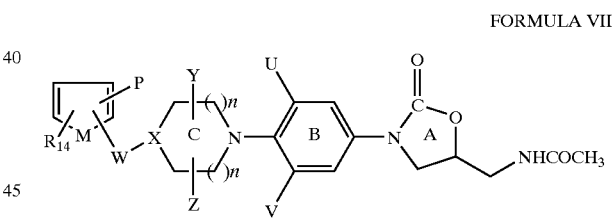

were further used as starting compounds for further derivatisation as represented by Scheme III wherein U,V,Y,Z,X, W,P,Q, n and M are the same as defined earlier. The group $R_{14}$ was transformed in one to five steps into final compounds of Formula VIII

FORMULA VIII

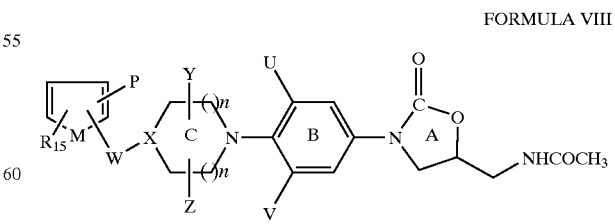

wherein U,V,Y,Z, n, X,W,P and M are the same as defined earlier containing transformed group $R_{15}$. In most cases the $R_{14}$ group in starting compounds were compounds containing $R_{14}$ as aldehyde and ketones.

The following compounds are exemplified in Scheme-IIIA, IIIB and IIIC.

SCHEME-III A

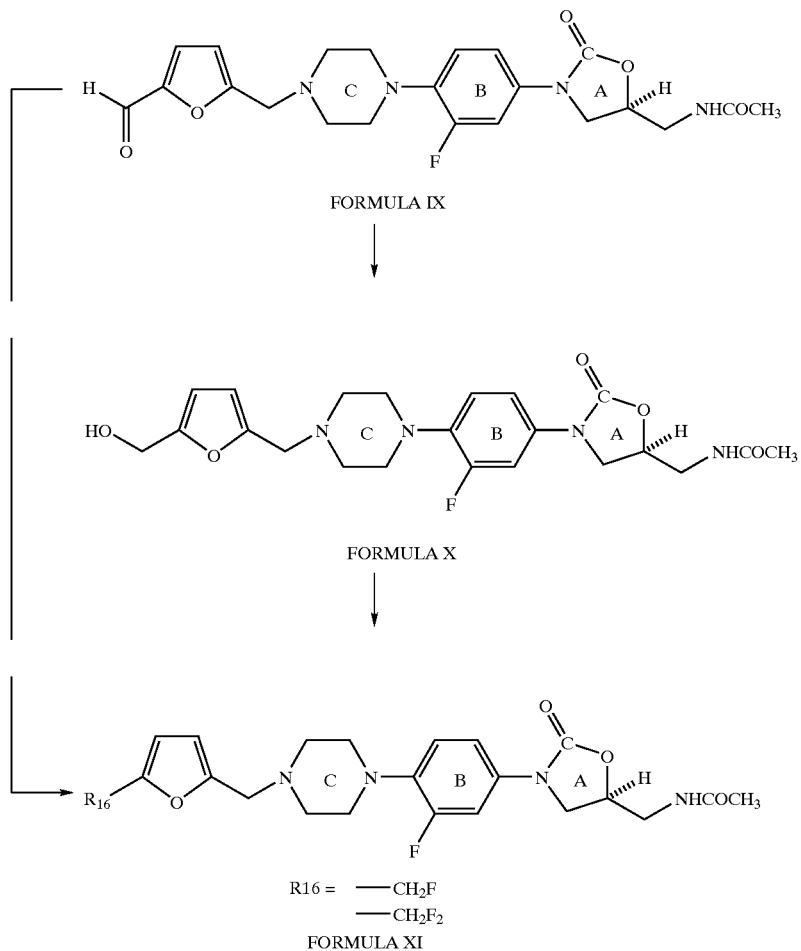

FORMULA IX

FORMULA X

R16 = —CH₂F
—CH₂F₂
FORMULA XI (S)-N-[[3-[3-Fluoro-4-[N-1{2-furyl-[4-(5-hydroxymethyl)methyl}]piperazinyl]-2-oxo-5-oxazolidinyl]methyl]acetamide represented by Formula X was prepared by reducing aldehyde of Formula IX with sodium borohydride.

(S)-N-[[3-[3-fluoro-4-[N-1{2-furyl-[4-(5-fluoromethyl)methyl}]piperazinyl]-2-oxo-5-oxazolidinyl]-methyl] acetamide of Formula XI ($R_{16}$=CH₂F) was prepared by reacting (S)-N-[[3-[3-Fluoro-4-[N-1{2-furyl-[4-(5-hydroxymethyl)methyl}]piperazinyl]-2-oxo-5-oxazolidinyl]methyl]acetamide by reacting Formula X with diethylamino sulfurtrifluoride.

(S)-N-[[3-[3-fluoro-4-[N-1{2-furyl-[4-(5-difluoromethyl)methyl}]piperazinyl]-2-oxo-5-oxazolidinyl]-methyl]acetamide of Formula XI ($R_{16}$=CH₂F₂) was prepared by reacting (S)-N-[[3-Fluoro-4-[N-1[4-{2-furyl(5-formyl)methyl}]piperazinyl]phenyl]-2-oxo-5-oxazolidinyl]methyl]acetamide of Formula IX with diethylamino sulfurtrifluoride as shown in Scheme IIIA.

SCHEME-IIIB

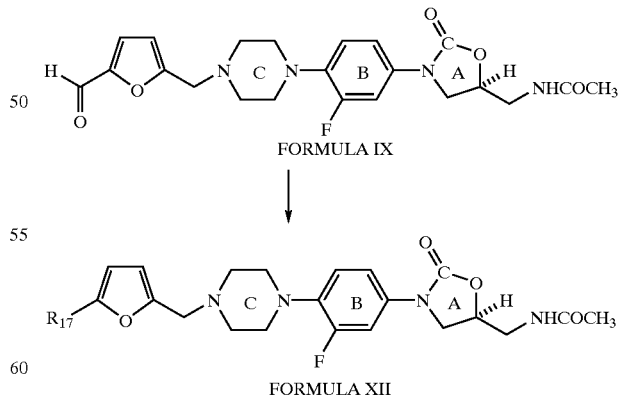

FORMULA IX

FORMULA XII (S)-N-[[3-Fluoro-4-[N-1[4-{2-furyl(5-formyl)methyl}]piperazinyl]phenyl]-2-oxo-5-oxazolidinyl]methyl]acetamide of Formula IX was reacted with hydroxylamine and hydrazine hydrate to give (S)-N-[[3-[3-Fluoro-4-[N-1-

[4-(2-furyl-(5-aldoxime)methyl}]piperazinyl]phenyl]-2-oxo-5-oxazolidinyl]methyl]acetamide of Formula XII

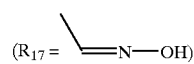

and (S)-N-[[3-[3-Fluoro-4[N-1-[4-{2-furyl-(5-hydrazone)-methyl}]-piperazinyl]-phenyl]-2-oxo-5-oxazolidinyl]-methyl]acetamide of Formula XII

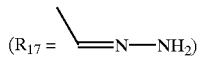

(S)-N-[[3-[3-Fluoro-4-[N-1[4-{2-furyl(5-aldoxime (methyl-4-(N-carboxyaminophenyl acetate)methyl}] piperazinyl]phenyl]-2-oxo-5-oxazolidinyl]-methyl] acetamide of Formula XII

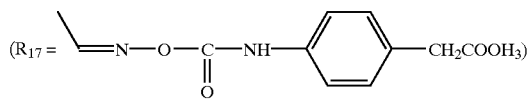

was made starting from (S)-N-[[3-[3-Fluoro-4-[N-1-[4-(2-furyl-(5-aldoxime)methyl}]piperazinyl]phenyl]-2-oxo-5-oxazolidinyl]methyl]acetamide of Formula XII

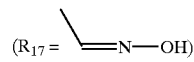

and reacting with isocyanate.

(S)-N-[[3-[3-Fluoro-4-[N-1[4-{2-furyl(5-cyano)methyl}] piperazinyl]phenyl]-2-oxo-5-oxazolidinyl]methyl] acetamide of Formula XII ($R_{17}$=CN) was prepared from (S)-N-[[3-[3-Fluoro-4-[N-1[4-{2-furyl(5-aldoxime) methyl}]piperazinyl]phenyl]-2-oxo-5-oxazolidinyl]methyl] acetamide of Formula XII

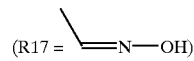

by the use of triflic anhydride and triethylamine.

(S)-N-[[3-Fluoro-4-[N-1[5-(1,3-dioxane)-2-furylmethyl] piperazinyl]phenyl]-2-oxo-5-oxazolidinyl]methyl] acetamide of Formula XII

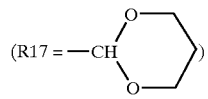

was made using (S)-N-[[3-Fluoro-4-[N-1[4-{2-furyl(5-formyl)methyl}]piperazinyl]phenyl]-2-oxo-5-oxazolidinyl] methyl]acetamide of Formula IX with 1,3-propane diol and $BF_3$ etherate.

SCHEME-IIIC

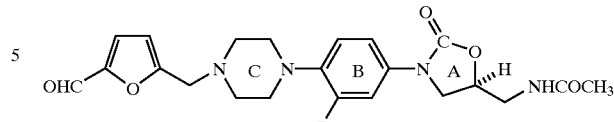

FORMULA IX

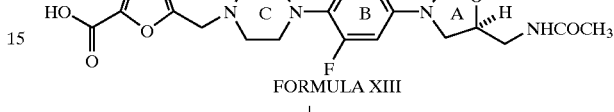

FORMULA XIII

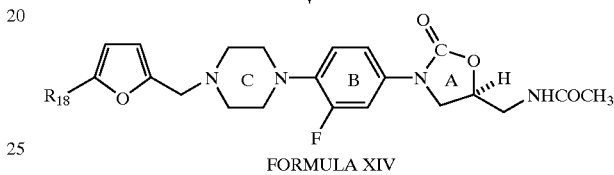

FORMULA XIV

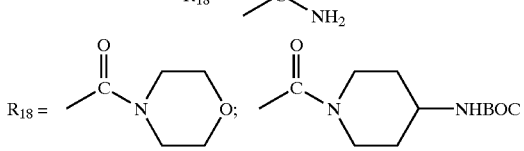

(S)-N-[[3-Fluoro-4-[N-1[4-{2-furyl(5-carboxy)methyl}] piperazinyl]phenyl]-2-oxo-5-oxazolidinyl]methyl] acetamide of Formula XIII was made using (S)-N-[[3-Fluoro-4-[N-1[4-{2-furyl(5-formyl)methyl}]piperazinyl] phenyl]-2-oxo-5-oxazolidinyl]methyl]acetamide of Formula IX by oxidation with $Ag_2O$.

[[3-Fluoro-4-[N-1[5-(formamido)-2-furylmethyl] piperazinyl]phenyl]-2-oxo-5-oxazolidinyl]methyl] acetamide of Formula XIV

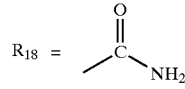

was made by reacting (S)-N-[[3-Fluoro-4-[N-1[4-(2-furyl-(5-carboxyethyl)methyl)piperazinyl]phenyl]-2-oxo-5-oxazolidinyl]methyl]acetamide with aqueous ammonia.

(S)-N-[[3-Fluoro-4-[N-1[5-(4-(tert butoxy carbonyl) amino piperidine)-2-furylmethyl]piperazinyl]phenyl]-2-oxo-5-oxazolidinyl]methyl]acetamide of Formula XIV

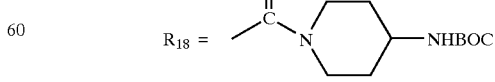

was made by reacting (S)-N-[[3-Fluoro-4-[N-1[4-(2-furyl-(5-carboxy)methyl)piperazinyl]phenyl]-2-oxo-5-oxazolidinyl]methyl]acetamide of Formula XIII with thionyl chloride and 4-(tert butoxy carbonyl)amino piperidine.

(S)-N-[[3-Fluoro-4-[N-1[5-(morpholine-1-carbonyl)-2-furylmethyl]-piperazinyl]phenyl]-2-oxo-5-oxazolidinyl]methyl]acetamide of Formula XIV

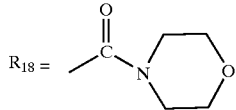

was made by reacting (S)-N-[[3-Fluoro-4-[N-1[4-(2-furyl-(5-carboxy)methyl)piperazinyl]phenyl]-2-oxo-5-oxazolidinyl]methyl]acetamide of Formula XIII with morpholine in the presence of oxalyl chloride.

The transformations effected are described in the experimental section. In the above synthetic methods where specific acids, bases, solvents, catalysts, oxidising agents, reducing agents etc. are mentioned, it is to be understood that the other acids, bases, solvents, catalysts, oxidising agents, reducing agents etc. may be used. Similarly, the reduction temperature and duration of the reaction may be adjusted according to the need. An illustrative list of particular compounds according to the invention and capable of being produced by the above mentioned schemes include:

| Compound No. | Chemical Name |
|---|---|
| 1. | (S)—N-[[3-[3-Fluoro-4-[N-1-[4-(2-furoyl)piperazinyl]]phenyl]-2-oxo-5-oxazolidinyl]methyl]acetamide |
| 2. | (S)—N-[[3-[3-Fluoro-4-[N-1[4-{2-furyl(5-formyl)methyl}]piperazinyl]phenyl]-2-oxo-5-oxazolidinyl]methyl]acetamide |
| 3. | (S)—N-[[3-Fluoro-4-[N-1[4-(2-furyl-(5-carboxyethyl)methyl)piperazinyl]phenyl]-2-oxo-5-oxazolidinyl]methyl]acetamide |
| 4. | (S)—N-[[3-Fluoro-4-[N-1[4-(5-bromo-2-furoyl)]piperazinyl]phenyl]-2-oxo-5-oxazolidinyl]methyl]acetamide |
| 5. | (S)—N-[[3-Fluoro-4-[N-1[4-(5-chloromethyl-2-furoyl)piperazinyl]phenyl]-2-oxo-5-oxazolidinyl]methyl]acetamide |
| 6. | (S)—N-[[3-Fluoro-4-[N-1[4-(5-nitro-2-furoyl)piperazinyl]phenyl]-2-oxo-5-oxazolidinyl]methyl]acetamide |
| 7. | (S)—N[[3-[3-Fluoro-4-[N-1[4-{2-(2-thienyl)dicarbonyl}]piperazinyl]phenyl]2-oxo-5-oxazolidinyl]methyl]acetamide |
| 8. | (S)—N[[3-[3-Fluoro-4-[N-1[4-(3-furoyl)]piperazinyl]phenyl]2-oxo-5-oxazolidinyl]methyl]acetamide |
| 9. | (S)—N[[3-[3-Fluoro-4-[N-1[4-{2-furyl(5-bromo)methyl}]piperazinyl]phenyl]2-oxo-5-oxazolidinyl]methyl]acetamide |
| 10. | (S)—N[[3-[3-Fluoro-4-[N-1[4-{2-thienyl(5-chloro)methyl}]piperazinyl]phenyl]2-oxo-5-oxazolidinyl]methyl]acetamide |
| 11. | (S)—N[[3-[3-Fluoro-4-[N-1[4-(2-furylmethyl))piperazinyl]phenyl]2-oxo-5-oxazolidinyl]methyl]acetamide |
| 12. | (S)—N-[[3-[3-Fluoro-4-[N-1[4-(2-thienylmethyl)]piperazinyl]phenyl]-2-oxo-5-oxazolidinyl]methyl]acetamide |
| 13. | (S)—N[[3-[3-Fluoro-4-[N-1[4-(2-thienylacetyl)]piperazinyl]phenyl]2-oxo-5-oxazolidinyl]methyl]acetamide |
| 14. | (S)—N-[[3-[3-Fluoro-4-[N-1[4-{2-thienyl(4-bromo)methyl}]piperazinyl]phenyl]-2-oxo-5-oxazolidinyl]methyl]acetamide |
| 15. | (S)—N-[[3-[3-fluoro-4-[N-1-[4-{2-furyl-(5-nitro)methyl}]piperazinyl]phenyl]-2-oxo-5-oxazolidinyl]methyl]acetamide |
| 16. | Hydrochloric salt of (S)—N-[[3-Fluoro-4-[N-1[4-{2-furyl(5-nitro)methyl}]-piperazinyl]phenyl]-2-oxo-5-oxazolidinyl]methyl]acetamide |
| 17. | Citrate slat of (S)—N-[[3-Fluoro-4-[N-1[4-{2-furyl(5-nitro)methyl}]piperazinyl]phenyl]-2-oxo-5-oxazolidinyl]methyl]acetamide |
| 18. | (S)—N[[3-[3-Fluoro-4-[N-1[4-(2-pyrrolylmethyl)piperazinyl]phenyl]2-oxo-5-oxazolidinyl]methyl]acetamide |
| 19. | (S)—N[[3-[3-Fluoro-4-[N-1[4-{2-thienyl(3-methyl)methyl}]piperazinyl]phenyl]2-oxo-5-oxazolidinyl]methyl]acetamide |
| 20. | (S)—N[[3-[3-Fluoro-4-[N-1[4-(3-furylmethyl))piperazinyl]phenyl]2-oxo-5-oxazolidinyl]methyl]acetamide |
| 21. | (S)—N[[3-[3-Fluoro-4-[N-1[4-{2-thienyl(5-methyl)methyl}]piperazinyl]phenyl]2-oxo-5-oxazolidinyl]methyl]acetamide |
| 22. | (S)—N[[3-[3-Fluoro-4-[N-1[4-{2-pyrrole(1-methyl)methyl}]piperazinyl]phenyl]2-oxo-5-oxazolidinyl]methyl]acetamide |
| 23. | (S)—N[[3-[3-Fluoro-4-[N-1[4-{2-thienyl(5-nitro)methyl}]piperazinyl]phenyl]2-oxo-5-oxazolidinyl]methyl]acetamide |
| 24. | (S)—N[[3-[3-Fluoro-4-[N-1[4-[2-furyl{5-(N-thiomorpholinyl)methyl}methyl]-piperazinyl]phenyl]2-oxo-5-oxazolidinyl]methyl]acetamide |
| 25. | (S)—N[[3-[3-Fluoro-4-[N-1[4-[2-furyl{5-(N-morpholinyl)methyl}methyl]]piperazinyl]phenyl]2-oxo-5-oxazolidinyl]methyl]acetamide |
| 26. | (S)—N-[[3-Fluoro-4-[N-1[4-{2-furyl(5-acetoxymethyl)methyl}]piperazinyl]phenyl]-2-oxo-5-oxazolidinyl]methyl]acetamide |
| 27. | (S)—N-[[3-Fluoro-4-[N-1[4-{2-thienyl(5-bromo)methyl}]piperazinyl]phenyl]-2-oxo-5-oxazolidinyl]methyl]acetamide |
| 28. | (S)—N-[[3-Fluoro-4-[N-1[4-(5-nitro-2-furylmethyl)piperazinyl]phenyl]-2-oxo-oxazolidinyl]methyl]dichloroacetamide |
| 29. | (S)—N[[3-[3-Fluoro-4-[N-1[4-(5-nitro-2-thienoyl)]piperazinyl]phenyl]2-oxo-5-oxazolidinyl]methyl]acetamide hydrochloride |

-continued

| Compound No. | Chemical Name |
|---|---|
| 30. | (S)—N[[3-[3-Fluoro-4-[N-1[4-(2',2'-diphenyl-2'-hydroxyacetyl)]piperazinyl]phenyl]2-oxo-5-oxazolidinyl]methyl]acetamide |
| 31. | (S)—N-[[3-[3-Fluoro[4-[3-(1α,5α,6α)-6-[N-(5-nitro-2-furoyl)-N-methyl]amino]-3-azabicyclo-[3.1.0]hexane]phenyl]-2-oxo-5-oxazolidinyl]methyl]acetamide |
| 32. | (S)—N-[[3-[3-Fluoro[4-[3-(1α,5α,6α)-6-[N-(3-furoyl)-N-methyl]amino]-3-azabicyclo-[3.1.0]hexane]phenyl]-2-oxo-5-oxazolidinyl]methyl]acetamide |
| 33. | (S)—N-[[3-[3-Fluoro[4-[3-(1α,5α,6α)-6-[N-(5-bromo-2-furoyl)-N-methyl]amino]-3-azabicyclo-[3.1.0]hexane]phenyl]-2-oxo-5-oxazolidinyl]methyl]acetamide |
| 34. | (S)—N-[[3-[3-Fluoro[4-[3-(1α,5α,6α)-6-[N-(5-nitro-2-thienylmethyl)-N-methyl]-amino]-3-azabicyclo-[3.1.0]hexane]phenyl]-2-oxo-5-oxazolidinyl]methyl]acetamide |
| 35. | (S)—N-[[3-[3-Fluoro[4-[3-(1α,5α,6α)-6-[N-(5-nitro-2-furylmethyl)-N-methyl]amino]-3-azabicyclo-[3.1.0]hexane]phenyl]-2-oxo-5-oxazolidinyl]methyl]acetamide |
| 36. | (S)—N-[[3-[3-Fluoro[4-[3-(1α,5α,6α)-6-[N-(5-formyl-2-furylmethyl)-N-methyl]amino-methyl]-3-azabicyclo-[3.1.0]hexane]phenyl]-2-oxo-5-oxazolidinyl]methyl]acetamide |
| 37. | (S)—N-[[3-[3-Fluoro[4-[3-(1α,5α,6α)-6-[N-(5-carboxyethyl-2-furylmethyl)-N-methyl]aminomethyl]-3-azabicyclo-[3.1.0]hexane]phenyl]-2-oxo-5-oxazolidinyl]methyl]acetamide |
| 38. | (S)—N-[[3-[3-Fluoro[4-[3-(1α,5α,6α)-6-[N-(2-thiopheneacetyl)-N-methyl]amino-methyl]-3-azabicyclo-[3.1.0]hexane]phenyl]-2-oxo-5-oxazolidinyl]methyl]acetamide |
| 39. | (S)—N-[[3-[3-Fluoro[4-[3-(1α,5α,6α)-6-[N-(5-nitro-2-thienylmethyl)-N-methyl]-amino-methyl]-3-azabicyclo-[3.1.0]hexane]phenyl]-2-oxo-5-oxazolidinyl]methyl]acetamide |
| 40. | (S)—N-[[3-[3-Fluoro[4-[3-(1α,5α,6α)-6-[N-(5-nitro-2-furylmethyl)-N-methyl]amino-methyl]-3-azabicyclo-[3.1.0]hexane]phenyl]-2-oxo-5-oxazolidinyl]methyl]acetamide |
| 41. | (S)—N-[[3-[4-[4-(N-methyl-N-2furyl(5formyl)methylaminopiperidine-1-yl]-3-fluorophenyl]-2-oxo-oxazolidin-5-yl]methyl]acetamide |
| 42. | (S)—N-[[3-[4-[4-(N-methyl-N-(3,5-difluorobenzoyl)aminopiperidine-1-yl]-3-fluorophenyl]-2-oxo-oxazolidin-5-yl]methyl]acetamide |
| 43. | (S)—N-[[3-[4-[4-(N-methyl-N-(5-bromo-2-furoyl)aminopiperidine-1-yl]-3-fluorophenyl]-2-oxo-oxazolidin-5-yl]methyl]acetamide |
| 44. | (S)—N-[[3-[4-[4-(N-methyl-N-(5-nitro-2-furoyl)aminopiperidine-1-yl]-3-fluorophenyl]-2-oxo-oxazolidin-5-yl]methyl]acetamide |
| 45. | (S)—N-[[3-[4-[4-(N-methyl-N-3-furoyl)aminopiperidine-1-yl]-3-fluorophenyl]-2-oxo-oxazolidin-5-yl]methyl]acetamide |
| 46. | (S)—N-{3-[4-[4-(N-methyl, N-2-furoyl)aminopiperidine-1-yl]-3-fluorophenyl]-2-oxo-oxazolidin-5-yl methyl]acetamide |
| 47. | (S)—N-{3-[4-[4-(N-methyl,2-thiopheneacetyl)aminopiperidine-1-yl]-3-fluorophenyl]-2-oxo oxazolidin-5-yl methyl]acetamide |
| 48. | (S)—N-[[3-[4-[4-(N-methyl-N-2furylmethyl) aminopiperidine-1-yl]-3-fluorophenyl]-2-oxo-oxazolidin-5-yl]methyl]acetamide |
| 49. | (S)—N-[[3-[4-[4-(N-methyl-N-3-furyl)aminopiperidine-1-yl]-3-fluorophenyl]-2-oxo-oxazolidin-5-yl]methyl]acetamide |
| 50. | (S)—N-[[3-[4-[4-(N-methyl-N-2-furyl(5-nitro)methyl)aminopiperidine-1-yl]-3-fluorophenyl]-2-oxo-oxazolidin-5-yl]methyl]acetamide |
| 51. | (S)—N-[[3-[4-[4-(N-methyl-N-2-thienyl(5-nitro)methyl)aminopiperidine-1-yl]-3-fluorophenyl]-2-oxo-oxazolidin-5-yl]methyl]acetamide |
| 52. | (S)—N-[[3-[4-[4-(N-methyl-N-2-thienylmethyl)aminopiperidine-1-yl]-3-fluorophenyl]-2-oxo-oxazolidin-5-yl]methyl]acetamide |
| 53. | (S)—N-[[3-[4-[4-(N-methyl-N-(5-methyl-2-thienylmethyl)aminopiperidine-1-yl]-3-fluorophenyl]-2-oxo-oxazolidin-5-yl]methyl]acetamide |
| 54. | (S)—N-{3-[4-[4-(N-methyl,2-(5-bromo)thienylmethyl)aminopiperidine-1-yl]-3-fluorophenyl]-2-oxo-oxazolidin-5-yl methyl]acetamide |
| 55. | (S)—N[[3-[3-Fluoro-4-[N-1[4-{2-furyl(5-formyl)methyl}]homopiperazinyl]phenyl]2-oxo-5-oxazolidinyl]methyl]acetamide |
| 56. | (S)—N[[3-[3-Fluoro-4-[N-1[4-(2-thienylacetyl)]homopiperazinyl]phenyl]2-oxo-5-oxazolidinyl]methyl]acetamide |
| 57. | (S)—N[[3-[3-Fluoro-4-[N-1[4-{2-thienyl(5-nitro)methyl}]homopiperazinyl]phenyl]2-oxo-5-oxazolidinyl]methyl]acetamide |
| 58. | (S)—N[[3-[3-Fluoro-4-[N-1[4-(3-furylmethyl)]homopiperazinyl]phenyl]2-oxo-5-oxazolidinyl]methyl]acetamide |
| 59. | (S)—N-[[3-[3-fluoro-4-[N-1{2-furyl-[4-(5-difluoromethyl)methyl}]piperazinyl]-2-oxo-5-oxazolidinyl]-methyl]acetamide |
| 60. | (S)—N-[[3-[3-Fluoro-4-[N-1-[4-(2-furyl-(5-aldoxime)methyl}]piperazinyl]phenyl]-2-oxo-5-oxazolidinyl]methyl]acetamide |
| 61. | (S)—N-[[3-[3-Fluoro-4-[N-1[4-{2-furyl(5-aldoxime(methyl-4-(N-carboxyaminophenyl acetate) methyl}]piperazinyl]phenyl]-2-oxo-5-oxazolidinyl]methyl]acetamide |
| 62. | (S)—N-[[3-[3-Fluoro-4[N-1-[4-{2-furyl-(5-hydrazone)-methyl}]-piperazinyl]-phenyl]-2-oxo-5-oxazolidinyl]-methyl]acetamide |
| 63. | (S)—N-[[3-[3-Fluoro-4-[N-1-{2-furyl-[4-(5-hydroxymethyl)methyl}]piperazinyl]-2-oxo-5-oxazolidinyl]methyl]acetamide |

-continued

| Compound No. | Chemical Name |
|---|---|
| 64. | (S)—N-[[3-[3-Fluoro-4-[N-1[4-{2-furyl(5-cyano)methyl}]piperazinyl]phenyl]-2-oxo-5-oxazolidinyl]methyl]acetamide |
| 65. | (S)—N-[[3-Fluoro-4-[N-1[4-{2-furyl(5-carboxy)methyl}]piperazinyl]phenyl]-2-oxo-5-oxazolidinyl]methyl]acetamide |
| 66. | (S)—N-[[3-Fluoro-4-[N-1[5-(1,3-dioxane)-2-furylmethyl]piperazinyl]phenyl]-2-oxo-5-oxazolidinyl]methyl]acetamide |
| 67. | (S)—N-[[3-Fluoro-4-[N-1[5-(formamido)-2-furylmethyl]piperazinyl]phenyl]-2-oxo-5-oxazolidinyl]methyl]acetamide |
| 68. | (S)—N-[[3-Fluoro-4-[N-1[5-(morpholine-1-carbonyl)-2-furylmethyl]piperazinyl]-phenyl]-2-oxo-5-oxazolidinyl]methyl]acetamide |
| 69. | (S)—N-[[3-Fluoro-4-[N-1[5-(4-(tert butoxy carbonyl)amino piperidine)-2-furyl-methyl]piperazinyl]phenyl]-2-oxo-5-oxazolidinyl]methyl]acetamide |
| 70. | (S)—N-[[3-Fluoro-4-[N-1[4-{(Z)-2-methoxyimino-2-(2-furyl)acetyl}]piperazinyl]-phenyl]-2-oxo-5-oxazolidinyl]methyl]acetamide |
| 71. | (S)—N-[[3-[3-Fluoro[4-[3-(1α, 5α, 6α)-6-[N-(2-thiopheneacetyl)-N-methyl]amino]-3-azabicyclo-[3.1.0]hexane]phenyl]-2-oxo-5-oxazolidinyl]methyl]acetamide |
| 72. | (S)—N-[[3-[3-Fluoro[4-[3-(1α, 5α, 6α)-6-[N-(5-formyl-2-furylmethyl)-N-methyl]-amino]-3-azabicyclo-[3.1.0]hexane]phenyl]-2-oxo-5-oxazolidinyl]methyl]acetamide |
| 73. | (S)—N-[[3-[3-Fluoro[4-[3-(1α, 5α, 6α)-6-[N-(3-thienoyl)-N-methyl]amino]-3-aza-bicyclo[3.1.0]hexane]phenyl]-2-oxo-5-oxazolidinyl]methyl]acetamide |
| 74. | (S)—N-[[3-[3-fluoro-4-[N-1{2-furyl-[4-(5-fluoromethyl) methyl}]piperazinyl]-2-oxo-5-oxazolidinyl]-methyl]acetamide |

Pharmacological Testing

The compounds of the invention display antibacterial activity when tested by the agar incorporation method. The following minimum inhibitory concentrations ($\mu$g/ml) were obtained for representative compounds of the invention which are given below in the following tables.

Guide to Table Abbreviations:
1) S.aureus ATCC 25923—Staphylococus aureus ATCC 25923
2) MRSA 15187—Methicillin Resistant Staphylococcus aureus
3) Ent. faecalis ATCC 29212—Enterococcus faecalis ATCC 29212
4) Ent. faecium 6A—Enterococcus faecium 6A Van®, Cipro®
5) Strep. pne. ATCC 6303—Streptococcus pneumoniae ATCC 6303
6) Strep. pyog. ATCC 19615—Streptococcus pyogenes
7) S. epidermidis—Staphylococcus epidermidis ATCC 12228

TABLE 1

MIC of compounds and standard antibiotics against important pathogens

| Compound No. | S. aureus 25923 | MRSA 15187 | MRSA 562 | MRSA 33 | E. faecalis 29212 | VRE 6A | S. pyogenes 19615 | S. pneum 6303 | S. pneum AB 34 |
|---|---|---|---|---|---|---|---|---|---|
| 02 | 1 | 2 | 1 | 2 | 8 | 8 | 8 | 4 | 8 |
| 14 | 4 | 2 | 2 | 2 | 2 | 2 | 2 | 4 | 4 |
| 60 | 2 | 2 |   | 2 | 8 | 16 | 4 | 8 | 8 |
| 66 | 2 | 2 | 2 | 2 | 16 | 16 | 8 | 8 | 8 |
| 12 | 8 | 8 | 8 | 8 | 8 | 8 | 4 | 8 | 8 |
| 62 | 2 | 2 | 1 | 2 | 8 | 8 | 8 | 8 | 8 |
| 61 | 8 | 8 |   | 8 | 8 | 8 | 8 | 8 | 8 |
| 15 | 2 | 2 | 2 | 2 | 2 | 1 | 1 | 1 | 2 |
| 01 | 2 | 2 |   | 4 | 2 | 2 | 1 | 2 | 1 |
| 27 | 2 | 2 | 2 | 2 | 2 | 4 | 1 | 2 | 0.5 |
| 16 | 2 | 4 |   | 4 | 2 | 4 | 0.5 | 1 | 1 |
| 17 | 2 | 2 |   | 2 | 2 | 4 | 1 | 2 | 1 |
| 04 | 2 | 2 |   | 2 | 2 | 1 | 2 | 1 | 1 |
| 05 | 16 | 4 |   | 4 | 8 | 8 | 4 | 4 | 4 |
| 06 | 1 | 0.5 |   | 0.5 | 1 | 1 | 2 | 2 | 2 |
| 10 | 8 | 4 |   | 4 | 8 | 4 | 1 | 4 | 8 |
| 23 | 8 | 8 |   | 8 | 8 | 8 | 1 | 8 | 8 |
| 33 | 4 | 4 |   | 4 | 4 | 4 | 0.5 | 8 | 4 |
| 73 | 8 | 8 |   | 8 | 8 | 8 | 1 | 4 | 8 |
| 72 | 8 | 4 |   | 4 | 8 | 8 | 0.25 | 4 | 4 |
| 32 | 8 | 8 |   | 8 | 8 | 8 | 1 | 4 | 4 |
| 08 | 2 | 1 | 1 | 1 | 1 | 1 | 1 | 2 | 4 |
| 07 | 2 | 2 | 2 | 2 | 2 | 2 | 0.5 | 2 | 2 |
| 34 | 1 | 1 | 1 | 1 | 1 | 1 | 2 | 4 | 4 |
| 71 | 4 | 4 |   | 4 | 4 | 4 | 2 | 4 | 4 |
| 29 | 0.25 | <0.1 | <0.1 | <0.1 | 1 | 0.5 | 1 | 1 | 1 |
| 44 | 0.25 | <0.1 | <0.1 | <0.1 | 0.25 | <0.1 | 0.5 | 2 | 2 |
| 50 | 1 | 1 | 0.5 | 1 | 0.5 | 0.25 | 0.125 | 0.5 | 2 |

TABLE 1-continued

MIC of compounds and standard antibiotics against important pathogens

| Compound No. | S. aureus 25923 | MRSA 15187 | MRSA 562 | MRSA 33 | E. faecalis 29212 | VRE 6A | S. pyogenes 19615 | S. pneum 6303 | S. pneum AB 34 |
|---|---|---|---|---|---|---|---|---|---|
| 40 | 2 | 2 | 1 | 2 | 2 | 4 | 0.125 | NG | 2 |
| 51 | 2 | 1 | 1 | 1 | 4 | 4 | 0.5 | NG | 2 |
| 22 | 2 | 8 | 4 | 8 | 8 | 8 | 1 | 1 | 1 |
| 38 | 4 | 4 | 4 | 4 | 4 | 4 | 1 | 1 | 1 |
| 39 | 8 | 8 | 8 | 4 | 2 | 8 | 0.5 | 0.5 | 0.5 |
| Linezolid | 2 | 1 | 2 | 2 | 2 | 2 | 2 | 2 | 4 |
| Vancomycin | 1 | 0.5 | 0.5 | 0.5 | 4 | >16 | 0.5 | 0.5 | 0.25 |
| Linezolid | 2 | 1 | 2 | 2 | 2 | 2 | 2 | 2 | 4 |
| Vancomycin | 1 | 0.5 | 0.5 | 0.5 | 4 | >16 | 0.5 | 0.5 | 0.25 |

TABLE 2

Summary of in vitro Activity (MIC):

| Bacteria | Number | Vancomycin MIC50 | Vancomycin MIC90 | Linezolid MIC50 | Linezolid MIC90 | Penicillin G MIC50 | Penicillin G MIC90 | Compound No. 29 MIC50 | Compound No. 29 MIC90 | Compound No. 44 MIC50 | Compound No. 44 MIC90 |
|---|---|---|---|---|---|---|---|---|---|---|---|
| G+ve | 49 | 0.5 | 16 | 2 | 4 | 4 | 32 | 1 | 1 | 0.5 | 2 |
| S. aureus | 8 | 1 | 1 | 2 | 4 | — | — | 0.064 | 0.25 | 0.064 | 0.25 |
| E. faecalis | 7 | 16 | 16 | 4 | 16 | — | — | 1 | 1 | 0.064 | 0.25 |
| S. pneumoniae | 19 | 0.5 | 0.5 | 0.5 | 2 | 4 | 32 | 1 | 1 | 1 | 2 |

| Bacteria | Compound no. 15 MIC50 | Compound no. 15 MIC90 | Compound No. 06 MIC50 | Compound No. 06 MIC90 | Compound No. 50 MIC50 | Compound No. 50 MIC90 | Compound No. 40 MIC50 | Compound No. 40 MIC90 |
|---|---|---|---|---|---|---|---|---|
| G+ve | 1 | 2 | 1 | 2 | 1 | 2 | 1 | 2 |
| S. aureus | 2 | 2 | 1 | 1 | 1 | 2 | 2 | 4 |
| E. faecalis | 2 | 2 | 1 | 1 | 0.5 | 1 | 2 | 4 |
| S. pneumoniae | 2 | 4 | 2 | 2 | 1 | 2 | 1 | 1 |

TABLE 3

Geometric Mean of in vitro activity (MIC):

| | Vancomycin | Linezolid | Penicillin G | Compound No. 44 |
|---|---|---|---|---|
| Gram +ve | 0.93 | 1.25 | 0.76 | 0.31 |
| S. aureus | 1 | 2.38 | — | 0.11 |
| E. faecalis | 9.75 | 4 | — | 0.11 |
| S. pneumoniae | 0.39 | 0.60 | 2.16 | 0.96 |

| | Compound No. 15 | Compound No. 06 | Compound No. 50 | Compound No. 40 |
|---|---|---|---|---|
| Gram +ve | 1.08 | 0.79 | 0.72 | 0.93 |
| S. aureus | 1.63 | 0.74 | 1 | 1.83 |
| E. faecalis | 1.6 | 0.92 | 0.42 | 2.38 |
| S. pneumoniae | 1.04 | 1.27 | 1.41 | 0.71 |

TABLE 4

Changes in MIC under different conditions

| Compound No. | Agar MIC | Broth MIC Normal MH broth | Broth MIC +50% Sheep serum |
|---|---|---|---|
| 16 | 2 | 2 | 2 |
| 08 | 1 | 2 | 4 |
| 29 | <0.1 | 0.25 | 0.5 |
| 44 | <0.1 | <0.1 | 0.25 |
| Linezolid | 2 | 1 | 2 |
| Vancomycin | 1 | 1 | 1 |

TABLE 5

Linezolid has 30% protein binding
In vitro and in vivo activity against MRSA 562

| RBx | MIC (μg/ml) | ED50 (mg/kg body weight) PO |
|---|---|---|
| Vancomycin | 0.5 | 8.84 (IV) |
| Linezolid | 2 | 4.56 |
| 67 | 2 | >25 |
| 15 | 2 | 4.33 |
| 04 | | >25 |
| 06 | 1 | >25 |
| 08 | 1 | 25 |
| 71 | 4 | >25 |

TABLE 5-continued

Linezolid has 30% protein binding
In vitro and in vivo activity against MRSA 562

| RBx | MIC ($\mu$g/ml) | ED50 (mg/kg body weight) PO |
|---|---|---|
| 29 | <0.1 | >25 |
| 44 | <0.1 | >25 |
| 50 | 0.5 |  |
| 07 | 2 | >25 |

The in vitro antibacterial activity of the compounds were demonstrated by the agar incorporation method (NCCLS M 7 and M 100-S8 documents). Briefly, the compounds were dissolved in DMSO and doubling dilution of the compounds were incorporated into Meuller Hilton agar before solidification. Inoculum was prepared by suspending 4 to 5 colonies into 5 ml of normal saline solution and adjusting the turbidity to 0.5 Macfarland turbidity standard tables (1.5× $10^8$ CFU/ml), after appropriate dilutions, $10^4$ CFU/spot was transfered into the surface of dried plate and incubated for 18 hours (24 hours for MRSN studies). The concentration showing no growth of the inoculated culture was recorded as the MIC. Appropriate ATCC standard strains were simultaneously tested and result recorded only when the MIC's against standard antibiotics were within the acceptable range.

The compounds of the present invention represented by general Formula I may be prepared by the method of reaction in Scheme I. Key intermediate amines of Formula V for the analogue preparation were prepared by the synthetic procedures described below from commercially available reagents. The compounds of Formula I were made by either Method A, B, or C.

Amines already known in the literature are given by reference and if they have been made by a different procedures they are described in detail.

Mainly five different amines of Formula V identified as five different cores namely (S)-N-[[3-[3-Fluoro-4-(N-piperazinyl)phenyl]-2-oxo-5-oxazolidinyl]methyl]acetamide (core I), (S)-N-[[3-[3-Fluoro[4-[3-(1$\alpha$,5$\alpha$,6$\alpha$)-6-[N-methyl] amino]-3-azabicyclo-[3.1.0]hexane]benzyl]-2-oxo-5-oxazolidinyl]methyl]acetamide (core II), (S)-N-[[3-[3-Fluoro[4-[3-(1a,5a,6a)-6-[N-(5-nitro-2-furylmethyl)-N-methyl]amino]-3-azabicyclo-[3.1.0] hexane]phenyl]-2-oxo-5-oxazolidinyl]methyl]-acetamide (core III), (S)-N-{3-[4-[4-N-methylaminopeperidin-1-yl]-3-fluorophenyl}-2-oxo-oxazolidin-5-yl]methyl acetamide (core IV), and (S)-N-[[3-[3[Fluoro-4-(N-1-homopiperazinyl)phenyl]-2-oxo-5-oxazolidinyl]methyl]acetamide (core V)

are shown in the examples given below.

Most of the compounds were characterized using NMR, IR and were purified by chromatography. Crude products were subjected to column chromatographic purification using silica gel (100–200 or 60–120 mesh) as stationery phase.

The examples mentioned below demonstrate the general synthetic procedure as well as the specific preparation for the preparation for the preferred compound. The examples are given to illustrate the details of the invention and should not be constrained to limit the scope of the present invention.

EXAMPLE 1

Analogues of (S)-N-[[3-[3-Fluoro-4-(N-piperazinyl) phenyl]-2-oxo-5-oxazolidinyl]methyl]acetamide (core I)

The heteroaromatic group with the corresponding appendage can be introduced on the nitrogen atom of ring C of compounds of Formula I by one of the methods described below:

Method-A:
General Procedure:

Amine of structure of Formula V is reacted with a heteroaromatic compounds of Formula VI having corresponding $R_{12}$ appendages such as $-CH_2R_{13}$, $-COR_{13}$ or $-CH(CH_3)R_{13}$ wherein $R_{13}$ is a suitable leaving group well known to one of ordinary skill in the art such as fluoro, chloro, bromo, $SCH_3$, $-SO_2CH_3$, $-SO_2CF_3$ or $OC_6H_5$ etc.

The reaction is done in a suitable solvent such as dimethylformamide, dimethylacetamide, ethanol or ethylene glycol at a suitable temperature in the range of −78° C. to 180° C. to afford compounds of Formula II. The presence of a suitable base such as triethylamine, diisopropyl amine, potassium carbonate, sodium bicarbonate is useful in some cases to improve the yield of the reaction.

The following compounds were made following this method:

Compound No. 01 (S)-N-[[3-[3-Fluoro-4-[N-1-[4-(2-furoyl) piperazinyl]]-phenyl]-2-oxo-5-oxazolidinyl]methyl] acetamide (S)-N-[[3-[3-Fluoro-4-(N-piperazinyl)phenyl]-2-oxo-5-oxazolidinyl]methyl]acetamide prepared by the method given in U.S. Pat. No. 5,700,799 (1.2 g, 3.57 mmol) was dissolved in dry dimethyl formamide (35 ml). To this was added $K_2CO_3$ (2.47 g; 17.87 mmol) and furoyl chloride (0.56 g, 10.68 mmol). The reaction mixture was stirred at 25° C. for 5.0 hr. TLC of the reaction mixture was monitored. A faster moving spot was observed. Solvent was removed and the residue was dissolved in dichloromethane, washed with water, dried over sodium sulphate, and solvent was removed. The residue was digested with ether and filtered to yield 800 mg of white crystalline solid 225.5.–226.5° C.

$\delta$ppm (CDCl$_3$): 7.50–7.44 (m, 2H), 7.09–7.06 (m, 2H), 6.95–6.89 (m, 1H) 6.50 (bs, 1H) 4.76 (bs, 1H), 4.05–3.19 (m, 9H), 3.09 (bs, 4H), 2.02 (s, 3H).

Compound No. 02: (S)-N-[[3-[3-Fluoro-4-[N-1[4-{2-furyl (5-formyl)methyl}]piperazinyl]phenyl]-2-oxo-5-oxazolidinyl]methyl]acetamide The title compound was made with (S)-N-[[3-[3[Fluoro-4-(N-1-piperazinyl)phenyl]-2-oxo-5-oxazolidinyl]methyl acetamide and 5-chloromethyl 2-furfuraldehyde using Method A.

Compound No. 03: (S)-N-[[3-Fluoro-4-[N-1[4-(2-furyl-(5-carboxyethyl)methyl)-piperazinyl]phenyl]-2-oxo-5-oxazolidinyl]methyl]acetamide The title compound was made with (S)-N-[[3-[3[Fluoro-4-(N-1-piperazinyl)-phenyl]-2-oxo-5-oxazolidinyl]methyl acetamide ethyl-5-__chloromethyl)-2-furan-carboxylate using Method A.

Compound No. 04: (S)-N-[[3-Fluoro-4-[N-1[4-(5-bromo-2-furoyl)]piperazinyl]-phenyl]-2-oxo-5-oxazolidinyl]methyl] acetamide The title compound was made with (S)-N-[[3-[3[Fluoro-4-(N-1-piperazinyl)-phenyl]-2-oxo-5-oxazolidinyl]methyl acetamide and 5-bromo-2-furoyl chloride using Method A.

Compound No. 05: (S)-N-[[3-Fluoro-4-[N-1[4-(5-chloromethyl-2-furoyl)piperazinyl]phenyl]-2-oxo-5-oxazolidinyl]methyl]acetamide The title compound was made with (S)-N-[[3-[3[Fluoro-4-(N-1-piperazinyl)-phenyl]-2-oxo-5-oxazolidinyl]methyl acetamide and 5-chloromethyl-2-furoyl chloride using Method A.

Compound No. 06: (S)-N-[[3-Fluoro-4-[N-1[4-(5-nitro-2-furoyl)piperazinyl]phenyl]-2-oxo-5-oxazolidinyl]methyl]acetamide The title compound was made with (S)-N-[[3-[3[Fluoro-4-(N-1-piperazinyl)-phenyl]-2-oxo-5-oxazolidinyl]methyl acetamide and 5-nitro-furoyl chloride using Method A.

Compound No. 07: (S)-N[[3-[3-Fluoro-4-[N-1[4-{2-(2-thienyl)dicarbonyl}]-piperazinyl]phenyl]2-oxo-5-oxazolidinyl]methyl]acetamide The title compound was made with (S)-N-[[3-[3[Fluoro-4-(N-1-piperazinyl)-phenyl]-2-oxo-5-oxazolidinyl]methyl acetamide and 2-thiophenglyoxylyl chloride using Method A.

δppm (CDCl$_3$): 7.84(m, 2H, Ar—H), 7.47(dd, 1H, Ar—H), 7.2(m, 1H, Ar—H), 7.07(d, 1H, Ar—H), 6.92(t, 1H, Ar—H), 5.98(t, 1H, NH), 4.76(m, 1H, CH), 4.0(t, 1H, CH), 3.5–3.95 (m, 7H, CH$_2$), 3.15 (m, 2H, CH$_2$), 3.06 (m, 2H Cl$_2$), 2.02 (s, 3H, CH$_3$)

Compound No. 08: (S)-N[[3-[3-Fluoro-4-[N-1[4-(3-furoyl)]piperazinyl]phenyl]2-oxo-5-oxazolidinyl]methyl]cetamide The title compound was made with (S)-N-[[3-[3[Fluoro-4-(N-1-piperazinyl)-phenyl]-2-oxo-5-oxazolidinyl]methyl acetamide and 3-furoyl chloride using Method A.

δppm (CDCl$_3$): 8.06(s, 1H, Ar—H), 7.49(m, 2H, Ar—H), 7.09(d, 1H, Ar—H), 6.76(t, 1H, Ar—H), 6.57 (s, 1H, Ar—H), 6.03(br s, 1H, NH), 4.77 (m, 1H, CH), 4.2–3.5(m, 8H, CH$_2$), 3.06(m, 4H, CH$_2$), 2.02(s, 3H, CH$_3$)

Compound No. 09: (S)-N[[3-[3-Fluoro-4-[N-1[4-{2-furyl(5-bromo)methyl}]piperazinyl]phenyl]2-oxo-5-oxazolidinyl]methyl]acetamide The title compound was made with (S)-N-[[3-[3[Fluoro-4-(N-1-piperazinyl)-phenyl]-2-oxo-5-oxazolidinyl]methyl acetamide and 5-bromo-2-chloromethylfuran using Method A.

δppm (CDCl$_3$): 7.47 (d, 1H, Ar—H), 7.06 (d, 1H, Ar—H), 6.91 (t, 1H, Ar—H), 6.47 (d, 1H, Ar—H), 6.32 (d, 1H, Ar—H), 5.98 (t, 1H, NH), 4.76 (m, 1H, CH), 4.02 (t, 1H, CH), 3.4–3.85 (m, 9H, CH2), 3.07 (m, 4H, CH$_2$), 2.02 (s, 3H, CH$_3$).

Compound No. 10: (S)-N[[3-[3-Fluoro-4-[N-1[4-{2-thienyl(5-chloro)methyl}]-piperazinyl]phenyl]2-oxo-5-oxazolidinyl]methyl]acetamide The title compound was made with (S)-N-[[3-[3[Fluoro-4-(N-1-piperazinyl)phenyl]-2-oxo-5-oxazolidinyl]methyl acetamide and 5-chloro-2-chloromethylthiophene using Method A.

δppm (CDCl$_3$): 7.42 (dd, 1H, Ar—H), 7.05 (dd, 1H, Ar—H), 6.92 (t, 1H, Ar—H), 6.74 (d, 2H, Ar—H), 6.00 (m, 1H, CH), 4.74 (m, 1H, CH), 4.01 (t, 1H, CH), 3.3–3.8 (m, 5H, CH$_2$), 3.08 (m, 4H, CH$_2$), 2.66 (m 4H, CH$_2$) 2.01 (s, 3H, CH$_3$).

Compound No. 11: (S)-N[[3-[3-Fluoro-4-[N-1[4-(2-furylmethyl)]piperazinyl]-phenyl]2-oxo-5-oxazolidinyl]methyl]acetamide The title compound was made with (S)-N-[[3-[3[Fluoro-4-(N-1-piperazinyl)-phenyl]-2-oxo-5-oxazolidinyl]methyl acetamide and 2-chloromethylfuran using Method A.

δppm (CDCl$_3$): 7.49 (m, 2H, Ar—H), 7.07 (d, 1H, Ar—H), 6.91 (t, 1H, Ar—H), 6.51 (d, 1H, Ar—H), 6.4 (d, 1H, Ar—H), 6.1 (t, 1H, NH), 4.75 (m, 1H, CH), 4.1–3.25 (m, 10H, CH$_2$), 3.06 (m, 4H, CH$_2$), 2.03 (s, 3H, CH$_3$).

Compound No. 12: (S)-N-[[3-[3-Fluoro-4-[N-1[4-(2-thienylmethyl)]piperazinyl]-phenyl]2-oxo-5-oxazolidinyl]methyl]acetamide The title compound was made with (S)-N-[[3-[3[Fluoro-4-(N-1-piperazinyl)-phenyl]-2-oxo-5-oxazolidinyl]methyl acetamide and 2-chloromethylthiophen using Method A.

δppm (CDCl$_3$): 7.4 (m, 1H, Ar—H), 6.94 (m, 5H, Ar—H), 6.08 (t, 1H, NH), 4.71 (m, 1H, CH), 4.1–3.4 (m, 6H, CH$_2$), 3.08 (m, 4H, CH$_2$), 2.73 (m, 4H, CH$_2$), 1.98 (s, 3H, CH$_3$).

Compound No. 13: (S)-N[[3-[3-Fluoro-4-[N-1[4-(2-thienylacetyl)]piperazinyl]-phenyl]2-oxo-5-oxazolidinyl]methyl]acetamide The title compound was made with (S)-N-[[3-[3[Fluoro-4-(N-1-piperazinyl)-phenyl]-2-oxo-5-oxazolidinyl]methyl acetamide and 2-thiophenacetyl chloride using Method A.

δppm (CDCl$_3$): 7.45 (dd, 1H, Ar—H), 7.23 (d, 1H, Ar—H), 7.07 (d, 1H, Ar—H), 6.96 (m, 3H, Ar—H), 6.05 (t, 1H, CH), 4.7 (m, 1H, CH), 2.75–4.1 (m, 10H, CH$_2$), 3.01 (m, 4H, CH$_2$), 2.03 (s, 3H, CH$_3$).

Compound No. 14: (S)-N-[[3-[3-Fluoro-4-[N-1[4-{2-thienyl(4-bromo)methyl}]-piperazinyl]phenyl]-2-oxo-5-oxazolidinyl]methyl]acetamide The title compound was made with (S)-N-[[3-[3[Fluoro-4-(N-1-piperazinyl)phenyl]-2-oxo-5-oxazolidinyl]methyl acetamide and 4-bromo-2-chloromethylthiophen using Method A.

δppm (CDCl$_3$): 7.44 (dd, 1H, Ar—H), 7.2–6.8 (m, 4H, Ar—H), 5.98 (t, 1H, Ar—H) 4.76 (m, 1H, CH), 4.02 (t, 1H, CH), 3.85–3.35 (m, 5H, CH$_2$), 3.1 (m, 4H, CH$_2$), 2.69 (m, 4H, CH$_2$), 2.03 (s, 3H, CH$_3$).

Method B:

Compound No. 15: (S)-N-[[3-[3-fluoro-4-[N-1-[4-{2-furyl-(5-nitro)methyl}]piperazinyl]phenyl]-2-oxo-5-oxazolidinyl]methyl]acetamide To a suspension of (S)-N-[[3-[3[Fluoro-4-(N-1-piperazinyl)phenyl]-2-oxo-5-oxazolidinyl]methyl acetamide (770 mg, 2.29 mmol) in dichloromethane or THF (40 ml) in a round bottom flask (100 ml) filled with guard tube, was added molecular sieves (4A) followed by 5-nitro-2-furfural (420 mg, 2.98 mmol). The reaction mixture was stirred at 25° C. for 1.5 hr. Sodium triacetoxy borohydride (1.93 g, 9.10 mmol) was then added to the reaction mixture. The whole reaction mixture was allowed to stir overnight at 25° C. TLC of the reaction mixture showed a faster moving spot compared to piperazine derivative. The reaction mixture was filtered through a Buckner funnel. It was washed with dichloromethane. Organic layer was washed with water, dried over sodium sulphate and solvent was removed to give crude product which was then purified by silica gel column using 2% methanol in chloroform as eluent to afford the title compound 417 mg of m.p. 104–105° C.

δppm (CDCl$_3$): 7.48 (d, 1H), 7.34 (m, 1H), 7.12 (d, 1H), 6.98 (t, 1H), 6.56 (d, 1H), 6.07 (bs, 1H), 4.81 (m, 1H), 4.07 (t, 1H), 3.69–3.53 (m, 5H) 3.16 (bs, 4H), 2.78 (bs, 4H), 2.07 (s, 3H).

Compound No. 16: Hydrochlorid salt of (S)-N-[[3-Fluoro-4-[N-1[4-{2-furyl(5-nitro)methyl}]piperazinyl]phenyl]-2-oxo-5-oxazolidinyl]methyl]acetamide (S)-N-[[3-Fluoro-4-[N-1[4{2-furyl-(5-nitro)methyl}]piperazinyl]-phenyl]-2-oxo-5-oxazolidinyl]-methyl]acetamide hydrochloride.

To an ethanolic solution of (S)-N-[[3-Fluoro-4-[N-1[4-{2-furyl-(5-nitro)-methyl}]piperazinyl]phenyl]-2-oxo-5-oxazlidinyl]methyl]acetamide (365 mg, 0.75 mmol in 7 ml of absolute ethanol) was added 0.30 ml of HCl in ethanol (2.6 N, 0.75 mmol) in cold (5° C.) condition. The whole reaction mixture was stirred at 5–10° C. for 2.0 hr. No change in TLC was observed.

Solvent was removed. The residue was digested with dichloromethane and the solid was crystallized from methanol isopropyl alcohol mixture to give the desired compound in 111 mg of 97% pure by HPLC. Mass: 461.8 (M+H$^+$), 483.9 (M+Na$^+$)

Compound No. 17: Citrate salt of (S)-N-[[3-Fluoro-4-[N-1[4-{2-furyl(5-nitro)-methyl}]piperazinyl]phenyl]-2-oxo-5-oxazolidinyl]methyl]acetamide Citrate salt of Compound No. 15 was made according to the method described for Compound No. 16 by using citric acid in molar proportions.

Compound No. 18: (S)-N[[3-[3-Fluoro-4-[N-1[4-(2-pyrrolylmethyl)]piperazinyl]-phenyl]2-oxo-5-oxazolidinyl]methyl]acetamide The title compound was made with (S)-N-[[3-[3[Fluoro-4-(N-1-piperazinyl)-phenyl]-2-oxo-5-oxazolidinyl]methyl acetamide and 2-pyrrolecarboxaldehyde using Method B.

δppm (CDCl$_3$): 8.76(br s, 1H, NH), 7.38(d, 1H, Ar—H). 7.04(d, 1H, Ar—H), 6.91(t, 1H, Ar—H), 6.77(s, 1H, Ar—H), 6.11(m, 3H, Ar—H, NH), 4.75(m, 1H, CH), 4.0(t, 1H, CH), 3.8–3.5(m, 5H, CH$_2$), 3.08(m, 4H, CH2), 2.65(m, 4H, CH2), 2.01(s, 3H, CH3)

Compound No. 19: (S)-N[[3-[3-Fluoro-4-[N-1[4-{2-thienyl(3-methyl)methyl}]-piperazinyl]phenyl]2-oxo-5-oxazolidinyl]methyl]acetamide The title compound was made with (S)-N-[[3-[3[Fluoro-4-(N-1-piperazinyl)phenyl]-2-oxo-5-oxazolidinyl]methyl acetamide and 3-methyl-2-thiophen-carboxaldehyde using Method B.

δppm (CDCl$_3$): 7.4(d, 1H, Ar—H), 7.15(d, 1H, Ar—H), 7.03(d, 1H, Ar—H), 6.92(t, 1H, Ar—H), 6.79(d, 1H, Ar—H), 6.07(t, 1H, NH), 4.75(m, 1H, CH), 3.98(t, 1H, CH), 3.55–3.95(m, 6H, CH2), 3.09(m, 4H, CH2), 2.69(m, 3H, CH2), 2.22(s, 3H, CH3), 2.01(s, 3H, CH3)

Compound No. 20: (S)-N[[3-[3-Fluoro-4-[N-1[4-(3-furylmethyl)]piperazinyl]phenyl]2-oxo-5-oxazolidinyl]methyl]acetamide The title compound was made with (S)-N-[[3-[3[Fluoro-4-(N-1-piperazinyl)-phenyl]-2-oxo-5-oxazolidinyl]methyl acetamide and 3-furaldehyde using Method B.

δppm (CDCl$_3$): 7.42(m, 3H, Ar—H), 7.04(d, 1H, Ar—H), 6.92(t, 1H, Ar—H), 6.43(s, 1H, Ar—H), 6.0(t, 1H, NH), 4.75(m, 1H, CH), 4.01(t, 1H, CH), 3.8–3.5(m, 3H, CH2), 3.47(s, 2H, CH2), 3.1(m, 4H, CH2), 2.66 (m, 4H, CH2), 2.01(s, 3H, CH3)

Compound No. 21: (S)-N[[3-[3-Fluoro-4-[N-1[4-{2-thienyl(5-methyl)methyl}]-piperazinyl]phenyl]2-oxo-5-oxazolidinyl]methyl]acetamide The title compound was made with (S)-N-[[3-[3[Fluoro-4-(N-1-piperazinyl)-phenyl]-2-oxo-5-oxazolidinyl]methyl acetamide and 5-methyl-2-thiophencarboxaldehyde using Method B.

δppm (CDCl$_3$): 7.4(dd, 1H, Ar—H), 7.03(d, 1H, Ar—H), 6.92(t, 1H, Ar—H), 6.71(d, 1H, Ar—H), 6.58(d, 1H, Ar—H), 6.08(t, 1H, NH), 4.75(m, 1H, CH), 3.98(t, 1H, CH), 3.8–3.5(m, 5H, CH2), 3.07(m, 4H, CH2), 2.65(m, 4H, CH2), 2.45(s, 3H, CH3), 2.01(s, 3H, CH3)

Compound No. 22: (S)-N[[3-[3-Fluoro-4-[N-1[4-{2-pyrrole(1-methyl)methyl}]-piperazinyl]phenyl]2-oxo-5-oxazolidinyl]methyl]acetamide The title compound was made with (S)-N-[[3-[3[Fluoro-4-(N-1-piperazinyl)-phenyl]-2-oxo-5-oxazolidinyl]methyl acetamide and N-methyl-2-pyrrolecarboxaldehyde using Method B.

δppm (CDCl$_3$): 7.36(d, 1H, Ar—H), 7.04(d, 1H, Ar—H), 6.9(t, 1H, Ar—H), 6.6(s, 1H, Ar—H), 6.02(s, 3H, Ar—H, NH), 4.73(m, 1H, CH), 4.0(t, 1H, CH), 3.8–3.5(m, 6H, CH2), 3.49(s, 2H, CH2), 3.02(m, 4H, CH2), 2.58(m, 4H, CH2). 2.01(s, 3H, CH3)

Compound No. 23: (S)-N[[3-[3-Fluoro-4-[N-1[4-{2-thienyl(5-nitro)methyl}]piperazinyl]phenyl]2-oxo-5-oxazolidinyl]methyl]acetamide The title compound was made with (S)-N-[[3-[3[Fluoro-4-(N-1-piperazinyl)-phenyl]-2-oxo-5-oxazolidinyl]methyl acetamide and 5-nitro-2-thiophencarboxaldehyde using Method B.

δppm (CDCl$_3$): 7.80 (d, 1H, Ar—H), 7.45 (dd, 1H, Ar—H), 7.05 (d, 1H, Ar—H), 6.91 (m, 2H, Ar—H), 6.07 (t, 1H, NH), 4.76 (m, 1H, CH), 4.2–3.5 (m, 6H, CH$_2$), 3.11 (m, 4H, CH$_2$), 2.73 (m, 4H, CH$_2$), 2.02 (s, 3H, CH$_3$).

Compound No. 24: (S)-N[[3-[3-Fluoro-4-[N-1[4-[2-furyl{5-(N-thiomorpholinyl)-methyl}methyl]]piperazinyl]phenyl]2-oxo-5-oxazolidinyl]methyl]acetamide The title compound was made with (S)-N-[[3-[3[Fluoro-4-(N-1-piperazinyl)-phenyl]-2-oxo-5-oxazolidinyl]methyl acetamide and 5-(N-thiomorpholinymethyl)-2-furancarboxaldehyde using Method B.

δppm (CDCl$_3$): 7.45 (d, 1H, Ar—H), 7.05 (d, 1H, Ar—H), 6.9 (t, 1H, Ar—H), 6.18 (d, 2H, Ar—H), 6.09 (m, 1H, NH), 4.76 (m, 1H, CH), 4.02 (t, 1H, CH), 3.35–3.9 (m, 7H, CH$_2$), 3.12 (m, 4H, CH$_2$), 2.75 (m, 11H, CH$_2$), 2.02 (s, 3H, CH$_3$).

Compound No. 25: (S)-N[[3-[3-Fluoro-4-[N-1[4-[2-furyl{5-(N-morpholinyl)-methyl}methyl]]piperazinyl]phenyl]2-oxo-5-oxazolidinyl]methyl]acetamide The title compound was made with (S)-N-[[3-[3[Fluoro-4-(N-1-piperazinyl)-phenyl]-2-oxo-5-oxazolidinyl]methyl acetamide and 5-(N-morpholinylmethyl)2-furancarboxaldehyde using Method B.

δppm (CDCl$_3$): 7.5–6.3 (m, 3H, Ar—H), 6.19 (d, 2H, Ar—H), 5.9 (m, 1H, NH), 4.7 (m, 1H, CH), 4.00 (t, 1H, CH), 3.3–3.8 (m, 10H, CH$_2$), 3.09 (m, 4H, CH$_2$), 2.69 (m, 4H, CH$_2$), 2.49 (m, 4H, CH$_2$), 2.01 (s, 3H, CH$_3$).

Compound No. 26: (S)-N-[[3-Fluoro-4-[N-1[4-{2-furyl(5-acetoxymethyl)-methyl}]piperazinyl]phenyl]-2-oxo-5-oxazolidinyl]methyl]acetamide The title compound was made with (S)-N-[[3-[3[Fluoro-4-(N-1-piperazinyl)-phenyl]-2-oxo-5-oxazolidinyl]methyl acetamide and 5-(N-morpholinylmethyl)2-furylcarboxaldehyde using Method B.

δppm (CDCl$_3$): 7.42 (dd, 1H), 7.06 (dd, 1H), 6.95 (d, 1H), 6.35 (d, 1H), 6.22 (d s, 2H), 5.04 (s, 2H), 4.02 (bs, 4H, CH$_2$), 3.74 (t, 1 H), 3.75–3.6 (m, 3H), 3.64 (s, 3H) 3.10 (bs, 4 H) 2.70 (bs, 4H), 2.06 (s, 3H), 2.02 (S, 3H).

Compound No. 27: (S)-N-[[3-Fluoro-4-[N-1[4-{2-thienyl(5-bromo)methyl}]piperazinyl]phenyl]-2-oxo-5-oxazolidinyl]methyl]acetamide The title compound was made with (S)-N-[[3-[3[Fluoro-4-(N-1-piperazinyl)-phenyl]-2-oxo-5-oxazolidinyl]methyl acetamide and 5-acetoxy methyl-2-furancarboxaldehyde by using Method A.

δppm (CDCl$_3$): 7.42 (dd, 1H, Ar—H), 7.04 (d, 1H, Ar—H), 6.88 (m, 2H, Ar—H), 6.69 (d, 1H, Ar—H), 6.00 (t, 1H, NH), 4.76 (m, 1H, CH), 4.01 (t, 1H, CH), 3.4–3.8 (m, 5H, CH$_2$), 3.07 (m, 4H, CH$_2$), 2.67 (m, 4H, CH$_2$).

Compound No. 28: (S)-N-[[3-Fluoro-4-[N-1[4-(5-nitro-2-furylmethyl)piperazinyl]phenyl]-2-oxo-5-oxazolidinyl]methyl]dichloroacetamide δppm (CDCl$_3$): 7.41–6.51(m, 6H), 5.96(s, 1H), 4.81(m, 1H), 4.06(t, 1H), 3.77–3.66(m, 5H), 3.11–2.71(m, 8H)

Method C:

Compound No. 29: (S)-N[[3-[3-Fluoro-4-[N-1[4-(5-nitro-2-thienoyl)]piperazinyl]-phenyl]2-oxo-5-oxazolidinyl]methyl]acetamide hydrochloride To (S)-N-[[3-[3 [Fluoro-4-(N-1-piperazinyl)phenyl]-2-oxo-5-oxazolidinyl]-methyl]acetamide (1.14 mmol) in DMF (10 mL) cooled to 5° C., 5-nitro-2-thienoic acid (0.16 g, 0.95 mmol), N-methylmorpholine (0.12 g, 1.14 mmol) and 1-hydroxybenzotriazole (0.17 g, 1 mmol) were added and the reaction mixture was stirred for 15 min. To it 1-(3-dimethylaminopropyl)-3-ethylcarbodiimide hydrochloride (0.18 g, 0.95 mmol) was added and the reaction mixture was stirred for 18 hrs allowing it to warm to R.T. Then the reaction mixture was diluted with 25 mL water and extracted with EtOAc (3×25 mL). The combined organic layers were washed with brine, dried over anhydrous sodium sulfate and evaporated in vacuo. The residue was purified by column chromatography (3% MeOH/CHCl$_3$) to yield 0.19 g of product. This product was dissolved in dichloromethane (5 mL) and cooled to 5 C. To it 1 mL of satd. ethanolic-HCl solution was added and stirred for 15 min. Then the reaction mixture was evaporated, co-evaporated with ether and dried in vacuo to yied 0.19 g of final product.

δppm (DMSO): 8.2 (t, 1H, Ar—H), 8.1(m, 1H, Ar—H), 7.5(m, 2H, Ar—H), 7.17(d, 1H, Ar—H), 7.09(t, 1H, Ar—H), 4.7(m, 1H, CH), 4.08(t, 1h, CH), 3.73(m, 6H, CH2), 3.05 (m, 5H, CH$_2$), 1.83(s, 3H, CH3).

Compound No. 30: (S)-N[[3-[3-Fluoro-4-[N-1[4-(2',2'-diphenyl-2'hydroxy acetyl)]piperazinyl]phenyl]-2-oxo-5-oxazolidinyl]methyl]acetamide The title compound was made with (S)-N-[[3-[3[Fluoro-4-(N-1-piperazinyl)-phenyl]-2-oxo-5-oxazolidinyl]methyl] acetamide and 2,2-diphenyl-2-hydroxy acetic acid using Method C.

EXAMPLE 2

Analogues of (S)-N-[[3-[3-Fluoro[4-[3-(1α,5α,6α)-6-[N-methyl]amino]-3-azabicyclo[3.1.0]hexane]phenyl]-2-oxo-5-oxazolidinyl]methyl]acetamide (Core II)

The heteroaromatic group with the corresponding appendage can be introduced on the nitrogen atom of ring C of compounds of Formula I by one of the methods described below:

Method A:

General procedure was same as described earlier (method A). Only the core amine of Formula V is (S)-N-[[3-[3-Fluoro [4-[3-(1α,5α,6α)-6-[N-methyl]amino]-3-azabicyclo[3.1.0] hexane]phenyl]-2-oxo-5-oxazolidinyl]methyl]acetamide here.

Compound No. 31: (S)-N-[[3-[3-Fluoro[4-[3-(1α,5α,6α)-6-[N-(5-nitro-2-furoyl)-N-methyl]amino]-3-azabicyclo-[3.1.0]hexane]phenyl]-2-oxo-5-oxazolidinyl]-methyl] acetamide Preparation of (S)-N-[[3-[3-Fluoro[4-[3-(1α,5α,6α)-6-[N-methyl]amino]-3-azabicyclo[3.1.0]hexane]phenyl]-2-oxo-5-oxazolidinyl]methyl]acetamide (core II)

(a) Preparation of 3-Fluoro[4-[3-(1α,5α,6α,)-6-[N-(tertbutoxycarbonyl)amino]-3-azabicyclo-[3.1.0]hexane] nitrobenzene.

(1α,5α,6α)-6-Amino-3-azabicyclo[3.1.0]hexane (7.0 g, 0.03535 mol) was taken in CH$_3$CN (50 mL) and diisopropyl ethyl amine (4.5606 g, 0.03535 mol) was added followed by 3,4-difluoro nitrobenzene (5.6212 g, 0.03535 mol) and heated at 70° C. for 4 hrs. The reaction was monitored by the disappearance of the starting material on the TLC (eluent CHCl$_3$:MeOH (19:1)). The reaction mixture was concentrated under vacuum, triturated with H$_2$O, filtered, washed with hexane and dried to obtain the title compound. Yield: 10 g δppm (CDCl$_3$): 7.94–6.50 (m, 3H), 4.80 (5, 1H) 3.95–3.63 (m, 4H), 2.43 (s, 1H), 1.92 (5, 2H), 1.47 (s. 9H).

(b) Preparation of 3-Fluoro[4-[3-(1α,5α,6α)-6[N-(tertbutoxycarbonyl)-N-methyl]-amino]-3-azabicyclo-[3.1.0]hexane]nitrobenzene 3-Fluoro[4-[3-(1α,5α,6α)-6-[N-(tertbutoxycarbonyl)-amino]-3-azabicyclo-[3.1.0]hexane]nitrobenzene (10 g, 0.029 mol) was taken in 60 ml THF at 0° C. Sodium hydride (1.06 g, 0.045 mol) was added portion-wise over 5 min. After complete addition the reaction mixture was stirred for 30 min. at 0° C. Methyl iodide (8.42 g, 0.059 mol) was then added over 10 min. at 0° C. followed by tert n-butyl ammonium iodide (1 g). The reaction mixture was stirred for 4 hrs. The reaction mixture was then concentrated under vacuum. H$_2$O (50 mL) was added followed by extraction with dichloromethane (3×50 mL). The combined organic layer was dried over Na$_2$SO$_4$, filtered and concentrated to obtain the title compound. Yield: 10.25 g δppm (MeOD): 7.91–6.47 (m, 3H), 3.89–3.61 (m, 4H) 2.8 (s, 3H), 2.34 (s, 1H), 1.96 (s, 2H), 1.46 (5, 9H).

(c) Preparation of 3-Fluoro[4-{3-(1α,5α,6α)-6-[N-(tertbutoxycarbonyl)-N-methylamino}-3-azabicyclo-[3.1.0] hexane]aniline.

3-Fluoro[4-[3-(1α,5α,6α)6-[N-(tertbutoxycarbonyl)-N-methyl]-amino]-3-azabicyclo-[3.1.0]hexane]nitrobenzene (26 g, 0.074 mol) was taken in 75 mL THF and 75 mL MeOH. 10% Pd/C (dry) (3 g) was added and the reaction mixture was shaken in a Parr hydrogenator at 40 psi for 3 hours. The reaction mixture was filtered through celite bed. The filtrate was concentrated to obtain the title compound. Yield: 21.2 g δppm (CDCl$_3$)(MeOD): 6.55–6.33 (m, 3H), 3.54–3.00 (m, 4H) 2.87 (s, 3H), 2.55 (s, 1H), 1.96 (s, 2H) 1.40 (s, 9H).

(d) Preparation of 3-Fluoro[4-[3-(1α,5α,6α)-6-[N-(tert butoxy carbonyl)-N-methyl]amino]-3-azabicyclo-[3.1.0] hexane]benzyloxy carbamate 3-Fluoro[4-[3-(1α,5α,6α)-6-[N-(tert-butoxy carbonyl)-N-methyl)amino]-3-azabicyclo[3.1.0]hexane]aniline (21 g, 0.065 mol) was taken in THF (100 ml and cooled to −15° C. Sodium bicarbonate (27.47 g, 0.32 mol) was added followed by benzyl chloroformate (14.5 g, 0.055 mol) which was added slowly over 30 min. After complete addition the stirring was combined for the maintaining the temperature between 0–5° C. The reaction was monitored by the disappearance of the reaction mixture on TLC (eluent CHCl$_3$:MeOH: 9:1). The reaction mixture was filtered and filtrate concentrated under vacuum. H$_2$O (20 ml) was added and extracted with CH$_2$Cl$_2$ (3×100 ml). The combined organic layer was dried over Na$_2$SO$_4$. This was filtered and the filtrate concentrated. The semisolid was triturated with MeOH. The so was filtered to obtain the title compound.

δppm (CDCl$_3$): 7.4:6.5 (m, 8H), 5.24 (s, 2H), 3.8–3.3(m, 4H), 2.92 (s, 3H), 2.61 (s, 1H), 1.90 (s, 2H), 1.54 (s, 9H, tBu).

(e) Preparation of (S)-N-[3-[3-Fluoro[4-[3-(1α,5α,6α)-6-(N-(tertbutoxycarboxy-N-methyl]amino]-3-azabicyclo [3.1.0]hexane]phenyl]-2-oxo-5-oxazolidinyl]methyl alcohol.

3-Fluoro[4-[3-(1α,5α,6α)-6-(N-(tertbutoxycarbonyl)-N-methyl]amino]-3-azabicyclo[3.1.0]hexane]benzyloxy carbamate (21 g, 0.04615 mol) was taken in freshly distilled THF (200 mL). The system was thoroughly flushed with N$_2$. The temperature was then brought down to −78° C. in acetone dry ice. n-BuLi (59.13 mL of 15% solution in hexane, 0.13846 mol) was added over 30 min. maintaining the temperature at −78° C. The stirring was continued for 2.5 hours at −78° C. R(−) Glycidyl butyrate was added in one go and stirred at −78° C. for further 1.5 hours. The temperature was gradually increased to rt. and stirred over night. 20% aqueous solution of NH$_4$Cl (200 ml) was then added gradually added over 10 min. After 30 min. stirring, the organic layer was separated. The aqueous layer was further extracted with EtOAc (3×75 ml). The combined organic was dried over Na₂SO₄, filtered and concentrated. The product was purified by silica gel column chromatography (100–200) eluent (2% MeOH:98% CHCl₃) to yield 14 g.

δppm (CDCl₃): 7.35–6.55 (m, 3H), 4.7 (m, 1H), 3.9–3.8 (m, 4H), 3.7–3.2 (m, 4H), 2.8 (s, 3H, N—CH₃), 2.5 (S, 1H), 1.8 (s, 2H), 1.47 (s, 9H).

(f) Preparation of (S)-N-[3-[3-Fluoro[4-[3-(1α,5α,6α)-6-[N-(tertbutoxycarbonyl)-N-Methyl]amino]-3-azabicyclo[3.1.0]hexane]phenyl]-2-oxa-5-oxazolidinyl]methyl methanesulfonate.

(S)-N-[3-[3-Fluoro[4-[3-(1α,5α,6α)-6-[N-(tertbutoxycarbonyl)-N-methyl]amino]-3-azabicyclo[3.1.0]hexane]phenyl]-2-oxa-5-oxazolidinyl]methyl alcohol (16 g, 0.038 mol) was taken in 50 ml pyridine at 5–10° C. and methane sulphonyl chloride (12.71 g, 0.14 mol) was added over 5 min. The stirring was continued for 4 hours. The progress of the reaction was monitored by the disappearance of the starting material on TLC (eluent 10% CHCl₃:10% MeOH). The reaction mixture was filtered, filtrates concentrated under vacuum, washed with H₂O (50 ml) and extracted with CH₂Cl₂ (3×75 mL). The combined organic layer was dried over Na₂SO₄, filtered and filtrate concentrated. This was dried thoroughly under vacuum.

(g) Preparation of (S)-N-[3-[3-Fluoro[4-[3-(1α,5α,6α)-6-[N-(tertbutoxycarbonyl)-N-Methyl]amino]-3-azabicyclo[3.1.0]hexane]phenyl]-2-oxa-5-oxazolidinyl]methyl azide.

(S)-N-[3-[3-Fluoro[4-[3-(1α,5α,6α)-6-[N-(tertbutoxycarbonyl)-N-methyl]amino]-3-azabicyclo[3.1.0]hexane]phenyl]-2-oxa-5-oxazolidinyl]methyl methane sulphonate (15 g, 0.03 mol) was taken in DMF (50 ml) and NaN₃ (9.76 g, 0.15 mol) was added and heated at 70° C. for 4 hours. The progress of the reaction was monitored by the disappearance of the starting material on TLC. The reaction mixture was filtered. The filtrate was concentrated under vacuum. This was washed with H₂O and extracted EtOAc (3×75 ml). The combined organic layer was dried over Na₂SO₄, filtered and concentrated to obtain the title compound. Yield 11.5 g.

(h) Preparation of (S)-N-[3-[3-[3-Fluoro[4-[3-(1α,5α,6α)-6-[N-(tertbutoxycarbonyl)-N-methyl]amino]-3-azabicyclo[3.1.0]hexane]phenyl]-2-oxo-5-oxazolidinyl]methylamine (S)-N-[3-[3-Fluoro[4-[3-(1α,5α,6α)-6-[N-(tertbutoxycarbonyl)-N-methyl]amino]-3-azabicyclo[3.1.0]hexane]phenyl]-2-oxo-5-oxazolidinyl]methyl azide (11.3 g, 0.026 mol) was taken in 75 ml MeOH and 75 ml EtOAc and 10% Pd/C was added. The reaction mixture was shaken at 50 psi for 6 hrs. The progress of the reaction was monitored by the disappearance of the starting material on the TLC. The reaction mixture was filtered through a celite bed. The filtrate was concentrated. The product was triturated with diethyl ether. The solid was filtered, to obtain the title compound. Yield –7.6 g.

(i) Preparation of (S)-N-[3-[3-Fluoro[4-[3-(1α, 5α, 6α)-6-[N-(tertbutoxycarbonyl)-N-Methyl]amino]-3-azabicyclo[3.1.0]hexane]phenyl]-2-oxa-5-oxazolidinyl]acetamide.

(S)-N-[3-[3-Fluoro[4-[3-(1α,5α,6α)-6-[N-(tertbutoxycarbonyl)-N-methyl]amino]-3-azabicyclo[3.1.0]hexane]phenyl]-2-oxo-5-oxazolidinyl]methylamine (7.6 g, 0.018 mol) was taken in pyridine (8 ml), CH₂Cl₂ (50 mL) and acetic anhydride (2.214 g, 0.0217 mol) at 0–10° C. The reaction mixture was stirred and the progress of the reaction was monitored by the disappearance of the starting material on the TLC eluent (CHCl₃:MeOH: 9:1). The reaction mixture was concentrated under vacuum. The concentrate was washed with H₂O (50 mL) and extracted with CH₂Cl₂ (3×50 mL). The combined organic layer was dried over Na₂SO₄, filtered and concentrated. This product was triturated with diethyl ether, filtered and dried to yield the little compound. Yield: 6.6 g.

δppm (CDCl₃): 7.33–6.56 (m, 3H), 6.19 (t, 1H), 4.73 (m, 1H), 3.98 (t, 1H), 3.77–3.2 (m, 7H) 2.8 (s, 3H), 2.52 (s, 1H), 2.0 (s, 3H), 1.96 (S, 2H), 1.48 (s, 9H).

(j) Preparation of (S)-N-[3-[3-Fluoro[4-[3-(1α,5α,6α)-6-[N-Methyl]amino]-3-azabicyclo[3.1.0]hexane]phenyl]-2-oxa-5-oxazolidinyl]acetamide.

(S)-N-[3-[3-Fluoro[4-[3-(1α,5α,6α)-6-[N-(tertbutoxycarbonyl)-N-Methyl]amino]-3-azabicyclo[3.1.0]hexane]phenyl]-2-oxa-5-oxazolidinyl]acetamide (1 g) was taken in CH₂Cl₂ (50 mL) at 0° C. and CF₃COOH(10 mL) was added and stirred for 4 h. The reaction mixture was concentrated under vacuum. The residue was dissolved in EtOAc and neutralised with solid NaHCO₃. The EtOAc layer was filtered and the filtrate was concentrated to obtain the title compound.

Compound No. 31: (S)-N-[[3-[3-Fluoro[4-[3-(1α,5α,6α)-6-[N-(5-nitro-2-furoyl)-N-methyl]amino]-3-azabicyclo-[3.1.0]hexane]phenyl]-2-oxo-5-oxazolidinyl]methyl]acetamide The title compound was made using (S)-N-[3-[3-Fluoro[4-[3-(1α,5α,6α)-6-[N-Methyl]amino]-3-azabicyclo[3.1.0]hexane]phenyl]-2-oxa-5-oxazolidinyl]acetamide and 5-nitro-furoyl chloride using Method A.

δppm (CDCl₃): 7.7–60 (m, 6H), 4,74 (m, 1H), 4.0–2.9 (m, 11H), 2.43 (s, 2H), 2.01 (s, 3H), 1.62 (s, 1H), 1.91 (s, 2H)

Compound No. 32: (S)-N-[[3-[3-Fluoro[4-[3-(1α, 5α, 6α)-6-[N-(3-furoyl)-N-methyl]amino]-3-azabicyclo-[3.1.0]hexane]phenyl]-2-oxo-5-oxazolidinyl]methyl]acetamide The title compound was made using (S)-N-[3-[3-Fluoro[4-[3-(1α,5α,6α)-6-[N-methyl]amino]-3-azabicyclo[3.1.0]hexane]phenyl]-2-oxa-5-oxazolidinyl]acetamide and 3-furoic acid using method A.

Compound No. 71: (S)-N-[[3-[3-Fluoro[4-[3-(1α, 5α, 6α)-6-[N-(2-thiopheneacetyl)-N-methyl]amino]-3-azabicyclo-[3.1.0]hexane]phenyl]-2-oxo-5-oxazolidinyl]methyl]acetamide The title compound was made using (S)-N-[3-[3-Fluoro[4-[3-(1α,5α,6α)-6-[N-methyl]amino]-3-azabicyclo[3.1.0]hexane]phenyl]-2-oxa-5-oxazolidinyl]acetamide and 2-thiopheneacetyl chloride using Method A.

Compound No. 72: (S)-N-[[3-[3-Fluoro[4-[3-(1α,5α,6α)-6-[N-(5-formyl-2-furylmethyl)-N-methyl]amino]-3-azabicyclo-[3.1.0]hexane]phenyl]-2-oxo-5-oxazolidinyl]methyl]acetamide The title compound was made using (S)-N-[3-[3-Fluoro[4-[3-(1α,5α,6α)-6-[N-Methyl]amino]-3-azabicyclo[3.1.0]hexane]phenyl]-2-oxa-5-oxazolidinyl]acetamide and 5-formyl-2-furylmethyl chloride using Method A.

Compound No. 73: (S)-N-[[3-[3-Fluoro[4-[3-(1α,5α,6α)-6-[N-(3-thienoyl)-N-methyl]amino]-3-azabicyclo-[3.1.0]hexane]phenyl]-2-oxo-5-oxazolidinyl]methyl]acetamide The title compound was made using (S)-N-[3-[3-Fluoro[4-[3-(1α,5α,6α)-6-[N-Methyl]amino]-3-azabicyclo[3.1.0]hexane]phenyl]-2-oxa-5-oxazolidinyl]acetamide and 3-chlorothienoyl chloride using Method A.

Compound No. 33: (S)-N-[[3-[3-Fluoro[4-[3-(1α,5α,6α)-6-[N-(5-bromo-2-furoyl)-N-methyl]amino]-3-azabicyclo-[3.1.0]hexane]phenyl]-2-oxo-5-oxazolidinyl]methyl]acetamide The title compound was made using (S)-N-[3-[3-Fluoro[4-[3-(1α,5α,6α)-6-[N-Methyl]amino]-3-azabicyclo[3.1.0]hexane]phenyl]-2-oxa-5-oxazolidinyl]acetamide and 5-bromo2-furoyl chloride using Method A.

Method B:

General procedure was same as described earlier in section 7.1.1.2. (Method B) described earlier for Compound No. 15. Only the core amine of Formula V is (S)-N-[[3-[3-Fluoro[4-[3-(1α,5α,6α)-6-[N-methyl]amino]-3-azabicyclo[3.1.0]hexane]-phenyl]-2-oxo-5-oxazolidinyl]methyl] acetamide here.

Compound No. 34: (S)-N-[[3-[3-Fluoro[4-[3-(1α,5α,6α)-6-[N-(5-nitro-2-thienyl-methyl)-N-methyl]amino]-3-azabicyclo-[3.1.0]hexane]phenyl]-2-oxo-5-oxazolidinyl]methyl]acetamide The title compound was made using (S)-N-[3-[3-Fluoro[4-[3-(1α,5α,6α)-6-[N-methyl]amino]-3-azabicyclo[3.1.0]hexane]phenyl]-2-oxa-5-oxazolidinyl]acetamide and 5-nitro-thiophene-2-carboxyaldehyde using Method B.

Compound No. 35: (S)-N-[[3-[3-Fluoro[4-[3-(1α,5α,6α)-6-[N-(5-nitro-2-furylmethyl)-N-methyl]amino]-3-azabicyclo-[3.1.0]hexane]phenyl]-2-oxo-5-oxazolidinyl]methyl]acetamide The title compound was made using (S)-N-[3-[3-Fluoro[4-[3-(1α,5α,6α)-6-[N-Methyl]amino]-3-azabicyclo[3.1.0]hexane]phenyl]-2-oxa-5-oxazolidinyl]acetamide and 5-nitro-furan-2-carboxyaldehyde using Method B.

Analogues of (S)-N-[3-[3-Fluoro[4-[3-(1α,5α,6α)-6-[N-(tertbutoxycarbonyl)-N-Methyl]aminomethyl]-3-azabicyclo[3.1.0]hexane]phenyl]-2-oxa-5-oxazolidinyl]acetamide (core III).

The heteroaromatic group with the corresponding appendage can be introduced on the nitrogen atom of ring C of compounds of Formula I by one of the methods described below:

Method A:

General procedure was same as described earlier in Method A described earlier for Compound No. 01. Only the core amine of Formula V is (S)-N-[3-[3-Fluoro[4-[3-(1α,5α,6α)-6-[N-(tertbutoxycarbonyl)-N-Methyl]aminomethyl]-3-azabicyclo[3.1.0]hexane]phenyl]-2-oxa-5-oxazolidinyl]acetamide (core III).

Compound No. 36: (S)-N-[[3-[3-Fluoro[4-[3-(1α,5α,6α)-6-[N-(5-formyl-2-furylmethyl)-N-methyl]aminomethyl]-3-azabicyclo-[3.1.0]hexane]phenyl]-2-oxo-5-oxazolidinyl]methyl]acetamide (a) Preparation of 3-Fluoro[4-[3-(1α,5α,6α)-6-[N-(tertbutoxycarbonyl)-aminomethyl]-3-azabicyclo-[3.1.0]hexane]nitrobenzene.

(1α,5α,6α)-6-Aminomethyl-3-azabicyclo[3.1.0]hexane (7.0 g, 0.03535 moles) was taken in CH$_3$CN 50 mL and diisopropyl ethyl amine (4.5606 g, 0.03535 mol) was added followed by 3,4-difluoro nitrobenzene (5.6212 g, 0.03535 mol) and heated at 70° C. for 4 hrs. The reaction was monitored by the disappearance of the starting material on the (eluent CHCl$_3$ (19):MeOH (1). The reaction mixture was concentrated under vacuum, triturated with H$_2$O, filtered, washed with hexane and dried to obtain the title compound.

(b) Preparation of 3-Fluoro[4-[3-(1α,5α,6α)-6-[N-(tertbutoxycarbonyl)-N-Methyl]-aminomethyl]-3-azabicyclo-[3.1.0]hexane]nitrobenzene 3-Fluoro[4-[3-(1α,5α,6α)-6-[N-(tertbutoxycarbonyl)-N-methyl]aminomethyl]-3-azabicyclo-[3.1.0]hexane] nitrobenzene (10 g, 0.029) was taken in 60 ml THF at 0° C. Sodium hydride (1.06 g, 0.045 mol) was added portion-wise over 5 min. after complete addition the reaction mixture was stirred for 30 min. at 0° C. Methyl iodide (8.42 g, 0.059 mol) was then added over 10 min. at 0° C. followed by tat n-butyl ammonium iodide (1 g). The reaction mixture was stirred for 4 hrs. The reaction mixture was then concentrated under vacuum. H$_2$O (50 mL) was added followed by extraction with CH$_2$Cl$_2$ (3×50 mL). The combined organic layer was dried over Na$_2$SO$_4$, filtered and concentrated to obtain the title compound.

(c) Preparation of 3-Fluoro[4-[3-(1α,5α,6α)-6-[N-(tertbutoxycarbonyl)-Nethyl]-aminomethyl]-3-azabicyclo-[3.1.0]hexane]aniline 3-Fluoro[4-[3-(1α,5α,6α)-6-[N-(tertbutoxycarbonyl)-N-Methyl]-aminomethyl]-3-azabicyclo-[3.1.0]hexane] nitrobenzene (26 g, 0.074 mol) was taken in 75 mL THF and 75 mL MeOH 10% Pd/C dry (3 g) was added and the reaction mixture was shaken in a parr hydrogenator at 40 psi for 3 hours. The reaction mixture was filtered through celite led. The filtrate was concentrated to obtain the title compound.

(d) Preparation of 3-Fluoro[4-[3-(1α,5α,6α)-6-[N-(tertbutoxycarbonyl)-N-methyl]amino]-3-azabicycl-[3.1.0] hexane]benzyloxy carbamate 3-Fluoro[4-[3-(1α,5α,6α)-6-[N-(tert-butoxycarbonyl)-N-methyl)aminomethyl]-3-azabicyclo[3.1.0]hexane]aniline (21 g, 0.065 mol) was taken in THF (100 ml and cooled to −15° C. Sodium bicarbonate (27.47 g, 0.32 mol) was added followed by benzyl chloroformate (14.5 g, 0.055 mol) which was added slowly over 30 min. after complete addition the stirring was combined for the maintaining the temperature between 0–5° C. The reaction was monitored by the disappearance of the reaction mixture on TLC (eluent CHCl$_3$:MeOH: 9:1). The reaction mixture was filtered and filtrate concentrated under vacuum. H$_2$O (20 ml) was added and extracted with CH2Cl2 (3×100 ml). The combined organic layer was dried over Na$_2$SO$_4$. This was filtered, filtrate concentrated. The semisolid was triturated with MeOH. The solid was filtered to obtain the title compound.

(e) Preparation of (S)-N-[3-[3-Fluoro[4-[3-(1α,5α,6α)-N-(tertbutoxycarboxy-N-methyl]aminomethyl]-3-azabicyclo[3.1.0]hexane]phenyl]-2-oxo-5-oxazolidinyl] methyl alcohol.

3-Fluoro[4-[3-(1α,5α,6α)-6-(N-(tertbutoxycarbonyl)-N-methyl]aminomethyl]-3-azabicyclo[3.1.0]hexane] benzyloxy carbamate (21 g, 0.04615 mol) was taken in freshly distilled THF (200 mL). The system was thoroughly flushed with N$_2$. The temperature was then brought down to −78° C. in acetone dry ice. n-BuLi (59.13 mL of 15% solution in hexane, 0.13846 mol) was added over 30 min. maintaining the temperature at −78° C. The stirring was continued for 2.5 hours at −78° C. R(−) Glycidyl butyrate was added in one go and stirred at −78° C. for further 1.5 hours. The temperature was gradually increased to rt. and stirred over night. 20% Solution of NH$_4$Cl (200 ml) was then added gradually added over 10 min. after 30 min. stirring, the organic layer was separated. The aqueous layer was further extracted with EtOAc (3×75 ml). The combined organic was dried over Na$_2$SO$_4$, filtered and concentrated. The product was purified by silica gel column chromatography (100–200) eluent (2% MeOH:98% CHCl$_3$) to yield 14 g.

(f) Preparation of (S)-N-[3-[3-Fluoro[4-[3-(1α,5α,6α)-[N-(tertbutoxycarbonyl)-N-methyl]aminomethyl]-3-azabicyclo[3.1.0]hexane]-phenyl]-2-oxa-5-oxazolidinyl] methyl methanesulfonate.

(S)-N-[3-[3-Fluoro[4-[3-(1α,5α,6α)-6-[N-(tertbutoxycarbonyl)-N-methyl]aminomethyl]-3-azabicyclo[3.1.0]hexane]phenyl]-2-oxa-5-oxazolidinyl]methyl alcohol (16 g, 0.038 mol) was taken in 50 ml pyridine at 5–10° C. and methane sulphonyl chloride (12.71 g, 0.14 mol) was added over 5 min. The stirring was continued for 4 hours. The progress of the reaction was monitored by the disappearance of the starting material on TLC (eluent 10% CHCl₃:10% MeOH). The reaction mixture was filtered, concentrated under vacuum, washed with H₂O (50 ml) and extracted with CH₂Cl₂ (3×75 mL). The combined organic layer was dried over Na₂SO₄, filtered and filtrate concentrated. This was dried thoroughly under vacuum.

(g) Preparation of (S)-N-[3-[3-Fluoro[4-[3-(1α,5α,6α)-6-[N-(tertbutoxycarbonyl)-N-Methyl]aminomethyl]-3-azabicyclo[3.1.0]hexane]-phenyl]-2-oxa-5-oxazolidinyl] methyl azide.

(S)-N-[3-[3-Fluoro[4-[3-(1α,5α,6α)-[N-(tertbutoxycarbonyl)-N-methyl]aminomethyl]-3-azabicyclo[3.1.0]hexane]phenyl]-2-oxa-5-oxazolidinyl]methyl methane sulphonate (15 g, 0.03 mol) was taken in DMF (50 ml) and NaN₃ (9.76 g, 0.15 mol) was added and heated at 70° C. for 4 hours. The progress of the reaction was monitored by the disappearance of the starting material on TLC. The reaction mixture was filtered. The filtrate was concentrated under vacuum. This was washed with H₂O and extracted EtOAc (3×75 ml). The combined organic layer was dried over Na₂SO₄, filtered and concentrated to obtain the title compound. Yield: 11.5 g.

(h) Preparation of (S)-N-[3-[3-[3-Fluoro[4-[3-(1α,5α,6α)-6-[N-(tertbutoxycarbonyl)-N-methyl]aminomethyl]-3-azabicyclo[3.1.0]hexane]-phenyl]-2-oxo-5-oxazolidinyl] methyl amine (S)-N-[3-[3-[3-Fluoro[4-[3-(1α,5α,6α)-6-[N-(tertbutoxycarbonyl)-N-methyl]aminomethyl]-3-azabicyclo[3.1.0]hexane]phenyl]-2-oxo-5-oxazolidinyl]methyl azide (11.3 g, 0.026 mol) was taken in 75 ml MeOH and 75 ml EtOAc and 10% Pd/C was added. The reaction mixture was shaken at 50 psi for 6 hrs. The progress of the reaction was monitored by the disappearance of the starting material on the TLC. The reaction mixture was filtered through a celite bed. The filtrate was concentrated. The product was triturated with diethyl ether. The solid was filtered, to obtain the title compound. Yield –7.6 g.

(i) Preparation of (S)-N-[3-[3-Fluoro[4-[3-(1α,5α,6α)-6-[N-(tertbutoxycarbonyl)-N-Methyl]aminomethyl]-3-azabicyclo[3.1.0]hexane]-phenyl]-2-oxa-5-oxazolidinyl] acetamide.

(S)-N-[3-[3-Fluoro[4-[3-(1α,5α,6α)-6-[N-(tertbutoxycarbonyl)-N-methyl]aminomethyl]-3-azabicyclo[3.1.0]hexane]phenyl]-2-oxo-5-oxazolidinyl]methyl amine (7.6 g, 0.018 mol) was taken in pyridine (8 ml), CH₂Cl₂ (50 mL) and acetic anhydride (2.214 g, 0.0217 mol) at 0–10° C. The reaction mixture was stirred and the progress of the reaction was monitored by the disappearance of the starting material on the TLC eluent (CHCl₃:MeOH: 9:1). The reaction mixture was concentrated under vacuum. The reaction mixture was washed with H₂O (50 mL) and extracted with CH₂Cl₂ (3×50 mL). The combined organic layer was dried over Na₂SO₄, filtered and concentrated. This product was triturated with diethyl ether, filtered and dried to yield the little compound. Yield –6.6 g.

(j) Preparation of (S)-N-[3-[3-Fluoro[4-[3-(1α,5α,6α)-6-[N-methyl]aminomethyl]-3-azabicyclo[3.1.0]hexane]phenyl]-2-oxa-5-oxazolidinyl]acetamide.

(S)-N-[3-[3-Fluoro[4-[3-(1α,5α,6α)-6-[N-(tertbutoxycarbonyl)-N-Methyl]amino]-3-azabicyclo[3.1.0]hexane]phenyl]-2-oxa-5-oxazolidinyl]acetamide (1 g) was taken in CH₂C₂ (50 mL) at 0° C. and CF₃COOH(10 mL) was added and stirred for 4 h. The reaction mixture was concentrated under vacuum. The residue was dissolved in EtOAc and neutralised with solid NaHCO₃. The EtOAc layer was filtered and the filterate was concentrated to obtain the title compound.

(S)-N-[[3-[3-Fluoro[4-[3-(1α,5α,6α)-6-[N-(5-formyl-2-furylmethyl)-N-methyl]aminomethyl]-3-azabicyclo-[3.1.0] hexane]phenyl]-2-oxo-5-oxazolidinyl]-methyl]acetamide The title compound was made using (S)-N-[3-[3-Fluoro [4-[3-(1α,5α,6α)-6-[N-Methyl]aminomethyl]-3-azabicyclo [3.1.0]hexane]phenyl)-2-oxa-5-oxazolidinyl]acetamide and 5-formyl-2-furylmethylene chloride using Method A.

Compound No. 37: (S)-N-[[3-[3-Fluoro[4-[3-(1α,5α,6α)-6-[N-(5-carboxyethyl-2-furylmethyl)-N-methyl] aminomethyl]-3-azabicyclo-[3.1.0]hexane]phenyl]-2-oxo-5-oxazolidinyl]methyl]acetamide The title compound was made using (S)-N-[3-[3-Fluoro [4-[3-(1α,5α,6α)-6-[N-Methyl]aminomethyl]-3-azabicyclo [3.1.0]hexane]phenyl]-2-oxa-5-oxazolidinyl]acetamide and ethyl-5-(chloromethyl)-2-furan carboxylate using Method A.

Compound No. 38: (S)-N-[[3-[3-Fluoro[4-[3-(1α,5α,6α)-6-[N-(2-thiopheneacetyl)-N-methyl]aminomethyl]-3-azabicyclo-[3.1.0]hexane]phenyl]-2-oxo-5-oxazolidinyl] methyl]acetamide The title compound was made using (S)-N-[3-[3-Fluoro [4-[3-(1α,5α,6α)-6-[N-Methyl]amino]-3-azabicyclo[3.1.0] hexane]phenyl]-2-oxa-5-oxazolidinyl]acetamide and 2-thiopheneacetyl chloride using Method A.

Method-B:

General procedure was same as described earlier in Method A for the preparation of Compound No. 15. Only the core amine of Formula V is (S)-N-[3-[3-Fluoro[4-[3-(1α, 5α,6α)-6-[N-Methyl]aminomethyl]-3-azabicyclo[3.1.0] hexane]phenyl]-2-oxa-5-oxazolidinyl]acetamide (core III)

Compound No. 39: (S)-N-[[3-[3-Fluorol[4-[3-(1α,5α,6α)-6-[N-(5-nitro-2-thienyl-methyl)-N-methyl]aminomethyl]-3-azabicyclo-[3.1.0]hexane]phenyl]-2-oxo-5-oxazolidinyl] methyl]acetamide The title compound was made using (S)-N-[3-[3-Fluoro [4-[3-(1α,5α,6α)-6-[N-Methyl]aminomethyl]-3-azabicyclo [3.1.0]hexane]phenyl]-2-oxa-5-oxazolidinyl]acetamide and 5-nitro thiophene-2-carboxyaldehyde using Method B.

Compound No. 40: (S)-N-[[3-[3-Fluoro[4-[3-(1α,5α,6α)-6-[N-(5-nitro-2-furylmethyl)-N-methyl]aminomethyl]-3-azabicyclo-[3.1.0]hexane]phenyl]-2-oxo-5-oxazolidinyl] methyl]acetamide The title compound was made using (S)-N-[3-[3-Fluoro [4-[3-(1α,5α,6α)-6-[N-Methyl]aminomethyl]-3-azabicyclo [3.1.0]hexane]phenyl]-2-oxa-5-oxazolidinyl]acetamide and 5-nitro-furan-2-carboxyaldehyde using Method B.

EXAMPLE 4

Analogues of (S)-N-{3-[4-[4-N-methyl amino peperidin-1-yl]-3-fluoro-phenyl}-2-oxo-oxazolidin-5-yl]methyl acetamide (core IV).

The heteroaromatic group with the corresponding appendage can be introduced on the nitrogen atom of ring C of compounds of Formula I by one of the methods described below:

Method-A:

General procedure was same as described earlier (Method A) for Compound No. 1. Only the amine of Formula V is (S)-N-{3-[4-[4-N-methylaminopiperidin-1-yl]-3-fluorophenyl}-2-oxo-oxazolidin-5-yl methyl acetamide (core IV).

Compound No. 74: Preparation of (S)-N-[[3-[4-[4-(N-methyl-N-2furyl(5-formyl)-methylaminopiperidine-1-yl]-3-fluorophenyl]-2-oxo-oxazolidin-5-yl]methyl]-acetamide.

Preparation of (S)-N-{3-[4-[4-N-methylaminopiperidin-1-yl]-3-fluorophenyl}-2-oxo-oxazolidin-5-yl]methyl acetamide (core IV)

(a) 1-[4(N-t-Butyloxycarbonylamino)piperidin-1-yl]-3-fluoro]-nitrobenzene

To a solution of difluoronitrobenzene (40 g; 200 mmol) in acetonitrile (400 ml) was treated with ethyldiisopropyl amine (28.4 g; 219.72 mmol) and 4-(t-butyloxycarbonyl) aminopiperidine (31.8 g; 199 mmol). The whole reaction mixture was then heated at 60° C. for 6.0 hr. The solution was cooled to ambient temperature and conc. in vacuo. The residue was dissolved in ethyl acetate and washed with water. Ethyl acetate layer was dried over anhydrous sodium sulphate. Solvent was removed to afford a yellow solid (60 g).

δppm (CDCl$_3$): 7.98–7.80 (m, 2H), 6.91 (t, J=9 Hz, 1H) 4.53 (bs, 1H), 3.65 (d, J=12 Hz, 3H) 2.98 (t, J=13 Hz, 2H), 2.07 (m, 2H), 1.69–1.53 (m, 3H), 1.52 (s, 9H).

(b) 1-[4-(N-t-Butyloxy carbonyl N methyl) aminopiperidin-1-yl]-3-fluoro]nitrobenzene (B)

To a solution of intermediate A (89 mmol) in dry tetrahydrofuran (400 ml) was added sodium hydride (60%, 106 mmol) in cold condition (0° C.) followed by tetrabutyl ammonium iodide (10 mmol). The reaction mixture was stirred at cold to r.t. for 2.0 hr. Methyl iodide (267 mmol) was then added at 0° C. Reaction mixture was stirred at r.t. for 12 hr. A faster moving spot was appeared. Excess sodium hydride was decomposed with water. Tetrahydrofuran was removed. The residue was dissolved in ethyl acetate, washed with water, brine and then with water. Organic layer was dried over anhydrous sodium sulphate and solvent was removed. A yellow solid (32 g) was obtained.

δppm (CDCl$_3$): 6.81 (t, J=12 Hz, 1H) 6.44–6.37 (m, 2H), 4.70 (bs, 1H) 2.91 (d, J=12H, 2H), 2.78 (s, 3H), 2.72–2.65 (m, 2H), 1.47 (s, 9H).

(c) 1-[4-[(N-t-butyloxycarbonyl-N-methyl)aminopiperidin-1-yl]-fluoro]aniline (C)

A mixture of nitro compound B, (32.0 g ), 3.2 g of 10% palladium on carbon in 75 ml of methanol was shaken in a Paar shaker flask under 40 Psi hydrogen for 6.0 hr. TLC showed a slower moving spot. The reaction mixture was filtered through celite. Solvent was removed. A dark solid was obtained (28.6 g), it was subjected to next step without further characterisation.

(d) 1-{N-Carbobenzyloxy-[4-[(N-t-butyloxycarbonyl-N-methyl)-peperidin-1-yl]}-3-fluoro]aniline (D)

To the solution of aniline derivative C (19.0 g, 58.823 mmol) in dry tetrahydrofuran (150 ml) was added. Sodium hydrogen carbonate (19.76 g, 235.29 mmol). It was cooled to 0° C. and benzyl chloroformate (12.9 ml, 50% toluene sol.) was added. The whole reaction mixture was stirred at 0° C.-r.t. for 6.0 hr. TLC showed faster moving spot compare to aniline derivative. Reaction mixture was filtered through celite. Solvent removed. Residue was digested with hexane and solvent was removed to give 23.4 g of CBz derivative.

δppm (CDCl$_3$): 7.39–7.28 (m, 6H), 6.99–6.86 (m, 2H), 6.75 (bs, 1H), 5.20 (s, 2H), 4.20 (bs, 1H), 3.43 (d, J=12 Hz, 2H), 2.79 (s, 3H), 2.71 (m, 2H), 1.97–1.86 (m, 2H), 1.49 (s, 9H)

(e) (S)-N-{3-[4-[4-(N-methyl-N-t-butyloxycarbonyl) amino-piperidin-1-yl]-3-fluorophenyl}-2-oxo-oxazolidin-5-yl]methanol (E)

To a solution (200 ml) of CBz derivative in (D; 24.0 g, 52.516 mmol) dry tetrahydrofuran was added. BuLi (67 ml, 157 mmol) at −78° C. under N$_2$. The reaction mixture was stirred at −78° C. for 2.0 hr. Glycidyl butyrate (9.07 g, 62.98 mmol )was then added to the reaction mixture at −78° C. It was stirred at −78° C. for 1 hr. then allowed to reach r.t. TLC of the reaction mixture showed a slower moving spot. Ammonium chloride (30 ml) was added to the reaction mixture. It was stirred for 5 min. Ammonium chloride layer was separated and extracted with ethyl acetate. Tetrahydrofuran and ethyl acetate layer were combined, dried over anhydrous sodium sulphate. Solvent was removed. The residue was purified by column chromatography using CHCl$_3$:MeOH (1.5%–2.5% )as eluent to give 10 g of desired alcohol.

δppm (CDCl$_3$): 7.46 (d, J=8.0 Hz, 1H), 7.10 (d, J=9 Hz, 1H), 6.94 (t, J=9 Hz, 1H) 4.55 (bs, 1H), 4.07–3.87 (m, 5H), 3.74 (bs, 1H), 3.46 (bs, 1H), 3.42 (bs, 1H), 2.78–2.89 (m, 5H), 1.96–1.85 (m, 2H), 1.72 (s, 1H), 1.47 (s, 9H).

(f) (S)-N-{3-[4-[4-(N-Methyl-N-t-butyloxycarbonyl) aminopiperidin-1-yl]-3-fluorophenyl}-2-oxo-oxazolidine-5-yl}methyl methane sulfonate (F)

To a solution of hydroxymethyl compounds (E, 24 g, 56.73 mmol) in dichloromethane (400 ml) was added triethylamine (11.46 g, 113.46 mmol) followed by methane sulphonyl chloride at 0° C. The reaction mixture was stirred at 0° C.-r.t. for 3.0 hr. TLC of the reaction mixture showed a faster moving spot. The reaction mixture was poured in to water and extracted with dichloromethane, washed with saturated sodium bicarbonate solution and then with water. Organic layer was dried over anhydrous sodium sulphate and solvent was removed to give 28.4 g of compound (F).

δppm (CDCl$_3$): 7.45 (d, J=12 Hz, 1H), 7.10–7.01 (m, 2H), 4.92 (bs, 1H), 4.53–4.40 (m, 2H), 4.12(t, J=9 Hz, 1H), 7.10–7.01 (m, 2H), 4.12 (t, J=9 Hz, 1H), 3.94–3.89 (m, 1H), 3.48 (d, J=12 Hz, 2H), 3.15 (m, 1H), 3.11 (s, 3H) 2.79 (s, 3H), 1.97–193 (m, 2H), 1.77–1.69 (m, 4H), 1.48 (s, 9H).

(g) (S)-N-{3-[4-[4-(N-Methyl-N-t-butyloxycarbonyl) aminopiperidin-1-yl)-3-fluorophenyl]-3-fluorophenyl]-2-oxo-oxazolidin-5-yl}methyl azide (G)

To the solution of mesyl derivative (F, 28.4 g, 56.68 mmol) in dimethyl formamide (350 ml) was added sodium azide (11.059, 70.05 mmol). The whole reaction mixture was heated at 80° C. for 9.0 hr. TLC showed a faster moving spot. Reaction mixture was filtered. Dimethyl formamide was removed in reduced pressure. The residue was digested in hexan to afford desired azide in 26.0 g.

δppm (CDCl$_3$): 7.44 (d, 12 Hz, 1H), 7.11 (bs, 1H), 6.97 (t, j=9 Hz, 1H), 4.78 (bs, 1H), 4.09–3.49 (m, 7H), 2.90 (s, 3H), 2.75 (bs, 2H) 1.49 (s, 9H).

(h) (S)-N-{3-[4-[4-(N-Methyl-N-t-butyloxycarbonyl) aminopiperidin-1-yl)-3-fluorophenyl]-2-oxo-oxazolidin-5-yl}methyl amine (H).

To the solution of azido compound (G, 25.5 g, 56.92 mmol) in methanol (50 ml) was added, 10% Pd/c (2.5 g). The whole reaction mixture was hydrgogenated for 10 hr. at 40 Psi. TLC showed a slower moving spot. It was filtered through celite bed and solvent was removed to give desired product of 24.5 g.

δppm (CDCl$_3$):: 7.45 (d, J=12 Hz, 1H), 7.11 (d, J=9 Hz, 1H), 6.94 (t, J=9 Hz, 1H) 4.66 (bs, 1H), 4.00 (t, J=9 Hz, 1H), 3.81 (t, J=9 Hz, 1H), 3.45 (d, J=9 Hz, 2H), 3.10–2.90 (m, 1H), 2.78 (3 3H), 2.73 (bs, 1H), 1.48 (s, 9H).

(i) (S)-N-{3-[4-[4-(N-Methyl,N-1-butyloxycarbonyl) aminopiperidin-1-yl)-3-fluorophenyl]-2-oxo-oxazolidin-5-yl}methyl acetamide. (I)

To a solution of methyl amino derivative (7.0 g, 16.58 mmol) in dichloro methane (120 ml) was added triethyl amine (2.18 g; 21.58 mmol) reaction mixture was cooled to 0° C. and acetic anhydride was added slowly. It was stirred at 0°-r.t. for 5.0 hr. TLC showed a faster moving spot. Reaction mixture was poured into water and extracted with dichloromethane. Organic layer was washed with sodium bicarbonate, brine and water. Organic layer was dried over anhydrous sodium sulphate and solvent was removed to give 7.1 g of crude desired product which on purification gave 4.1 g of pure product.

δppm (CDCl$_3$): 7.43 (d, J=12 Hz, 1H), 7.07 (d, J=9 Hz, 1H), 6.95 (t, J=9 Hz, 1H) 6.28 (bs, 1H), 4.00 (t, J=9 Hz, 1H), 3.78–3.62 (m, 3H), 3.47 (d, J=9 Hz, 2H), 2.80 (s, 3H), 2.75–2.71 (m 2H), 2.03 (s, 3H), 1.49 (s, 9H).

(j) (S)-N-[3-[4-[4-N-methyl)aminopiperidin-1-yl]-3-fluorophenyl}-2-oxo-oxazolidin-5-yl]methyl acetamide. (J)

To a solution of Boc protected compound (I, 2.0 g, 4.31 mmol) in dichloro-methane (35 ml) was added trifluoroacetic acid (5 ml) at 0° C. The whole reaction mixture was stirred at 0° r.t. for 3 hr. TLC of the reaction mixture showed a slower moving spot. Solvent was removed and the residue was dissolved in acetone, anhydrous pot. Carbonate was added to neutralize trifluoro acetic acid. It was stirred at r.t. for 2.0 min. then filtered through a Buckner funnel. Solvent was removed and the title compound was obtained. Yield: 1.5 g Compound No. 41: (S)-N-[[3-[4-[4-(N-methyl-N-2furyl (5formyl)methyl-aminopiperidine-1-yl]-3-fluorophenyl]-2oxo-oxazolidin-5-yl]methyl]acetamide The title compound was made by using (S)-N-[[3-[4-[4-(N-methyl-)aminopiperidine-1-yl]-3-fluorophenyl]-2oxo-oxazolidin-5-yl]methyl]acetamide and 5-chloromethyl-2-furfural following Method A.

Compound No. 42: (S)-N-[[3-[4-[4-(N-methyl-N-(3,5-difluorobenzoyl)aminopiperidine-1-yl]-3-fluorophenyl]-2oxo-oxazolidin-5-yl]methyl]acetamide.

The title compound was made using (S)-N-[[3-[4-[4-(N-methyl-)aminopiperidine-1-yl]-3-fluorophenyl]-2oxo-oxazolidin-5-yl]methyl]acetamide and 3,5, difluoro benzoyl chloride following Method A.

Compound No. 43: (S)-N-[[3-[4-[4-(N-methyl-N-(5-bromo-2-furoyl)aminopiperidine-1-yl]-3-fluorophenyl]-2oxo-oxazolidin-5-yl]methyl]acetamide The title compound was made using (S)-N-[[3-[4-[4-(N-methyl-)aminopiperidine-1-yl]-3-fluorophenyl]-2oxo-oxazolidin-5-yl]methyl]acetamide and 5-bromo-2-furoyl chloride following Method A.

Compound No. 44: (S)-N-[[3-[4-[4-(N-methyl-N-(5-nitro-2-furoyl)aminopiperidine-1-yl]-3-fluorophenyl]-2oxo-oxazolidin-5-yl]methyl]acetamide The title compound was made using (S)-N-[[3-[4-[4-(N-methyl-)aminopiperidine-1-yl]-3-fluorophenyl]-2oxo-oxazolidin-5-yl]methyl]acetamide and 5-nitro-2-furoyl chloride following Method A.

Compound No. 45: (S)-N-[[3-[4-[4-(N-methyl-N-3-furoyl)aminopiperidine-1-yl]-3-fluorophenyl]-2oxo-oxazolidin-5-yl]methyl]acetamide.

The title compound was made using (S)-N-[[3-[4-[4-(N-methyl-)aminopiperidine-1-yl]-3-fluorophenyl]-2oxo-oxazolidin-5-yl]methyl]acetamide and 3-furoyl chloride using Method A.

Compound No. 46: (S)-N-{3-[4-[4-(N-methyl, N-2-furoyl)aminopiperidine-1-yl]-3-fluorophenyl]-2oxo-oxazolidin-5-yl methyl]acetamide The title compound was made using (S)-N-[[3-[4-[4-(N-methyl-)aminopiperidine-1-yl]-3-fluorophenyl]-2oxo-oxazolidin-5-yl]methyl]acetamide and 2-furoyl chloride following Method A.

Compound No. 47: (S)-N-{3-[4-[4-(N-methyl,2-thiopheneacetyl)aminopiperidine-1-yl]-3-fluorophenyl]-2oxo-oxazolidin-5-yl methyl]acetamide The title compound was made using (S)-N-[[3-[4-[4-(N-methyl-)aminopiperidine-1-yl]-3-fluorophenyl]-2oxo-oxazolidin-5-yl]methyl]acetamide and 2-thiophene acetyl-chloride chloride following Method A.

Method-B:

General procedure was same as described earlier in section (Method B) for Compound No.15, only the amine of Formula V is (S)-N-[[3-[4-[4-(N-methyl-)aminopiperidine-1-yl]-3-fluorophenyl]-2oxo-oxazolidin-5-yl]methyl] acetamide (core IV).

Compound No. 48: (S)-N-[[3-[4-[4-(N-methyl-N-2furylmethyl) aminopiperidine-1-yl]-3-fluorophenyl]-2oxo-oxazolidin-5-yl]methyl]acetamide The title compound was made using (S)-N-[[3-[4-[4-(N-methyl-)aminopiperidine-1-yl]-3-fluorophenyl]-2oxo-oxazolidin-5-yl]methyl]acetamide and furan-2-carboxaldehyde following Method B.

Compound No. 49: (S)-N-[[3-[4-[4-(N-methyl-N-3-furyl) aminopiperidine-1-yl]-3-fluorophenyl]-2oxo-oxazolidin-5-yl]methyl]acetamide The title compound was made using (S)-N-[[3-[4-[4-(N-methyl-)aminopiperidine-1-yl]-3-fluorophenyl]-2oxo-oxazolidin-5-yl]methyl]acetamide and furan-3-carboxaldehyde following Method B.

Compound No. 50: (S)-N-[[3-[4-[4-(N-methyl-N-2-furyl(5-nitro)methyl)-aminopiperidine-1-yl]-3-fluorophenyl]-2oxo-oxazolidin-5-yl]methyl]acetamide The title compound was made using (S)-N-[[3-[4-[4-(N-methyl-)aminopiperidine-1-yl]-3-fluorophenyl]-2oxo-oxazolidin-5-yl]methyl]acetamide and 5-nitrofuran-2-carboxaldehyde using Method B.

δppm (CDCl$_3$): 7.40(d, 1H), 7.29 (m, 1H), 7.29 (m, 1H), 7.05 (dd, 1H), 6.92 (t, 1H), 6.48 (d, 1H), 6.26 (bs, 1H), 4.76 (bs, 1H), 4.01 (t, 1H), 3.77–3.60 (m, 5H), 3.47 (d, 2H), 2.66 (t, 3H), 6.26 (bs, 1H), 4.76 (bs, 1H), 4.01 (t, 1H), 3.77–3.60 (m, 5H), 3.47 (d, 2H), 2.66 (t, 3H), 6.26 (bs, 1H), 4.76 (bs, 1H), 4.01 (t, 1H), 3.77–3.60 (m, 5H), 3.47 (d, 2H), 2.66 (5, 3H), 2.37 (s, 3H), 2.01 (s, 3H0, 1.93–1.25 (m, 4H).

Compound No. 51: (S)-N-[[3-[4-[4-(N-methyl-N-2-thienyl (5-nitro)methyl)-aminopiperidine-1-yl]-3-fluorophenyl]-2oxo-oxazolidin-5-yl]methyl]acetamide The title compound was made using (S)-N-[[3-[4-[4-(N-methyl-)aminopiperidine-1-yl]-3-fluorophenyl]-2oxo-oxazolidin-5-yl]methyl]acetamide and 5-nitrothiophen-2-carboxaldehyde following Method B.

δppm (CDCl$_3$): 7.79 (d, 1H), 7.41 (dd, 1H), 7.05 (d, 1H) 6.93 (t, 1H), 6.85 (d, 1H), 6.11 (bs, 1H), 4.01 (t, 1H) 3.82–3.45 (m, 7H), 2.66 (m, 3H), 2.37 (s, 3H), 2.02 (s, 3H), 1.82–1.25 (m, 4H)

Compound No. 52: (S)-N-[[3-[4-[4-(N-methyl-N-2-thienylmethyl)aminopiperidine-1-yl]-3-fluorophenyl]-2oxo-oxazolidin-5-yl]methyl]acetamide The title compound was made using (S)-N-[[3-[4-[4-(N-methyl-)aminopiperidine-1-yl]-3-fluorophenyl]-2oxo-oxazolidin-5-yl]methyl]acetamide and thiophen-2-carboxaldehyde following Method B.

Compound No. 53: (S)-N-[[3-]4-[4-(N-methyl-N-(5-methyl-2-thienyl-methyl)aminopiperidine-1-yl]-3-fluorophenyl]-2oxo-oxazolidin-5-yl]methyl]-acetamide The title compound was made using (S)-N-[[3-[4-[4-(N-methyl-)aminopiperidine-1-yl]-3-fluorophenyl]-2oxo-oxazolidin-5-yl]methyl]acetamide and 5-methyl-thiophen-2-carboxaldehyde following Method B.

Compound No. 54: (S)-N-{3-[4-[4-(N-methyl,2-(5-bromo)thienylmethyl)aminopiperidine-1-yl]-3-fluorophenyl]-2oxo-oxazolidin-5-yl methyl]acetamide The title compound was made using (S)-N-[[3-[4-[4-(N-methyl-)aminopiperidine-1-yl]-3-fluorophenyl]-2oxo-oxazolidin-5-yl]methyl]acetamide and 5-bromo,-thiophen-2-carboxaldehyde Method B.

EXAMPLE 5

Analogues of of (S)-N-[[3-[3[Fluoro-4-(N-1-homopiperazinyl)phenyl]-2-oxo-5-oxazolidinyl] methyl]acetamide (Core V)

The heteroaromatic group with the corresponding appendage can be introduced on the nitrogen atom of ring C of compounds of Formula I by one of the methods described below:

Method-A:

General procedure was same as described earlier in section 7.1.1.1 (Method A) described earlier for Compound No. 1. Only the core amine of Formula V is (S)-N-{3-[4-[4-N-methylaminopeperidin-1-yl]-3-fluorophenyl}-2-oxo-oxazolidin-5-yl]-methyl acetamide (core V).

Compound No. 55: (S)-N[[3-[3-Fluoro-4-[N-1[4-{2-furyl (5- formyl)methyl}]-homopiperazinyl]phenyl]2-oxo-5-oxazolidinyl]methyl]acetamide Preparation of (S)-N-[[3-[3[Fluoro-4-(N-1-homopiperazinyl)phenyl]-2-oxo-5-oxazolidinyl]methyl] acetamide (a) Preparation of 1-(2-Fluoro-4-nitrophenyl) homopiperazine.

To homopiperazine (5 g, 0.05 mol) in acetonitrile (30 mL), 3.4-difluoronitrobenzene (3.17 g, 0.02 mol) was added and the reaction mixture was heated to reflux for 4 hrs. Then the solvent was evaporated and the residue taken in EtOAc and washed with water and brine solution. The EtOAc layer was dried over anhyd $Na_2SO_4$ and evaporated in vacuo. The residue was digested with ether-hexane (1:20), decanted and dried in vacuo to get 3.7 g of final product.

δppm ($CDCl_3$): 7.9 (m, 2H, Ar—H), 6.75 (t, 1H, Ar—H) 3.64 (m, 4H, $CH_2$), 3.08 (m, 2H, $CH_2$), 2.91 (m, 2H, $CH_2$), 1.96 (m, 2H, $CH_2$).

(b) Preparation of 1-(2-Fluoro-4-nitrophenyl)-4-tert-butoxycarbonyl-homopiperazine.

To 1-(2-Fluoro-4-nitrophenyl)homopiperazine (3.5 g, 14.6 mmol) in dichloromethane (100 mL) cooled to 5° C., triethylamine (0.2 mL, 1.46 mmole) and tert-butoxydicarbonate (4.15 g, 19.03 mmol) was added and the reaction mixture was stirred for 18 hrs. The solvent was evaporated and to the residue hexane was added. The product precipitating out was filtered, washed with hexane and dried in air to yield 4.0 g of the final product.

δppm ($CDCl_3$): 7.93 (m, 2H, Ar—H), 6.78 (t, 1H, Ar—H), 3.63 (m, 6H, $CH_2$), 3.43 (m, 2H, $CH_2$), 1.97 (m, 2H, $CH_2$), 1.50 (s, 9H, t-Bu).

(c) 3-Fluoro-4-(N-tert-butoxycarbonylhomopiperazinyl) aniline.

To 1-(2-Fluoro-4-nitrophenyl)4-tert-butoxycarbonylhomopiperazine (3.2 g, 9.4 mmole) in methanol (30 mL), 10% palladium/carbon was added and shaken in a Parr hydrogenation apparatus under 40 psi of hydrogen gas for 3 hrs. Then the reaction mixture was filtered over celite and the filtrate evaporated in vacuum to yield 2.64 g of the final product.

δppm ($CDCl_3$): 6.81 (t, 1H, Ar—H), 6.38 (m, 2H, Ar—H) 3.53 (m, 4H, $CH_2$) 3.21 (m, 4H, $CH_2$), 2.86 (br s, $NH_2$), 1.95 (m, 2H, $CH_2$), 1.45 (s, 9H, t-Bu).

(d) N-Benzyloxycarbonyl-3-fluoro-4-(N-tert-butoxylcarbonylhomopiperazinyl)aniline.

To 3-Fluoro-4-(N-tert-butoxycarbonylhomopiperazinyl) aniline (2.6 g, 8.4 mmol) in THF (25 ml) cooled to 5° C., sodium bicarbonate (0.85 g 10.1 mmol), was added and then benzylchloroformate (1.72 g, 10 mmol) was added dropwise. The reaction mixture was stirred for 18 hrs. at R.T. and then filtered. The filtrate was evaporated in vacuo. The residue was dissolved in dichloromethane and washed with saturated sodium bicarbonate solution and brine water. The organic layer was dried over anhyd $Na_2SO_4$ and evaporated in vacuo to give 5.04 g of final product.

δppm ($CDCl_3$): 7.35 (s, 6H, Ar—H), 6.84 (m, 2H, Ar—H), 6.54 (s, 1H, NH), 5.17 (s, 2H, $CH_2$), 3.2–3.61 (m, 8H, $CH_2$), 1.93 (m, 2H, $CH_2$), 1.45 (s, 9H, t-Bu).

(e) (R)-[N-3-[3-Fluoro-4-[N-1-(4-tert-butoxycarbonyl) homopiperazinyl]phenyl]-2-oxo-5-oxazolidinyl]methanol To N-benzyloxycarbonyl-3-fluoro-4-(N-tert-butoxycarbonylhomopiperazinyl)aniline (2.5 g, 5.6 mmol) dissolved in dry THF(25 mL), cooled to −78° C., butyl lithium(4.8 mL, 15% sol. in hexane, 11.3 mmol) was added under +ve pressure of nitrogen. The reaction mixture was stirred at −78° C. for 1.5 hrs. Then R-glycidyl butyrate (0.89 g, 6.2 mmol) was added and the reaction mixture was stirred at −78° C. for 1 hr and then at R.T. for 18 hrs. To it 25 mL of satd ammonium chloride solution was added and the reaction mixture extracted with EtOAc. The combined organic layers were washed with water and brine water, dried over anhydrous $Na_2SO_4$ and evaporated in vacuo. The crude product (~3 g) was purified by column chromatography (3% MeOH/$CHCl_3$) to yield 0.41 g of final product.

δppm ($CDCl_3$): 7.38 (d, 1H, ArH), 7.04 (d, 1H, Ar—H), 6.87 (t, 1H, Ar—H), 4.72 (m, 1H, CH), 4.1–3.2 (m, 11H, $CH_2$), 2.18 (br s, 1H), 1.94 (m, 2H, $CH_2$), 1.45 (s, 9H, t-Bu).

(f) (R)-[N-3[3-Fluoro-4-[N-1-(4-tert-butoxycarbonyl) homopiperazinyl]phenyl]-2-oxo-5-oxazolidinyl]methyl methanesulfonate.

To the (R)-[N-3[3-Fluoro-4-[N-1-(4-tert-butoxycarbonyl) homopiperazinyl]-phenyl]-2-oxo-5-oxazolidinyl]methanol (1.55 g, 3.8 mmol) in dichloromethane (10 mL) cooled to 5° C., triethylamine (0.76 g, 7.6 mmol) and methanesulfonylchloride (0.6 g, 5.3 mmoles) were added and the reaction mixture was stirred for 1 hr. Then the reaction mixture was diluted with dichloromethane and washed with saturated sodium bicarbonate solution and brine. The organic layer was dried over anhydrous sodium sulfate and evaporated in vacuo to yield 1.39 of product.

δppm ($CDCl_3$): 7.32 (d, 1H, ArH), 7.02 (d, 1H, Ar—H), 6.87 (t, 1H, Ar—H), 4.89 (m, 1H, CH), 4.47 (m, 2H, $CH_2$), 4.09 (t, 1H, CH), 3.89 (m, 1H, CH), 3.65–3.2 (m, 8H, $CH_2$), 3.1 (s, 3H, $CH_3$), 1.94 (m, 2H, $CH_2$), 1.45 (s, 9H, t-Bu).

(g) (R)-[N-3[3-Fluoro-4-[N-1-(4-tert-butoxycarbonyl) homopiperazinyl]phenyl]-2-oxo-5-oxazolidinyl] methylazide.

To (R)-[N-3[3-Fluoro-4-[N-1-(4-tert-butoxycarbonyl) homopiperazinyl]-phenyl]-2-oxo-5-oxazolidinyl] methylmethanesulfonate compound (1.21 g, 2.5 mmoles) in DMF(10 mL), sodium azide (0.81 g, 12 mmoles) was added and the reaction mixture heated to 80° C. for 5 hrs. The solid was filtered off and the filtrate evaporated in vacuo. The residue was dissolved in chloroform and washed with water and brine solution. The organic layer was dried over anhyd. $Na_2SO_4$ and evaporated in vacuo to yield 1.2 g of the product.

δppm ($CDCl_3$): 7.32 (d, 1H, Ar—H), 7.04 (d, 1H, Ar—H), 6.87 (t, 1H, Ar—H), 4.75 (m, 1H, CH), 4.02 (t, 1H, CH), 3.8–3.2(m, 1H, $CH_2$), 1.92 (M, 2H, $CH_2$), 1.45 (s, 9H, t-Bu).

(h) (R)-[N-3-[3-Fluoro-4-[N-1-(4-tert-butoxycarbonyl) homopiperazinyl]phenyl]-2-oxo-5-oxazolidinyl] methylamine.

To (R)-[N-3[3-Fluoro-4-[N-1-(4-tert-butoxycarbonyl) homopiperazinyl]phenyl]-2-oxo-5-oxazolidinyl] methylazide (1.1 g, 2.5 mmol) in methanol (10 mL), 10% palladium/carbon (0.22 g) was added and the reaction mixture shaken in a Parr hydrogenation apparatus under 40 psi hydrogen pressure for 5 hrs. The reaction was filtered over celite and the filtrate evaporated in vacuo to yield 0.9 g of product. The product was used as such in next step without further purification and characterization.

(i) (S)-N-[[3-[3-Fluoro-4-[N-1-(4-tert-butoxycarbonyl) homopiperazinyl]phenyl]2-oxo-5-oxazolidinyl]methyl] acetamide.

To (R)-[N-3-[3-Fluoro-4-[N-1-(4-tert-butoxycarbonyl) homopiperazinyl]phenyl]-2-oxo-5-oxazolidinyl] methylamine (0.77 g, 1.9 mmol) in dichloromethane (10 mL), triethylamine (0.21 g, 2.17 mmol) and acetic anhydride (0.21 g, 2 mmol) were added and the reaction mixture was stirred at R.T. for 30 minutes. Then the reaction mixture was diluted with dichloromethane and washed with saturated sodium bicarbonate solution and brine water. The organic layer was dried over anhydrous sodium sulfate and evaporated in vacuo. The residue was purified by column chromatography (2% MeOH/CHCl$_3$) to yield 0.48 g of final product.

δppm (CDCl$_3$): 7.35(d, 1H, Ar—H), 7.02(d, 1H, Ar—H), 6.86(t, 1H, Ar—H), 5.96(t, 1H, NH), 4.73(m, 1H, CH), 3.99(t, 1H, CH), 3.25–3.8(m, 1H, CH2), 2.01(s, 3H. CH3), 1.95(m, 2H, CH2), 1.44(s, 9H, t-Bu).

(j) (S)-N-[[3-[3Fluoro-4-(N-1-homopiperazinyl)phenyl]-2-oxo-5-oxazolidinyl]methyl acetamide To (S)-N-[[3-[3-Fluoro-4-[N-1-(4-tert-butoxycarbonyl) homopiperazinyl]phenyl]2-oxo-5-oxazolidinyl]methyl] acetamide (0.5 g, 1.11 mmol) in dichloromethane (8 mL), trifluoroacetic acid (2 mL) was added and stirred for 2 hrs. Then the reaction mixture was evaporated and dried in vacuo. To the residue in acetone (10 mL), potassium carbonate (0.78 g, 5.55 mmol) was added and stirred for 15 mts. Then the reaction mixture was fitered and the filtrate evaporated in vacuo to yield the product in quantitative yield. This product was used as such in next step without further characterization.

Compound No. 55: (S)-N[[3-[3-Fluoro-4-[N-1[4-{2-furyl (5-formyl)methyl}]homopiperazinyl]phenyl]2-oxo-5-oxazolidinyl]methyl]acetamide The title compound was made with (S)-N-[[3-[3[Fluoro-4-(N-1-homopiperazinyl)phenyl]-2-oxo-5-oxazolidinyl] methyl acetamide and 2-formyl-5-chloromethylfuran using Method A.

δppm (CDCl$_3$): 9.61(s, 1H, CHO), 7.35(d, 1H, Ar—H), 7.2(d, 1H, Ar—H), 7.02(d, 1H, Ar—H), 6.83(t, 1H, Ar—H), 6.48(s, 1H, Ar—H), 5.96(t, 1H, NH), 4.72(m, !H, CH), 4.71(t, 1H, Ar—H), 4.14 (s, 1H, CH$_2$), 3.2–3.8(m., 7H, CH$_2$), 2.8–3(m, 4H, CH$_2$), 2.09(m, 5H, CH$_2$, CH$_3$)

Compound No. 56: (S)-N[[3-[3-Fluoro-4-[N-1[4-(2-thienylacetyl)]homopiperazinyl]phenyl]2-oxo-5-oxazolidinyl]methyl]acetamide The title compound was made with (S)-N-[[3-[3[Fluoro-4-(N-1-homopiperazinyl)phenyl]-2-oxo-5-oxazolidinyl] methyl]acetamide and 2-thiophenacetylchloride using Method A.

δppm (CDCl$_3$): 7.34(m, 1H, Ar—H), 7.18(t, 1H, Ar—H), 7.2–6.78(m, 4H, Ar—H), 6.22(t, 1H, NH), 4.74(m, 1H, CH), 4.2–3.52(m, 10H, CH$_2$), 3.52–3.15(m, 4H, CH$_2$), 2.01(m, 5H, CH$_2$, CH$_3$)

Compound No. 57: (S)-N[[3-[3-Fluoro-4-[N-1[4-{2-thienyl (5-nitro)methyl}]homopiperazinyl]phenyl]2-oxo-5-oxazolidinyl]methyl]acetamide The title compound was made with (S)-N-[[3-[3[Fluoro-4-(N-1-homopiperazinyl)phenyl]-2-oxo-5-oxazolidinyl] methyl acetamide and 5-nitro-2-thiophencarboxaldehyde using Method B.

δppm (CDCl$_3$): 7.78(s, 1H, Ar—H), 7.35(d, 1H, Ar—H), 7.04(m, 1H, Ar—H), 6.87(m, 2H, Ar—H), 5.99(t, 1H, Ar—H), 4.75(m, 1H, CH), 4.0(t, 1H, CH), 3.85(s, 2H, CH$_2$), 3.52–3.8(m, 3H, CH$_2$), 3.42(m, 4H, CH$_2$), 2.9–2.75(m, 4H, CH$_2$), 2.01(m, 5H, CH$_2$, CH$_3$)

Compound No. 58: (S)-N[[3-[3-Fluoro-4-[N-1[4-(3-furylmethyl)]homopiperazinyl]phenyl]2-oxo-5-oxazolidinyl]methyl]acetamide The title compound was made with (S)-N-[[3-[3[Fluoro-4-(N-1-homopiperazinyl)phenyl]-2-oxo -5-oxazolidinyl] methyl]acetamide and 3-furaldehyde using Method B.

δppm (MeOD): 7.71 (s, 1H, Ar—H), 7.59(s, 1H, Ar—H), 7.45(d, 1H, Ar—H), 7.12(d, 1H, Ar—H), 7.01(t, 1H, Ar—H), 6.6(s, 1H, Ar—H), 4.53(m, 8H, CH2), 4.1(m, 2H, CH2), 3.77(t, 1H, CH), 3.75–3.45(m, 5H, CH2), 2.19(m, 2H, CH2), 1.96(s, 3H, CH3)

Scheme-II

Compound No. 59: Preparation of (S)-N-[[3-[3-fluoro-4-[N-1{2-furyl-[4-(5-difluoromethyl)methyl}]piperazinyl]-2-oxo-5-oxazolidinyl]-methyl]acetamide To a solution of (S)-N-[[3-Fluoro-4-[N-1[4-{2-furyl(5-formyl)methyl}]piperazinyl]phenyl]-2-oxo-5-oxazolidinyl] methyl]acetamide (80 mg, 0.18 mmol) in dichloromethane (4.0 ml) was added diethylamino sulfurtrifluoride (58 mg, 0.35 mmol). The whole reaction mixture was stirred at r.t. for 12 hr. TLC of the reaction mixture showed a faster moving spot. It was poured into water and extracted with dichloromethane. Dichloromethane layer was washed with water, dried over anhydrous sodium sulphate. Solvent was removed. A gummy compound (60 mg) was obtained.

δppm (CDCl$_3$): 7.44 (d, 1H), 7.05 (d, 1H), 6.92 (t, 1H) 6.62 (m, 2H), 6.36 (m, 1H), 6.12 (bs, 1H), 4.60 (bs, 1H), 3.24–2.95(m, 6H), 2.74), 2.74 (bs, 4H) 4.01 (m, 1H) 3.68 (m, 3H), 2.00 (s, 3H).

Compound No. 74: Preparation of (S)-N-[[3-[3-fluoro-4-[N-1{2-furyl-[4-(5-fluoromethyl)methyl}]piperazinyl]-2-oxo-5-oxazolidinyl]-methyl]acetamide The title compound was made by reacting from (S)-N-[[3-[3-Fluoro-4-[N-1{2-furyl-[4-(5-hydroxymethyl) methyl}]piperazinyl]-2-oxo-5-oxazolidinyl]methyl] acetamide using the procedure described for Compound No. 59.

Compound No. 60: (S)-N-[[3-[3-Fluoro-4-[N-1-[4-(2-furyl-(5-aldoxime)methyl}]piperazinyl]phenyl]-2-oxo-5-oxazolidinyl]methyl]acetamide.

To a solution of 5-formyl furyl derivative (140 mg 0.31 mmol) in dry pyridine was added hydroxylamine hydrochloride (26 mg, 0.38 mmol). The whole reaction mixture was stirred at 25° C. for 4.0 hr. TLC of the reaction mixture was monitored. A slower moving spot was observed compare to starting compound. Pyridine was removed under reduced pressure and traces of pyridine were removed with toluene to yield title compound of 140 mg.

δppm $^1$HNMR (DMSO-d$^6$): 8.70(d, 2H), 8.08–8.03(m, 1H), 7.65–7.61 (m, 1H), 7.78 (d, 1H), 7.24 7.11 (m, 2H), 4.70 (d, 1H) 4.49 (s, 2H), 4.07 (t, 1H), 1.82 (s, 3H), 3.72 (m, 2H), 3.53–2.88 (m, 9H).

Compound No. 61: (S)-N-[[3-[3-Fluoro-4-[N-1[4-{2-furyl (5-aldoxime(methyl-4-(N-carboxyaminophenylacetate) methyl}]piperazinyl]phenyl]-2-oxo-5-oxazolidinyl]methyl] acetamide The title compound was prepared by using the procedure mentioned above for Compound No.60.

Compound No. 62: (S)-N-[[3-[3-Fluoro-4[N-1-[4-{2-furyl-(5-hydrazone)-methyl}]-piperazinyl]-phenyl]-2-oxo-5-oxazolidinyl]-methyl]acetamide To a solution of 5-formyl furyl derivative (140 mg, 0.31 mmol) in ethanol (4.0 ml) was added hydrazine hydrate (100 mg) and catalytic amount of conc. sulfuric acid. The whole reaction mixture was stirred at 25° C. for 48 hr. TLC of the reaction mixture showed no changes. Stirring was continued for another 12 hr. no change in TLC was observed.

Solvent was evaporated to dryness and the solid residue was digested with ether to give 100 mg of title compound of m.p. 78–181° C.

δppm (CDCl$_3$): δ=7.61 (s, 1H), 7.42 (dd, 1H), 7.04 (t, 1H), 6.92 (t, 1H), 6.44 (d, 1H), 6.28 (bs, 2H), 5.60 (bs, 2H), 4.77 (bs, 1H), 4.02 (t, 1H), 3.77–3.61 (m, 8H), 3.10 (bs, 1H), 2.71 (bs, 1H), 2.02 (s, 3H).

Compound No. 63: Preparation of (S)-N-[[3-[3-Fluoro-4-[N-1{2-furyl-[4-(5-hydroxymethyl)methyl}]piperazinyl]-2-oxo-5-oxazolidinyl]methyl]acetamide To a solution 5-formyl-2-derivative (100 mg, 0.22 mmol) in ethanol was added Sodium borohydride (solid, 17 mg, 0.44 mmol). The whole reaction mixture was stirred at 25° C. for 60 hr. TLC of the reaction mixture in chloroform-:methanol (9:1) showed a slower moving spot. The solvent was removed under reduced pressure. The residue was dissoved in chloroform and washed with water, dried over anhydrous sodium sulphate and solvent was removed to give title compound in 70 mg as gum.

δppm (CDCl$_3$): 745 (d, 1H), 7.06, (d, 1H), 6.94 (d, 1H), 6.23 (dd, 1H), 6.00 (bs, 1H), 4.70 (bs, 1H), 4.03 (t, 1H), 3.12 (bs, 4H), 2.69 (bs, 4H), 4.62 (s, 2H), 3.76–3.4 (m, 6H), 2.03 (s, 3H).

Compound No. 64: (S)-N-[[3-[3-Fluoro-4-[N-1[4-{2-furyl(5-cyano)methyl}]piperazinyl]phenyl]-2-oxo-5-oxazolidinyl]methyl]acetamide (S)-N-[[3-[3-Fluoro4-[N-1[4-{2-furyl(5-aldoxime)methyl}]piperazinyl]phenyl]-2-oxo-5-oxazolidinyl]methyl]acetamide (6126, 3.5 g, 0.76 mmol) was taken in CH$_2$Cl$_2$ (5 mL) and triethyl amine(1.5 g, 1.5 mmol) was added and the r.m. was maintained at −78° C. Triflic anhydride (4.3 g, 1.5 mmol) in CH$_2$Cl$_2$ (2 mL) was added dropwise after complete addition, the temperature of the reaction mixture was allowed to rise to r.t. in 2 hrs. The r.m. is concentrated under vacuum. H$_2$O (10 mL) was added and extracted with CH$_2$Cl$_2$ (3×10 mL). The combined organic layer was dried over Na$_2$SO$_4$, filtered and concentrated to obtain the title compound.

NMR(CDCl3); 7.44–6.10(m, 6H), 4.74(m, 1H), 4.00(t, 2H), 3.73–3.62(m, 5H), 3.09–2.68 (m, 8H, ), 2.01(s, 3H)

Compound No. 65: (S)-N-[[3-Fluoro-4-[N-1[4-{2-furyl(5-carboxy)methyl}]-piperazinyl]phenyl]-2-oxo-5-oxazolidinyl]methyl]acetamide The title compound was made using (S)-N-[[3-Fluoro4-[N-1[4-{2-furyl(5-formyl)methyl}]piperazinyl]phenyl]-2-oxo-5-oxazolidinyl]methyl]acetamide in a solution of freshly prepared Ag$_2$O and stirring for 30 min. The r.m. was filtered, acidified to pH 5 and extracted with EtOAc, dried over Na2SO4, filtered and concentrated.

δppm (CDCl$_{3+}$ MeOD) 8.01–7.03 (m, 5H), 4.81 (m, 1H), 4.07 (t, 1H), 3.8–3.3v (m, 5H), 3.0(s, 4H), 2.7 (s, 4H) 2.01(s, 3H).

Compound No. 66: (S)-N-[[3-Fluoro-4-[N-1[5-(1,3-dioxane)-2-furylmethyl]piperazinyl]phenyl]-2-oxo-5-oxazolidinyl]methyl]acetamide The title compound was made using (S)-N-[[3-Fluoro-4-[N-1[4-{2-furyl(5-formyl)methyl }]piperazinyl]phenyl]-2-oxo-5-oxazolidinyl]methyl]acetamide with 1,3-propane diol and BF$_3$ etherate using standard literature procedures.

Compound No. 67: (S)-N-[[3-Fluoro-4-[N-1[5-(formamido)-2-furylmethyl]-piperazinyl]phenyl]-2-oxo-5-oxazolidinyl]methyl]acetamide The title compound was made reacting (S)-N-[[3-Fluoro-4-[N-1[4-(2-furyl-(5-carboxyethyl)methyl)piperazinyl]phenyl]-2-oxo-5-oxazolidinyl]methyl]acetamide with aqueous ammonia solution followed by wet extraction with ethyl acetate.

δppm (CDCl$_{3+}$ DMSO-d6) 7.46–6.37 (m, 6H), 4.7 (m, 1H), 4.0–3.4 (m, 5H), 2.9 (s, 4H), 2.4 (s, 4H), 2.01 (s, 3H).

Compound No. 68: (S)-N-[[3-Fluoro-4-[N-1[5-(morpholine-1-carbonyl)-2-furyl-methyl]piperazinyl]phenyl]-2-oxo-5-oxazolidinyl]methyl]acetamide The title compound was made by reacting (S)-N-[[3-Fluoro-4-[N-1[4-(2-furyl-(5-carboxyethyl)methyl)piperazinyl]phenyl]-2-oxo-5-oxazolidinyl]methyl]acetamide with morpholine using standard literature procedure.

Compound No. 69: (S)-N-[[3-Fluoro-4-[N-1[5-(4-(tertbutoxycarbonyl)aminopiperidine)-2-furylmethyl]piperazinyl]phenyl]-2-oxo-5-oxazolidinyl]methyl]acetamide The title compound was made by reacting (S)-N-[[3-Fluoro4-[N-1[4-(2-furyl-(5-carboxy)methyl)piperazinyl]phenyl]-2-oxo-5-oxazolidinyl]methyl]acetamide with thionyl chloride and 4-(tertbutoxycarbonyl)amino piperidine.

While the present invention has been described in terms of its specific embodiments, certain modifications and equivalents will be apparent to those skilled in the art and are intended to be included within the scope of the present invention.

What is claimed is:

1. A compound selected from the group consisting of
(S)-N-[[3-[3-Fluoro-4-[N-1-[4-(2-furoyl)piperazinyl]]phenyl]-2-oxo-5-oxazolidinyl]methyl]acetamide
(S)-N-[[3-[3-Fluoro-4-[N-1[4-{2-furyl(5-formyl)methyl}]piperazinyl]phenyl]-2-oxo-5-oxazolidinyl]methyl]acetamide
(S)-N-[[3-Fluoro-4-[N-1[4-(2-furyl-(5-carboxyethyl)methyl)piperazinyl]phenyl]-2-oxo-5-oxazolidinyl]methyl]acetamide
(S)-N-[[3-Fluoro-4-[N-1[4-(5-bromo-2-furoyl)]piperazinyl]phenyl]-2-oxo-5-oxazolidinyl]methyl]acetamide
(S)-N-[[3-Fluoro-4-[N-1[4-(5-chloromethyl-2-furoyl)piperazinyl]phenyl]-2-oxo-5-oxazolidinyl]methyl]acetamide
(S)-N-[[3-Fluoro-4-[N-1[4-(5-nitro-2-furoyl)piperazinyl]phenyl]-2-oxo-5-oxazolidinyl]methyl]acetamide
(S)-N[[3-[3-Fluoro-4-[N-1[4-{2-(2-thienyl)dicarbonyl}]piperazinyl]phenyl]2-oxo-5-oxazolidinyl]methyl]acetamide
(S)-N[[3-[3-Fluoro-4-[N-1[4-(3-furoyl)]piperazinyl]phenyl]2-oxo-5-oxazolidinyl]methyl]acetamide
(S)-N[[3-[3-Fluoro-4-[N-1[4-{2-furyl(5-bromo)methyl}]piperazinyl]phenyl]2-oxo-5-oxazolidinyl]methyl]acetamide
(S)-N[[3-[3-Fluoro-4-[N-1[4-{2-thienyl(5-chloro)methyl}]piperazinyl]phenyl]2-oxo-5-oxazolidinyl]methyl]acetamide
(S)-N[[3-[3-Fluoro-4-[N-1[4-(2-furylmethyl)]piperazinyl]phenyl]2-oxo-5-oxazolidinyl]methyl]acetamide
(S)-N-[[3-[3-Fluoro-4-[N-1[4-(2-thienylmethyl)]piperazinyl]phenyl]-2-oxo-5-oxazolidinyl]methyl]acetamide
(S)-N[[3-[3-Fluoro-4-[N-1[4-(2-thienylacetyl)]piperazinyl]phenyl]2-oxo-5-oxazolidinyl]methyl]acetamide
(S)-N-[[3-[3-Fluoro-4-[N-1[4-{2-thienyl(4-bromo)methyl}]piperazinyl]phenyl]-2oxo-5-oxazolidinyl]methyl]acetamide (S)-N-[[3-[3-fluoro-4-[N-1-[4-{2-furyl-(5-nitro)methyl}] piperazinyl]phenyl]-2-oxo-5-oxazolidinyl]methyl] acetamide Hydrochloric salt of (S)-N-[[3-Fluoro-4-[N-1[4-{2-furyl (5-nitro)methyl}]piperazinyl]phenyl]-2-oxo-5-oxazolidinyl]methyl]acetamide Citrate salt of (S)-N-[[3-Fluoro-4-[N-1[4-{2-furyl(5-nitro)methyl}]piperazinyl]phenyl]-2-oxo-5-oxazolidinyl]methyl]acetamide (S)-N[[3-[3-Fluoro-4-[N-1[4-(2-pyrrolylmethyl)] piperazinyl]phenyl]2-oxo-5-oxazolidinyl]methyl] acetamide (S)-N[[3-[3-Fluoro-4-[N-1[4-{2-thienyl(3-methyl) methyl}]piperazinyl]phenyl]2-oxo-5-oxazolidinyl] methyl]acetamide (S)-N[[3-[3-Fluoro-4-[N-1[4-(3-furylmethyl)] piperazinyl]phenyl]2-oxo-5-oxazolidinyl]methyl] acetamide (S)-N[[3-[3-Fluoro-4-[N-1[4-{2-thienyl(5-methyl) methyl}]piperazinyl]phenyl]2-oxo-5-oxazolidinyl] methyl]acetamide (S)-N[[3-[3-Fluoro-4-[N-1[4-{2-pyrrole(1-methyl) methyl}]piperazinyl]phenyl]2-oxo-5-oxazolidinyl] methyl]acetamide (S)-N[[3-[3-Fluoro-4-[N-1[4-{2-thienyl(5-nitro)methyl}] piperazinyl]phenyl]2-oxo-5-oxazolidinyl]methyl] acetamide (S)-N[[3-[3-Fluoro-4-[N-1[4-[2-furyl{5-(N-thiomorpholinyl)methyl}methyl]piperazinyl]phenyl]2-oxo-5-oxazolidinyl]methyl]acetamide (S)-N[[3-[3-Fluoro-4-[N-1[4-[2-furyl{5-(N-morpholinyl)methyl}methyl]]piperazinyl]phenyl]2-oxo-5-oxazolidinyl]methyl]acetamide (S)-N-[[3-Fluoro-4-[N-1[4-{2-furyl(5-acetoxymethyl) methyl}]piperazinyl]phenyl]-2-oxo-5-oxazolidinyl] methyl]acetamide (S)-N-[[3-Fluoro-4-[N-1[4-{2-thienyl(5-bromo)methyl}] piperazinyl]phenyl]-2-oxo-5-oxazolidinyl]methyl] acetamide (S)-N-[[3-Fluoro-4-[N-1[4-(5-nitro-2-furylmethyl) piperazinyl]phenyl]-2-oxo oxazolidinyl]methyl] dichloroacetamide (S)-N[[3-[3-Fluoro-4-[N-1[4-(5-nitro-2-thienoyl)] piperazinyl]phenyl]2-oxo-5-oxazolidinyl]methyl] acetamide hydrochloride (S)-N[[3-[3-Fluoro-4-[N-1[4-(2',2'-diphenyl-2'hydroxy acetyl)]piperazinyl]phenyl]2-oxo-5-oxazolidinyl] methyl]acetamide (S)-N-[[3-[3-fluoro-4-[N-1{2-furyl-[4-(5-difluoromethyl)methyl]piperazinyl]-2-oxo-5-oxazolidinyl]-methyl]acetamide (S)-N-[[3-[3-Fluoro-4-[N-1-[4-(2-furyl-(5-aldoxime) methyl}]piperazinyl]phenyl]-2-oxo-5-oxazolidinyl] methyl]acetamide (S)-N-[[3-[3-Fluoro-4-[N-1[4-{2-furyl(5-aldoxime (methyl-4-(N-carboxyaminophenyl acetate)methyl}] piperazinyl]phenyl]-2-oxo-5-oxazolidinyl]methyl] acetamide (S)-N-[[3-[3-Fluoro-4[N-1-[4-{2-furyl-(5-hydrazone)-methyl}]-piperazinyl]-phenyl]-2-oxo-5-oxazolidinyl]-methyl]acetamide (S)-N-[[3-[3-fluoro-4-[N-1{2-furyl-[4-(5-difluoromethyl)methyl}]piperazinyl]-2-oxo-5-oxazolidinyl]-methyl]acetamide (S)-N-[[3-[3-Fluoro-4-[N-1-[4-(2-furyl-(5-aldoxime) methyl}]piperazinyl]phenyl]-2-oxo-5-oxazolidinyl] methyl]acetamide (S)-N-[[3-[3-Fluoro-4-[N-1[4-{2-furyl(5-aldoxime (methyl-4-(N-carboxyaminophenyl acetate)methyl}] piperazinyl]phenyl]-2-oxo-5-oxazolidinyl]methyl] acetamide (S)-N-[[3-[3-Fluoro-4[N-1-[4-{2-furyl-(5-hydrazone)-methyl}]-piperazinyl]-phenyl]-2-oxo-5-oxazolidinyl]-methyl]acetamide (S)-N-[[3-[3-Fluoro-4-[N-1{2-furyl-[4-(5-hydroxymethyl)methyl}]piperazinyl]-2-oxo-5-oxazolidinyl]methyl]acetamide (S)-N-[[3-[3-Fluoro-4-[N-1[4-{2-furyl(5-cyano)methyl}] piperazinyl]phenyl]-2-oxo-5-oxazolidinyl]methyl] acetamide (S)-N-[[3-Fluoro-4-[N-1[4-{2-furyl(5-carboxy)methyl}] piperazinyl]phenyl]-2-oxo-5-oxazolidinyl]methyl] acetamide (S)-N-[[3-Fluoro-4-[N-1[5-(1,3-dioxane)-2-furylmethyl] piperazinyl]phenyl]-2-oxo-5-oxazolidinyl]methyl] acetamide (S)-N-[[3-Fluoro-4-[N-1[5-(formamido)-2-furylmethyl] piperazinyl]phenyl]-2-oxo-5-oxazolidinyl]methyl] acetamide (S)-N-[[3-Fluoro-4-[N-1[5-(morpholine-1-carbonyl)-2-furylmethyl]piperazinyl]phenyl]-2-oxo-5-oxazolidinyl]methyl]acetamide (S)-N-[[3-Fluoro-4-[N-1[5-(4-(tert butoxy carbonyl) amino piperidine)-2-furylmethyl]piperazinyl]phenyl]-2-oxo-5-oxazolidinyl]methyl]acetamide (S)-N-[[3-Fluoro-4-[N-1[4-{(Z)-2-methoxyimino-2-(2-furyl)acetyl}]piperazinyl]phenyl]-2-oxo-5-oxazolidinyl]methyl]acetamide.

2. A pharmaceutical composition comprising a compound of claim 1 and a pharmaceutically acceptable carrier.

3. A pharmaceutical composition comprising a pharmaceutically effective amount of a compound according to claim 1, or a physiologically acceptable acid addition salt thereof, with a pharmaceutically acceptable carrier, for treating microbial infections.

4. A method of treating or preventing microbial infections in a mammal comprising administering to said mammal the pharmaceutical compositions of claim 2 or 3.

* * * * *

UNITED STATES PATENT AND TRADEMARK OFFICE
CERTIFICATE OF CORRECTION

PATENT NO.        : 6,956,040 B2
APPLICATION NO. : 10/051784
DATED             : January 17, 2002
INVENTOR(S)       : Anita Mehta et al.

It is certified that error appears in the above-identified patent and that said Letters Patent is hereby corrected as shown below:

Title page, Title – "piperazinyl" needs to be removed

Title page, Other publications, Line 1 – "Medicianl Chemistry" should read --Medicinal Chemistry--

Title page, Other publications, Line 21 – "Comparitave" should read --Comparative--

Title page, item (74) – "George F. Heibel, Esq." should read --George E. Heibel, Esq.--

Column 7, Line 27 – "(R6,R7)" should read --(R6, R7)--

Column 18, Line 17 – "Citrate slat" should read --Citrate salt--

Column 25, Line 47 – "(1a, 5a, 6a)" should read --(1α, 5α, 6α)--

Column 27, Line 23 – "cetamide" should read --acetamide--

Column 29, Line 7 – "Compound No. 15" should read --Compound No. 17--

Column 29, Line 16 – "(br s," should read --(br, s,--

Column 29, Line 16 – "H)." should read --H),--

Column 31, Line 15 – "yied" should read --yield--

Column 32, Line 46 – "so" should read --solid--

Column 35, Line 65 – "tat" should read --that--

Column 36, Line 6 – "Nethyl" should read --N-Methyl--

Column 36, Line 30 – "CH2Cl2" should read --$CH_2Cl_2$--

Column 39, Line 31 – "J=12H" should read --J=12Hz--

Column 40, Line 29 – "-193" should read -- -1.93--

Column 40, Line 55 – "(3 3H)" should read --(t, 3H)--*

Column 40, Line 56 – "Methyl, N-1" should read --Methyl-N-1--

UNITED STATES PATENT AND TRADEMARK OFFICE
CERTIFICATE OF CORRECTION

PATENT NO. : 6,956,040 B2
APPLICATION NO. : 10/051784
DATED : January 17, 2002
INVENTOR(S) : Anita Mehta et al.

It is certified that error appears in the above-identified patent and that said Letters Patent is hereby corrected as shown below:

Column 41, Line 6 – "(m 2H)" should read --(m, 2H)--

Column 42, Line 54 – "-]4-" should read -- -[4- --

Column 45, Line 45 – "!H" should read --1H--*

Column 46, Line 53 – "7.24 7.11" should read --7.24-7.11--

Column 47, Line 20 – "dissoved" should read --dissolved--

Column 47, Line 30 – "Fluoro4-" should read --Fluoro-4- --

Column 47, Line 43 – "8H,)" should read --8H)--

Column 47, Line 47 – "Fluoro4-" should read --Fluoro-4- --

Column 48, Line 18 – "Fluoro4-" should read --Fluoro-4- --

Signed and Sealed this

Second Day of September, 2008

JON W. DUDAS
*Director of the United States Patent and Trademark Office*

UNITED STATES PATENT AND TRADEMARK OFFICE
CERTIFICATE OF CORRECTION

PATENT NO. : 6,956,040 B2  Page 1 of 2
APPLICATION NO. : 10/051784
DATED : October 18, 2005
INVENTOR(S) : Anita Mehta et al.

It is certified that error appears in the above-identified patent and that said Letters Patent is hereby corrected as shown below:

Title page, Title – "piperazinyl" needs to be removed

Title page, Other publications, Line 1 – "Medicianl Chemistry" should read --Medicinal Chemistry--

Title page, Other publications, Line 21 – "Comparitave" should read --Comparative--

Title page, item (74) – "George F. Heibel, Esq." should read --George E. Heibel, Esq.--

Column 7, Line 27 – "(R6,R7)" should read --(R6, R7)--

Column 18, Line 17 – "Citrate slat" should read --Citrate salt--

Column 25, Line 47 – "(1a, 5a, 6a)" should read --(1α, 5α, 6α)--

Column 27, Line 23 – "cetamide" should read --acetamide--

Column 29, Line 7 – "Compound No. 15" should read --Compound No. 17--

Column 29, Line 16 – "(br s," should read --(br, s,--

Column 29, Line 16 – "H)." should read --H),--

Column 31, Line 15 – "yied" should read --yield--

Column 32, Line 46 – "so" should read --solid--

Column 35, Line 65 – "tat" should read --that--

Column 36, Line 6 – "Nethyl" should read --N-Methyl--

Column 36, Line 30 – "CH2Cl2" should read --$CH_2Cl_2$--

Column 39, Line 31 – "J=12H" should read --J=12Hz--

Column 40, Line 29 – "-193" should read -- -1.93--

Column 40, Line 55 – "(3 3H)" should read --(t, 3H)--*

Column 40, Line 56 – "Methyl, N-1" should read --Methyl-N-1--

UNITED STATES PATENT AND TRADEMARK OFFICE
CERTIFICATE OF CORRECTION

PATENT NO. : 6,956,040 B2
APPLICATION NO. : 10/051784
DATED : October 18, 2005
INVENTOR(S) : Anita Mehta et al.

It is certified that error appears in the above-identified patent and that said Letters Patent is hereby corrected as shown below:

Column 41, Line 6 – "(m 2H)" should read --(m, 2H)--

Column 42, Line 54 – "-]4-" should read -- -[4- --

Column 45, Line 45 – "!H" should read --1H--*

Column 46, Line 53 – "7.24 7.11" should read --7.24-7.11--

Column 47, Line 20 – "dissoved" should read --dissolved--

Column 47, Line 30 – "Fluoro4-" should read --Fluoro-4- --

Column 47, Line 43 – "8H,)" should read --8H)--

Column 47, Line 47 – "Fluoro4-" should read --Fluoro-4- --

Column 48, Line 18 – "Fluoro4-" should read --Fluoro-4- --

This certificate supersedes the Certificate of Correction issued September 2, 2008.

Signed and Sealed this

Seventh Day of October, 2008

JON W. DUDAS
*Director of the United States Patent and Trademark Office*

UNITED STATES PATENT AND TRADEMARK OFFICE
CERTIFICATE OF CORRECTION

PATENT NO. : 6,956,040 B2
APPLICATION NO. : 10/051784
DATED : October 18, 2005
INVENTOR(S) : Anita Mehta et al.

It is certified that error appears in the above-identified patent and that said Letters Patent is hereby corrected as shown below:

Title page, and Column 1, line 1, Title – "piperazinyl" needs to be removed

Title page, Other publications, Line 1 – "Medicianl Chemistry" should read --Medicinal Chemistry--

Title page, Other publications, Line 21 – "Comparitave" should read --Comparative--

Title page, item (74) – "George F. Heibel, Esq." should read --George E. Heibel, Esq.--

Column 7, Line 27 – "(R6,R7)" should read --(R6, R7)--

Column 18, Line 17 – "Citrate slat" should read --Citrate salt--

Column 25, Line 47 – "(1a, 5a, 6a)" should read --(1α, 5α, 6α)--

Column 27, Line 23 – "cetamide" should read --acetamide--

Column 29, Line 7 – "Compound No. 15" should read --Compound No. 17--

Column 29, Line 16 – "(br s," should read --(br, s,--

Column 29, Line 16 – "H)." should read --H),--

Column 31, Line 15 – "yied" should read --yield--

Column 32, Line 46 – "so" should read --solid--

Column 35, Line 65 – "tat" should read --that--

Column 36, Line 6 – "Nethyl" should read --N-Methyl--

Column 36, Line 30 – "CH2Cl2" should read --$CH_2Cl_2$--

Column 39, Line 31 – "J=12H" should read --J=12Hz--

Column 40, Line 29 – "-193" should read -- -1.93--

Column 40, Line 55 – "(3 3H)" should read --(t, 3H)--*

Column 40, Line 56 – "Methyl, N-1" should read --Methyl-N-1--

UNITED STATES PATENT AND TRADEMARK OFFICE
CERTIFICATE OF CORRECTION

PATENT NO.        : 6,956,040 B2
APPLICATION NO.   : 10/051784
DATED             : October 18, 2005
INVENTOR(S)       : Anita Mehta et al.

It is certified that error appears in the above-identified patent and that said Letters Patent is hereby corrected as shown below:

Column 41, Line 6 – "(m 2H)" should read --(m, 2H)--

Column 42, Line 54 – "-]4-" should read -- -[4- --

Column 45, Line 45 – "!H" should read --1H--*

Column 46, Line 53 – "7.24 7.11" should read --7.24-7.11--

Column 47, Line 20 – "dissoved" should read --dissolved--

Column 47, Line 30 – "Fluoro4-" should read --Fluoro-4- --

Column 47, Line 43 – "8H,)" should read --8H)--

Column 47, Line 47 – "Fluoro4-" should read --Fluoro-4- --

Column 48, Line 18 – "Fluoro4-" should read --Fluoro-4- --

This certificate supersedes the Certificates of Correction issued September 2, 2008 and October 7, 2008.

Signed and Sealed this

Twenty-first Day of October, 2008

JON W. DUDAS
*Director of the United States Patent and Trademark Office*